US010837067B2

(12) United States Patent
B et al.

(10) Patent No.: US 10,837,067 B2
(45) Date of Patent: Nov. 17, 2020

(54) METHODS AND COMPOSITIONS FOR PRODUCING CORN PLANTS WITH RESISTANCE TO LATE WILT

(71) Applicant: Monsanto Technology LLC, St. Louis, MO (US)

(72) Inventors: Rakesh B, Karnataka (IN); Sunil Kumar Biradar, Bangalore (IN); Franck Jean Chopin, Boucau (FR); Romain Fouquet, Amendeuix-Oneix (FR); Sonali Dilip Gandhi, Rotterdam (NL); Erappa Gangappa, Karnataka (IN); Veeresh R P Gowda, Bangalore (IN); Yule Pan, Chesterfield, MO (US); Jean-Luc Pellet, Cremona (IT); Dharanendra Swamy, Karnataka (IN); Gonzalo Torres, Madrid (ES); Chongqing Xie, Johnston, IA (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 119 days.

(21) Appl. No.: 15/674,917

(22) Filed: Aug. 11, 2017

(65) Prior Publication Data

US 2018/0044740 A1    Feb. 15, 2018

Related U.S. Application Data

(60) Provisional application No. 62/373,777, filed on Aug. 11, 2016.

(51) Int. Cl.
| | | |
|---|---|---|
| *A01H 5/10* | (2018.01) | |
| *C12Q 1/6895* | (2018.01) | |
| *A01H 6/46* | (2018.01) | |
| *A01H 1/04* | (2006.01) | |
| *A01H 1/02* | (2006.01) | |
| *C12N 15/82* | (2006.01) | |

(52) U.S. Cl.
CPC ............ *C12Q 1/6895* (2013.01); *A01H 1/02* (2013.01); *A01H 1/04* (2013.01); *A01H 5/10* (2013.01); *A01H 6/4684* (2018.05); *C12N 15/8282* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,210,015 | A | 5/1993 | Gelfand et al. |
| 5,217,863 | A | 6/1993 | Cotton et al. |
| 5,468,613 | A | 11/1995 | Erlich et al. |
| 5,563,055 | A | 10/1996 | Townsend |
| 5,595,890 | A | 1/1997 | Newton et al. |
| 5,616,464 | A | 4/1997 | Albagli et al. |
| 5,762,876 | A | 6/1998 | Lincoln et al. |
| 5,800,944 | A | 9/1998 | Blonsky et al. |
| 5,876,930 | A | 3/1999 | Livak et al. |
| 5,945,283 | A | 8/1999 | Kwok et al. |
| 6,013,431 | A | 1/2000 | Söderlund et al. |
| 6,030,787 | A | 2/2000 | Livak et al. |
| 6,090,558 | A | 7/2000 | Butler et al. |
| 6,503,710 | B2 | 9/2003 | Chen |
| 6,613,509 | B1 | 9/2003 | Chen |
| 6,799,122 | B2 | 9/2004 | Benson |
| 6,913,879 | B1 | 7/2005 | Schena |
| 6,996,476 | B2 | 2/2006 | Najarian |
| 7,238,476 | B2 | 7/2007 | McKeown et al. |
| 7,250,252 | B2 | 7/2007 | Katz et al. |
| 7,270,981 | B2 | 9/2007 | Armes et al. |
| 7,282,355 | B2 | 10/2007 | Shi |
| 7,297,485 | B2 | 11/2007 | Bornarnth et al. |
| 7,312,039 | B2 | 12/2007 | Barany et al. |
| 2006/0141495 | A1 | 6/2006 | Wu |
| 2008/0083042 | A1 | 4/2008 | Butruille et al. |
| 2010/0223290 | A1 | 9/2010 | Almeida |
| 2011/0105347 | A1 | 5/2011 | Wu et al. |
| 2015/0240253 | A1* | 8/2015 | McGonigle .......... C07K 14/415 800/279 |

OTHER PUBLICATIONS

*Zea mays* cultivar B73 chromosome 2 clone CH201-56L5, GenBank accession No. AC195590, published Sep. 23, 2013, selected pages.*
Al-ameen, "Mapping of QTLs for Resistance to Late Wilt of Maize in Egypt Using SNPs," Thesis, American University in Cairo. Dept. of Biology, Jun. 4, 2013 [online]. [Retrieved on Oct. 19, 2017]. Retrieved from the internet <URL: http://dar.aucegypt.edu/handle/10526/3595> (2013).
Arús et al., "Marker-assisted selection," Chapman & Hall, London (eds.), *Plant Breeding*, pp. 314-331 (1993).

(Continued)

*Primary Examiner* — Bratislav Stankovic
(74) *Attorney, Agent, or Firm* — Arnold & Porter Kaye Scholer LLP; Matthew Madsen; David R. Marsh

(57) ABSTRACT

The present disclosure is in the field of plant breeding and disease resistance. The disclosure provides methods for breeding corn plants having late wilt (LW) resistance using marker-assisted selection. The disclosure further provides corn germplasm resistant to LW. The disclosure also provides markers associated with LW resistance loci for introgressing these loci into elite germplasm in a breeding program, thus producing novel LW resistant germplasm.

17 Claims, No Drawings

Specification includes a Sequence Listing.

(56) References Cited

OTHER PUBLICATIONS

Borevitz et al., "Large-scale identification of single-feature polymorphisms in complex genomes," *Genome Research*, 13:513-523 (2003).
Churchill et al., "Empirical Threshold Values for Quantitative Trait Mapping," *Genetics*, 138(3):963-71 (1994).
Cui et al., "Detecting single-feature polymorphisms using oligonucleotide array and robustified projection pursuit," *Bioinformatics*, 21:3852-3858 (2005).
Degani et al., "Diagnosis and Control of *Harpophora maydis*, the Cause of Late Wilt in Maize," *Advances in Microbiology*, 4:94-105 (2014).
Flint-Garcia et al., "Structure of linkage disequilibrium in plants," *Annual Review of Plant Biology*, 54:357-374 (2003).
Gaj et al., "ZFN, TALEN, and CRISPR/Cas-based methods for genome engineering," *Trends in Biotechnology*, 31:397-405 (2013).
Gianola et al., "Bayesian methods in animal breeding theory," *Journal of Animal Science* 63: 217-244 (1986).
Gruber et al., "Vectors for Plant Transformation," *Methods in Plant Molecular Biology and Biotechnology*, Glick B. R. and Thompson, J. E. (eds.) (CRC Press, Inc., Boca Raton, 1993) pp. 89-119.
Hedrick, "Gametic Disequilibrium Measures: Proceed With Caution," *Genetics*, 117:331-41, (1987).
Heffner et al., "Genomic selection for crop improvement," *Crop Science*, 49: 1-12 (2009).
Henderson, "Best linear unbiased estimation and prediction under a selection model," *Biometrics*, 31: 423 (1975).
Horsch et al., "A Simple and General Method for Transferring Genes into Plants," *Science*, 227(4691):1229-1231 (1985).
International Search Report and Written Opinion dated Nov. 8, 2017, in International Application PCT/US2017/046482.
Jannink et al., "Association Mapping in Plant Population," *Quantitative Genetics, Genomics and Plant Breeding*, Kang, Ed. CAB International, pp. 59-68 (2002).
Jansen et al., "High Resolution of Quantitative Traits Into Multiple Loci via Interval Mapping," *Genetics*, 136:1447-1455 (1994).
Jansen et al., "Genotype-by-environment interaction in genetic mapping of multiple quantitative trait loci," *Theoretical and Applied Genetics*, 91:33-37 (1995).
Kruglyak et al., "A Nonparametric Approach for Mapping Quantitative Trait Loci," *Genetics*, 139:1421-1428 (1995).
Lander et al., "Mapper Mendelian Factors Underlying Quantitative Traits Using RFLP Linkage Maps," *Genetics*, 121:185-199 (1989).
Lee et al., "Expanding the genetic map of maize with the intermated B73 × Mo17 *(IBM) population,"* *Plant Mol Biol*, 48:453 (2002).
Li et al., "Overview of LASSO-related penalized regression methods for quantitative trait mapping and genomic selection," *Theor Appl Genet.*, 125:419-435 (2012).
Lincoln et al., "Mapping Genes Controlling Quantitative Traits Using MAPMAKER/QTL Version 1,1: A Tutorial and Reference Manual," Whitehead Institute for Biomedical Research Technical Report, Second Edition, (Cambridge MA, 1993) pp. 1-43.
Mild et al., "Procedures for Introducing Foreign DNA into Plants," *Methods in Plant Molecular Biology and Biotechnology*, Glick B. R. and Thompson, J. E. (eds.) (CRC Press, Inc., Boca Raton, 1993) pp. 67-88.
Nakaya et al., "Will genomic selection be a practical method for plant breeding?" *Annals of Botany*, 110: 1303-1316 (2012).
Openshaw et al., "Marker-assisted Selection in Backcross Breeding," Proceedings of the Symposium, *Analysis of Molecular Marker Data*, pp. 41-43 (1994).
Ragot et al., "Marker-assisted Backcrossing: A Practical Example," *Techniques Et Utilisations Des Marqueurs Moleculaires Les Colloques*, 72:45-56 (1995).
Reich et al., "Linkage disequilibrium in the human genome," *Nature*, 411:199-204 (2001).
Samra et al., "Late wilt disease of maize caused by *Cephalosporium maydis,"* *Phytopathology*, 53:402-406 (1963).
Service, "Gene sequencing: the race for the $1000 genome," *Science*, 311:1544-46 (2006).
Utz et al., "Comparison of different approaches to interval mapping of quantitative trait loci," Biometrics in Plant Breeding: Applications of Molecular Markers, van Oijen, Jansen (eds.) *Proceedings of the Ninth Meeting of the EUCARPIA Section Biometrics in Plant Breeding*, Wageningen, the Netherlands, pp. 195-204 (1994).
Van Vleck et al.,"Estimated breeding values for meat characteristics of cross-bred cattle with an animal model," *Journal of Animal Science*, 70: 363-371 (1992).
Visscher et al., "Confidence Intervals in QTL Mapping by Bootstrapping," *Genetics*, 143:1013-1020 (1996).
Weber et al., "Advances in Plant Breeding," Blackwell, Berlin, 16:42-56 (1994).
Zeng, "Precision Mapping of Quantitative Trait Loci," *Genetics*, 136:1457-1468 (1994).

\* cited by examiner

SEQUENCE LISTING

```
<160> NUMBER OF SEQ ID NOS: 300

<210> SEQ ID NO 1
<211> LENGTH: 362
<212> TYPE: DNA
<213> ORGANISM: Zea mays
<220> FEATURE:
<221> NAME/KEY: misc_feature
<222> LOCATION: (287)..(287)
<223> OTHER INFORMATION: n is a, c, g, or t

<400> SEQUENCE: 1
ggtcgggtaa agacggcaag tacacggccc tcccgccgtt cgacgccatc gcccagaacc      60
ccgaggccag gttcctccac atctgctcca acgagaccat ccacggcgtc gagttcaagg     120
actacccgga gccccgcaac aggtcgggca tcctcgtcgc cgacatgtcc tccaacttct    180
```

```
gctccaagcc cgtcgacgtc tcccgcttcg gcgtcatcta cgccggcgca cagaagaacg      240
tcgggccctc cggcgtcacc atcgccatcg tgcgcaagga cctcatnggc gccgctcagc      300
ccatcacgcc cgtcatgctc gacttcaaga cgcacgccga caacgcctcc ctctataaca      360
cc                                                                    362

<210> SEQ ID NO 2
<211> LENGTH: 454
<212> TYPE: DNA
<213> ORGANISM: Zea mays
<220> FEATURE:
<221> NAME/KEY: misc_feature
<222> LOCATION: (163)..(163)
<223> OTHER INFORMATION: n is a, c, g, or t

<400> SEQUENCE: 2
ggagtcctcg gcttcaaacc tgcaccgatc acacttgcat tcgaaccccc aagctctcga       60
tgcctccctg cgcttgctca ccggcacaag cacatcaaag tatggaaatg tgatctcctc      120
cccggctttg atgtccctgg acgcgtggac gatggcatgg tcnccgatgt gagtgcgccg      180
agcattaggg tggcaggaat ggttgatgaa cgacggcaag acccagagcc ccacgccgca      240
attgacgacg ccattgttac caagcacatc ggcggctggc gcgtcctcag tcaagcaggt      300
cacatcgagc accttcaaga tcctgtccat ttgaacagcc tcctgtgtcc tcgtcgtctt      360
ccccgcggta gtaccatcac tgagactgtc atcctctgtt tctttcctga acattgccat      420
gtcagggacg gcaagctcgt cctgcctctc ctgg                                  454

<210> SEQ ID NO 3
<211> LENGTH: 842
<212> TYPE: DNA
<213> ORGANISM: Zea mays
<220> FEATURE:
<221> NAME/KEY: misc_feature
<222> LOCATION: (2)..(21)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (298)..(305)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (354)..(360)
<223> OTHER INFORMATION: n is a, c, g, or t
<220> FEATURE:
<221> NAME/KEY: misc_feature
```

```
<222> LOCATION: (400)..(401)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (762)..(763)
<223> OTHER INFORMATION: n is a, c, g, or t
<220> FEATURE:
<221> NAME/KEY: misc_feature
<222> LOCATION: (766)..(766)
<223> OTHER INFORMATION: n is a, c, g, or t
<220> FEATURE:
<221> NAME/KEY: misc_feature
<222> LOCATION: (831)..(837)
<223> OTHER INFORMATION: n is a, c, g, or t

<400> SEQUENCE: 3
tnnnnnnnnn nnnnnnnnnn naaatgcctg gcaatctcaa ggtaaaagta ctgtctgtct      60
gggtgcagtc ataacacgca ccatttcatt tatgttttg  gatcctgcag gttgcgtatt     120
ttgtgaattc tgggacngaa gcgaatgagt tggcaatgtt gatggcccgg ctgtatagtg     180
ggaatctcag tatggttgcg ctcngaaatg catatcatgg cggaagtgcc ggtacgattg     240
gattgactgg tntgcagacg tggaaatacc caattcctca ggtatgtgta cagtgtannn     300
nnnnnttgcn ctttcatnaa attatttgac tggttatgtt ttcanagtca catnnnnnnn     360
gtttgctgca gtagattctt agttatcaat aattatctcn ncgttctacc cagcaaaaat     420
gtatccattt ctttattaca tctatcatag cctcataaga attttttgcag ggtgaaatac    480 atcatgtcat gaaccctgat ccttatcggg ggactttcgg gtctgatgct gcagcttatg    540
ctaaggaagt cgaagaacac ataacttatg gaagttcagg aagggttgca ggcttcattg    600
cagaaacatt ccangtataa actttgaaca gaccatttat aaaatgctag aactaattga    660
aataatatgt atcttttgtt tataaaccca attcaaaata acttatcctt gtcgcaatct    720
tgttgataca ccatctctgc tgtagggtgt gggaggtgct gnnaantagc tcctggatac    780
ctaaagttag cttatgacat tgtgcgcaag gctggtggcg tttgtattgc nnnnnnngtc    840
ca                                                                    842

<210> SEQ ID NO 4
<211> LENGTH: 1083
<212> TYPE: DNA
<213> ORGANISM: Zea mays
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (294)..(297)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (615)..(620)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (896)..(897)
```

<223> OTHER INFORMATION: n is a, c, g, or t

<400> SEQUENCE: 4

```
gtgatgtcag attgtttgga ataaccagat aaacatctat cgggttgact gattcatatc    60
ctttcagtgt tgctgannac taactgaatg aaagtaggca gacttctgaa ttaattgcaa   120
ttttgggaag tgtaacatac aaaaattatc ttgtgtccga ggaaatggat tgattgattc   180
agaaaaccaa ccaccctggt tgtgcaaacc aaaaaaagaa caatatagag cagtaaaggt   240
tgattataac cagcattcca gcaatgaagc caacagtacc attacaaaag caannnngtc   300
aacatgagac atacctgaag gataaggcac gtatgtcaaa tcacttgcag cccactgaat   360
atggaatcat tagtgataga aactgatatt caanttctat tgcatagagg gtggttacat   420
atatagaccc aggggaaccc taaccctaat gggctagcag cccatttaca catacatgga   480
taatatagga gcatacactc taacaatcag tctggtggag aagctggaaa tacacagtac   540
aaaagtagca gaaatagaga aagtacttaa aaatgagaat ataaaaggtc aaatagttta   600
gagttgccat acttnnnnnn gtgaagaata tgttcctagt caggaaagca atttacggtt   660
gccaacgcta gtgaaaaata tgaaagatat gaatcaagta cagtactatt tgacgaccaa   720
atataacctt gatgaatgtc tcccaacaac cagccaacta ggataaggat ttntaatgtc   780
aacccactga aaactaaaga ttcattagca ttctacaaag cagatgttac aatctaaaat   840
atgttcaatc agcagggaaa tggtgataaa acctcaaagc taatttaaaa cagttnnctg   900
cctataaact gctggttctc actaacacat acatgtacag ttaaatcact ccagtcaacc   960
cacttattca gaagaataga ctgctatgga gctgtgagct atatacgaga gagatcgcca  1020
tttatatttg atcaagtatc tggctttctc tttgaaaggg ggctaaatgc agctgcaggc  1080
atg                                                                1083
```

<210> SEQ ID NO 5
<211> LENGTH: 201
<212> TYPE: DNA
<213> ORGANISM: Zea mays
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 5

```
gtgtgcgaga acttcgtctg acaactgaag nataccgcag tggtctgcac tctggacttt    60
cggagcatgc tcatgggaag ctgagttcag atcttgaatg ntgggcctgt tgttggtctg   120
ttgcttgtac accggatacg acacgctgct gagatcgatg tttgcctcgg agaatagttg   180
gattccaatc acatgtgtca c                                             201
```

<210> SEQ ID NO 6
<211> LENGTH: 669
<212> TYPE: DNA
<213> ORGANISM: Zea mays
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t

```
<220> FEATURE:
<221> NAME/KEY: misc_feature
<222> LOCATION: (299)..(299)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (527)..(527)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (643)..(644)
<223> OTHER INFORMATION: n is a, c, g, or t
<220> FEATURE:
<221> NAME/KEY: misc_feature
<222> LOCATION: (646)..(647)
<223> OTHER INFORMATION: n is a, c, g, or t
<220> FEATURE:
<221> NAME/KEY: misc_feature
<222> LOCATION: (649)..(650)
<223> OTHER INFORMATION: n is a, c, g, or t
<220> FEATURE:
<221> NAME/KEY: misc_feature
<222> LOCATION: (664)..(666)
<223> OTHER INFORMATION: n is a, c, g, or t

<400> SEQUENCE: 6
acaaatcact cgctactctt gcctacaccc tcacaatcat ntacgaatac tagtgactgc    60
tttcctctcc tcagcatttt tggcaagtgt tgtgctggcg tgccgtgtgt ggagnggaac   120
gctatataaa gcaacgtcta aaaagaaaa aaaatactat atattagcat actagtatat   180
aaatataaga gtaactccaa tagttttcta aaagactctc taaattaata atttaagtaa   240
ctaaactaaa agctcctctc caacggttct ctaaatgaac ttcataaatt tagctactnc   300
tcatctaacc ttatttttctc tctacattta gnaacnattt accaactncn taaacaaaaa   360
aaaattgacn gtaattttg tatttcgctg ccttttttcac tttatagtaa cgatatatta   420
acatagccca tgcgtcgaac aacgacagtc agctagagat taaataattg ccaatacaat   480
```

| agccgcacgt ncacntgtcg gaaataaata aataaacaat tgcaacngta aatnaaaaga | 540 |
| tcaacacaac tcaccaagtt gaatatgcca tcgatnatgg tcccactcag atgagtgaca | 600 |
| tgttaaattt taacatattt agaaagtaat atatatataa ctnntnnann agatgcgttt | 660 |
| tttnnntat | 669 |

<210> SEQ ID NO 7
<211> LENGTH: 2607
<212> TYPE: DNA
<213> ORGANISM: Zea mays
<220> FEATURE:
<221> NAME/KEY: misc_feature
<222> LOCATION: (2239)..(2239)
<223> OTHER INFORMATION: n is a, c, g, or t

<400> SEQUENCE: 7

| caggaaaaaa acccggtgtt ctagccgcac gcatctcaaa ggtgatactg ggcggggcga | 60 |
| tttggagatg atgttctagc actagcagca cgcacgcatc tcaaaggtga tactgggcgg | 120 |
| ggcgatttgg agatgatgtt ctagcactag cagcacgcac gcatctcaag gtcatactgg | 180 |
| gcggggcgat tgcgagtcc tgtggcctcg tgggccacgt gcacgcagca gaccgcagga | 240 |
| atttgcacga gaccagtacc tagaacaccc tactccagcg aaatccgcca cttcgtcgtc | 300 |
| gtcgtcgcac ggattggcat tggctgcccc ccggccctgt tcctcgtcct cctcatcaat | 360 |
| tcccgtctct cagtcctccc aataatggtg gcgtggtgag aaatccttcc gtccggccgt | 420 |
| cgtcttagaa gatgaactgt tcctcttgct gcgccgctgc cactccatct tctccggcgc | 480 |
| ttctcgccag gccgcggggg ggtttagctg ctagctgctc cacgacgaca gcaaatcaga | 540 |
| aggtgctttt cctgggctca aaacagtttc cacggatcac gtatagccgt gcgtcgtcac | 600 |
| ggttgtcgcg gagagaggta atagcttttg ccgggcaaca accttgggac atcggcagat | 660 |
| ttgtcaagac gctgtatttc ttcaacgggc ctccaaacct tctcaagatt gtagaatcta | 720 |
| tcatcagcag tttcactgga cctgcttcta gtgaagtgcc aaagaaaatg gaaacgtcgg | 780 |
| atgtggtgct ggttactgga gccaccggtg gtgttgggcg acgggtggtg gacgtcctgc | 840 |
| agaagaaggg agtacctgtt cgagtattgg ctagaaatgt agacaaggca aggagcatgt | 900 |
| tggggccgga tgtacctctg atcataggag atgttacgaa ggaagataca cttgatccta | 960 |
| agctattcaa agggataaaa aaagtagtca atgcagtctc tgtcatagtg gggccaaagg | 1020 |
| aaggtgatac gccagacagg cagaagtaca acaaggcat caaattttc gaacctgaga | 1080 |
| tcaagggacc ttcacctgaa atggttgagt acatcggaat gcaaaacttg attaatgcca | 1140 |
| taaagagtag tgttggactg agtgaaggga aactgctatt tggtttcaaa ggcaacttat | 1200 |
| ctggagagat tgtgtgggga gctcttgatg acgttgtgat gggtggtgtt agtgaaagta | 1260 |
| cattccaaat cttgccaaca ggaagtgaaa gtagtggacc aactgggttg ttcaaaggga | 1320 |
| ctgtatctac ttcaaataat ggtgggttta ctagtataag gacaaagaat tttactgtgc | 1380 |
| cagaggacct gtcagcatat gatggtattg agttacgagt taatggtgat gggcgacggt | 1440 |
| ataaactcat tatacggact agctatgaat gggatactgt tggctataca gcaagttttta | 1500 |
| acacaactaa gggggatgg caaagtgtta aagtaccttt ctcttctctg aaacctgtat | 1560 |
| tccgtgctcg tactgtgact gatgctccac ccttcgatgc aagcaacatt acttcactac | 1620 |
| aactcatgtt tagcaaattt gaatacgatg gaatactcaa cccaacattt actgaaggtc | 1680 |
| cgtttgagct tccttttcg agtattagag catacatcaa tgagccgatc actccaaggt | 1740 |
| tcgttcatgt gagttctgcg ggagttacaa gacctgaaag accggggtta gatttaagca | 1800 |

```
agcagccacc tgctgttcga ttgaacaaag agcttggctc cattttaact tttaagttga   1860
agggagagga tttaattcgg gaaagcggta ttccgtacac tattgtaagg ccatgtgcat   1920
taactgagga accagctgga gccgatctca tgtttgacca gggggacaac atcacaggaa   1980
agatatcaag ggaagaagtt gcccgtattt gtgtagcagc tctggcaagc ccagatgctg   2040
tgggcaaaac tttcgaggtc aagagcactg ttccattcag cgaaccgtat gtgattgacc   2100
ctgcaaatcc tcctcctgaa aaggactatg aagtatattt caaagaactc aaagaaggca   2160
tcacgggtaa agaggcgtta gaggcaacac ctgctcaagt ttgaagatgt cgttgaatta   2220
agaatttcgt ctgttttcnt aaattctgac acagtaaccc ccactctgaa tgtctaaagt   2280
catctagaaa catagatgac actaatgcta aattttgtag ctgaagatca gaccaataaa   2340
tattcccaag aacacattac tgttaggttg ggggatcatt aaactcgagc taagacacaa   2400
atatgtagat gaaattagtg ctgctgttca tgccttcgtt ggagttagcc attacaggac   2460
acaagaattt agtaagaggt ttggcaaaaa aaaaaaaaaa aaggagcagc tgcctgatga   2520
gttggtagag tggttgcttt cagtcaattc tctagggtgc ctatctctat ttaacttgat   2580
gctgcacact gggggctccc ttcagtc                                       2607

<210> SEQ ID NO 8
<211> LENGTH: 360
<212> TYPE: DNA
<213> ORGANISM: Zea mays
<220> FEATURE:
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t

<400> SEQUENCE: 8
aacagcagtc agcatttcaa atacgaaaga ctggaactgt ggagcaagta acaacactca     60
catcatttct aacacttgga attgctaaat tctcagcatt cttgattcca agggtagtga    120
gctcccgtag agatgtctgt ttcagaatgc aggctcatca gttagaatca atcagagcca    180
gacacaacca tcaaatgcta ctgcattgta aaaattgcac gagcaaaacg catgacagga    240
gtangcatcc tgcaaacacg aagcgctcaa tcattgatgc ctgagaagat ncagcactga    300
ccgtccggcg cgacacatag ggctgcgagc cccaccgctt ggcccatccg ctctctctca    360

<210> SEQ ID NO 9
<211> LENGTH: 752
<212> TYPE: DNA
<213> ORGANISM: Zea mays
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (722)..(730)
<223> OTHER INFORMATION: n is a, c, g, or t

<400> SEQUENCE: 9
ttatgaacga gtacgtgcct tgaaccttga ttatgtttga ctgtaattaa atgtttgttc     60
ctgaccaagg cattgagaaa gctttgttct tgttccagaa actacaaccc tgtagaaagg    120
aggtcaaagg gatgcaaaga acgtgtctca aagggttcca ataagccatc taaatcattg    180
```

```
caagccaata ggctttctgg tgctgatcca acagatggag gtgcagagtc tatctgatca    240
ttgattaagt gcttgtctaa ctaaatcatn agggtgcatc tagcagcctt ttttttcttt    300
gacatacgca taggtagtgc tactacacag tgtgattgtt attgttctga aatgatgtaa    360
ctgttagagc tggtttggga gtccaaaaac cggaggggat tggagaggct aaaatcatct    420 tcttttcaa aattgaataa ggaggggatt ttagcccctc taatcccctc cggttttgtg     480
gctctcaaac tagcccttag agggaattac tgctctcaac cctttgtctg cttagggatg    540
ttgtaaaggg cgtacccagt gccgtaggct tcccgcactg tgcgggtct ggggaagggt     600 atctttaagc gccaagtctt acccgtataa aatgcagagg tttagggatg ttgtaaagtt    660
tacaattttt atgcttctgt ttgttattaa tatctacatg ctaatccaat tatgcaggcc    720
annnnnnnnn gaaagtatgt aacacttttt ct                                   752

<210> SEQ ID NO 10
<211> LENGTH: 827
<212> TYPE: DNA
<213> ORGANISM: Zea mays
<220> FEATURE:
<221> NAME/KEY: misc_feature
<222> LOCATION: (430)..(430)
<223> OTHER INFORMATION: n is a, c, g, or t

<400> SEQUENCE: 10
aacaaaatga gcaattgcac cagtttttcc tttcttgatg attttcacc aaggtacatg      60 ttgagtttta ttaccttgat tctaactaat ggaagtttgg gctctgatct gctggcagtt    120
ggttggctac tcttctcaat cagatttctt acctaaagca atccagtaat acaatacca     180 aaaaaccagt taatttttt ttactgaaac taacatttaa gaaaaaagct tgttaggcaa     240
gagaaaataa caaacaaact attcttgaat gtttcttaat aacatggata aaaattgagt    300
aatagaatgc aaatacgtga actcacaatt ttatccaaat gttcaagcac agagtcctga    360
tcatttgagt taacatctgc ttcatctttc aacacaacct acgaatatca attgtgagat    420
ttactaactn atatacgaag cattaagtac gaaaggacat gcctcagcat attcaaaagg    480
tctgacagat ctcagaggta ttttggttgg cctgtactga tttccctgtt tatgaaacat    540
gtaaggactc agaaaataca ccaagcccat gaaacatgag agttttatcc acatgaaaca    600
tgagagttta tcttgaaaga agaacctgat ttctaacaaa agaacatgcc ttgggtttgg    660
cttacccatc aataaggacc tcgcgactga taaacctggt tgggtgatgt ggaaacccat    720
tccaggggac cctctgggaa tagaatattt acctttggaa tgcctgaccc aggtttttt     780 ctcttaaaaa acattttcac aaacaactta agctagaggg ccattta                  827

<210> SEQ ID NO 11
<211> LENGTH: 545
<212> TYPE: DNA
<213> ORGANISM: Zea mays
<220> FEATURE:
<221> NAME/KEY: misc_feature
<222> LOCATION: (269)..(269)
<223> OTHER INFORMATION: n is a, c, g, or t

<400> SEQUENCE: 11
caatgaagtt gttgaaaatt cagtatgtct atttccgcaa aattttattg tctatgaaaa     60
taacctggat tgcgttgtat gcctaccaaa tcatttcatg atatgttttt attctcaaat    120
gtctgcagga agaggagagt gcgcaacaag ttggacgtaa aagagcagct cctagggta     180 gaggtagagg tagaggcgga ggttccactg caaagagggg gcgaaaaaca gatattgctt    240
```

```
ccatgcaaaa tatgatgagc aaagatgang atgattcaga agatgaaccg ccaaagaaaa      300
ctcctcgggt cagaatttca cctgagtgtt ctcagttcac atattgtagc caaattttgt      360
gatgcgctac acctgaaagc aaacatattg tgtaaaatga gttgactcag taagattttc      420 tttttggtc tttcgcaggt caccaggaac tatggcgctg tcaggaggag atgaccctt       480 aaggagttct tgctcatgag agttataggc taggtgtttt gtcttgtaaa gttggaagag      540
ccgac                                                                 545

<210> SEQ ID NO 12
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t

<400> SEQUENCE: 12
tcggcttggc ttgtttccac ccttaaccga gagactggat aagttgtgtg actagccgtg      60
ntggctgaca cttgaagaca ttgacaaacc tgagtacntg gaggagcgaa tcgtgtcncc     120
g                                                                    121

<210> SEQ ID NO 13
<211> LENGTH: 121
<212> TYPE: DNA
<213> ORGANISM: Zea mays
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 13
gatcacctat tcacccccct ctaggtgctc tnaagttgcc ccgccttgct gggttgctct      60
ncaggcaggt gggtaggtag tcccgcctcg atgtgttgct cgacatagag gttgatcggt     120
a                                                                    121

<210> SEQ ID NO 14
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t
```

<400> SEQUENCE: 14
aggtccattt actatgccag tggatctatt gaatcgaacc cttgtctgac gatagtctgg    60
ncgacatata attgtttttt tttcagaanc tgcttccaag tctctagctc tctgcnggtg   120
c                                                                  121

<210> SEQ ID NO 15
<211> LENGTH: 245
<212> TYPE: DNA
<213> ORGANISM: Zea mays
<220> FEATURE:
<221> NAME/KEY: misc_feature
<222> LOCATION: (138)..(138)
<223> OTHER INFORMATION: n is a, c, g, or t

<400> SEQUENCE: 15
gatgtcagca agattgatgg ttgctaacaa tgaccttgtg ctgtttctta ccgggttttg    60
acgtgttgga tttgtgatta ccactgattg ctattgtact tcaaacagga atggctggaa   120
atgcaactcg gcttctcntg agaccttgtc atttgctgta gttcgttcgc aactgtatat   180
tgtagcttgg aagactctgt gccgtggtgc gtgtatttga gaaatttcta tgcaaagtga   240
gctgg                                                              245

<210> SEQ ID NO 16
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t

<400> SEQUENCE: 16
aactactgca acgatgtctg gcggtttcca cacgccggcc gagctgcaag accgactgat    60
natgcatggc tcactggttc tgagttcgtg ccattctgat gtacngtaac aaacanacaa   120
a                                                                  121

<210> SEQ ID NO 17
<211> LENGTH: 201
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (197)..(197)
<223> OTHER INFORMATION: n is a, c, g, or t

<400> SEQUENCE: 17

```
ccgatgaggt tagctacaat gtcactcgaa tctagtaggt agaagatcag ctgagagagc    60
ctagctagct agnagcagca ggtcaataag ctttaatcaa ngcatcggct tcaacattct   120
ttttgatttg cttctacaca acgtactact acgctgtata cacagtgacg cacnatgaac   180
acaattcaag tccagangcg a                                             201
```

<210> SEQ ID NO 18
<211> LENGTH: 707
<212> TYPE: DNA
<213> ORGANISM: Zea mays
<220> FEATURE:
<221> NAME/KEY: misc_feature
<222> LOCATION: (409)..(409)
<223> OTHER INFORMATION: n is a, c, g, or t
<220> FEATURE:
<221> NAME/KEY: misc_feature
<222> LOCATION: (563)..(564)
<223> OTHER INFORMATION: n is a, c, g, or t
<220> FEATURE:
<221> NAME/KEY: misc_feature
<222> LOCATION: (607)..(608)
<223> OTHER INFORMATION: n is a, c, g, or t
<220> FEATURE:
<221> NAME/KEY: misc_feature
<222> LOCATION: (614)..(617)
<223> OTHER INFORMATION: n is a, c, g, or t
<220> FEATURE:
<221> NAME/KEY: misc_feature
<222> LOCATION: (629)..(634)
<223> OTHER INFORMATION: n is a, c, g, or t
<220> FEATURE:
<221> NAME/KEY: misc_feature
<222> LOCATION: (638)..(646)
<223> OTHER INFORMATION: n is a, c, g, or t
<220> FEATURE:
<221> NAME/KEY: misc_feature
<222> LOCATION: (650)..(652)
<223> OTHER INFORMATION: n is a, c, g, or t
<220> FEATURE:
<221> NAME/KEY: misc_feature
<222> LOCATION: (655)..(704)
<223> OTHER INFORMATION: n is a, c, g, or t

<400> SEQUENCE: 18

```
atcgccaagt acaggcccac catgcctgtt ctttctgttg tcattcctcg tctgaagaca    60
aaccaactga gatggagttt cactggtgct tttgaggtac gtgaacccca atattctttg   120
tgatctttcc tgttagatgt tttcttttta tgcaacactg acattatcta ttattagcat   180
gttgatcatt tcttttgtga atggtaacat tggtctttga agtttctctt gtagatattg   240
aacatgtgtc atgcaatgct taagagagat tactttattt gagaagaatt aagaaccttg   300
attgccttct cttgtactga tacttggcac catgcaactc atttgttgtt tcttttttctt   360 gcaggcaaga cagtcgctga tagttagagg cctctttccg atgcttgcng atcctcggca   420
tccagtaagt taactgaagt ctttcagttc actactttgt ataagcaaca catactggct   480
gcactgctca cttgtacaca tgagcaactc atttctagca tcgttgggga tggaaagatt   540
ttgcaaacac atccccattg ccnntgtatt cttggacaag cattttttt attcatctat   600 tttggtnnga tatnnnntga aaacttgann nnnnttgnnn nnnnnnatgn nnctnnnnnn   660
nnnnnnnnnn nnnnnnnnnn nnnnnnnnnn nnnnnnnnnn nnnntca              707
```

<210> SEQ ID NO 19
<211> LENGTH: 713
<212> TYPE: DNA
<213> ORGANISM: Zea mays
<220> FEATURE:

<221> NAME/KEY: misc_feature
<222> LOCATION: (215)..(215)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (430)..(430)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (677)..(677)
<223> OTHER INFORMATION: n is a, c, g, or t
<220> FEATURE:
<221> NAME/KEY: misc_feature
<222> LOCATION: (710)..(712)
<223> OTHER INFORMATION: n is a, c, g, or t

<400> SEQUENCE: 19

```
atggtgactc cccacataaa atccaaggca gaagccacca aagccctcgg gtaaccttc      60
ttgcttagag attgctctga ataagtccac ctcaatcttt tttagtgatt ccactgtctg    120
tagaaagctt ctttcttgta caaggaatcg ttcctggaat attccctcct atgttattcc    180
cctgttagtt tgccaaccaa tcacagctct taaangggtg attactgatt gtccatgctt    240
ttctcatgct gagtaaacta agcagtaaca naaaacagat tgtgcagtgt cagtagctat    300
tatatatggt gacacctctg tattttatta tagcttgtat gtttaccta tcttnattga     360
ttgttaacta tgtaacaaag acagtttcgt tgtttgaacc ttgcaggttt cggggtttca    420
gtattctccn agcccacaga ggtttagtga gtgccacata tcatcttcca ctgatatagc    480
attcagtttt tgtattttca gtaatgcagt agtaatgtac ttatggcagt atgcnctttg    540
cngctgaaat tttagacggt tcaacttcag agatagctaa caatgggtct gagtcaacaa    600
tggatgcgaa gcgtagggcc agncctgtac cagcacatca taactccagg cagatgaaca    660
acaatcatca ttctacnact actactacta ccaccaccac gtcatctgcn nna           713
```

<210> SEQ ID NO 20
<211> LENGTH: 201
<212> TYPE: DNA
<213> ORGANISM: Zea mays
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t

<400> SEQUENCE: 20
tgaattagga cttctgtttt ctcactaaac taggtctnta ttttaatctc ttaaacaaac    60
ctatgcaaat aaccaaacac gcttgtgcaa ctaaggtttt ntctaagtgt tgctacctct   120
actgnaaaag gagttttgta acctaagttc caatcctacc aactagtctt tattctaaac   180
taagaatggt aacgataaca a                                            201

<210> SEQ ID NO 21
<211> LENGTH: 354
<212> TYPE: DNA
<213> ORGANISM: Zea mays
<220> FEATURE:
<221> NAME/KEY: misc_feature
<222> LOCATION: (148)..(148)
<223> OTHER INFORMATION: n is a, c, g, or t

<400> SEQUENCE: 21
ggggcgtgct tccccagcct tgaggacgct gatggcatgg agttcctcga cagccaggag    60
gcgatgacgt atcacagtcc caccaacgcg gccgagcaaa ccattagcga cgttgctcaa   120
ggcgtgcttc ttcggcctag agatggtngc tgcatctgtg tagtaccatg ctttcgtgca   180
aagaagcagc tgctagagga aagggaacag atgagtggag tgtgggtccc acacaactga   240
aggataggct tgatgcagtg gtgagagctg tctcactgag tcaccaggtc gtaggttgcg   300
ggggaaggct tgcctcacct agaccectca tgtgggagca tccggcactc tagg         354

<210> SEQ ID NO 22
<211> LENGTH: 201
<212> TYPE: DNA
<213> ORGANISM: Zea mays
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t

<400> SEQUENCE: 22
cggtcataga aattttcaat tttagtgtta ntntttctca taaataatgc gaagcaaatc    60
acataggtac cantctacca atttataatg tttttgtaga nataaatgac cgattaacat   120
ctcaaggagc caattactga ttaaggtaaa atactttttt cttgcgtgag ttccaaggaa   180
accttggtac tattgntctc t                                            201

<210> SEQ ID NO 23
<211> LENGTH: 201
<212> TYPE: DNA
<213> ORGANISM: Zea mays
<220> FEATURE:
<221> NAME/KEY: misc_feature
<222> LOCATION: (53)..(53)

```
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 23
acctgcagat aacgtgttgt ctcaccctat ctctatagcc agaaaagctg ttnttttccc      60
cttccacttn tgctgtnaga ggacatacac atactccacg ncacctcaaa ttggttttgc     120
atcgagcttc gtcgtcgtag gcaacacaaa gctagccctc gaagagtatt cggagcatat    180
tcctcgtttt gaacggtttt a                                               201

<210> SEQ ID NO 24
<211> LENGTH: 374
<212> TYPE: DNA
<213> ORGANISM: Zea mays
<220> FEATURE:
<221> NAME/KEY: misc_feature
<222> LOCATION: (283)..(283)
<223> OTHER INFORMATION: n is a, c, g, or t

<400> SEQUENCE: 24
ctttcctccc tggcgcagtt acaggccaaa aactaagctt ctctgccgaa aatgcggagc      60
atctatcggc tatggatacg gtgagccagc tggtttgtgc agttttgatc cagcaagttc     120
atcttcctcc agtacatccc agaagtattt aataaagatc caagcactcc aaccttcaga    180
cgggacccag taagtcagat atggaaagag agacaataga tgccagctta gagaactcca    240
tcagttacct atctgacgac tgcttgcttt ctatatttaa cangctagaa agcgagtcag    300
agaggagtgc ttttggtttg acctgcaaga attggttcaa ggttcggaac cttggtcgga    360
aatcactaac attc                                                       374

<210> SEQ ID NO 25
<211> LENGTH: 387
<212> TYPE: DNA
<213> ORGANISM: Zea mays
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (69)..(73)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (313)..(314)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
```

<220> FEATURE:
<221> NAME/KEY: misc_feature
<222> LOCATION: (334)..(336)
<223> OTHER INFORMATION: n is a, c, g, or t

<400> SEQUENCE: 25

```
nnnnnnnnnn nnnnnnnnnt tgcccccgca atgtgtacat cctgaccagc agaagtgatc      60
cactacagnn nnnaagaaca aagctagagt gagaagaaca nggaggaact aagctaactc     120
ccggcctaat tatgggatgg gttggacctg ctcttgggcg tcgtcttcaa gctctcgaac     180
aacaccgtng ccggtgcctt gaaggcttgg ctgaacccgc ccacaggcgt cgagcaggag     240
tcacggcatt gcgtcgacag aagccttctg ctcctcactc tcacaacaga cggttgcagc     300
tgcaacggct ggnncgangg cgatgaagaa gaannngaag aagggccaca gagcaggaca     360
aagaagagaa ggatcagcag agctgag                                        387
```

<210> SEQ ID NO 26
<211> LENGTH: 1674
<212> TYPE: DNA
<213> ORGANISM: Zea mays
<220> FEATURE:
<221> NAME/KEY: misc_feature
<222> LOCATION: (562)..(576)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t

<400> SEQUENCE: 26

```
cctgccccgt cccgtccgtc tccgtcccaa tcggatccac ccgcccgtcg tcgcctataa      60
actctccctc ccatccgtct cttgaggggg gcccggcttc ctcccaactg ccaccgattt     120
gtttgttcgg cttcggcccc atctccagtc acccgttccc acttcattgg tcgctgctcc     180
ctccctccac ggccgatccc gtgccggcga gagggaccat ggcggggaaa gggaaggagg     240
tgtacgtggc cgccatcgac cagggcacca caagcacccg gttcatcgtc tacgaccgcc     300
acgccaaacc cgtcgcatcg caccagctcg agttcaagca acactacccg gaggcagggt     360
gggttgagca tgatcctatg gagattatag agactgttaa ggtgtgtatg aaagaggcag     420
ttggcaaagc caaagctggt aaacacaatg tggttgctgg tttgaaggcc attgggatca     480
caaatcagag ggaaaccact gttatgtgga gtaaatccac tggccgtcca ctgtataatg     540
ccattgtgtg gatggatgct cnnnnnnnnn nnnnngcag gagattggaa aatgagctgt     600
caggcggtag aacccacttc gtggagacat gtgggttgcc aatcagtacc tatttcagtg     660
ctctgaaatt attntggttg atggaaaatg tggatgctgt caaggatgca gtccggactg     720
gtgacgcctt attcggcacg atcgacacct ggttgatttg gaaccttaca ggaggtgttg     780
ctggtgggca gcatgtcacg gattgctcaa atgcatctcg tacaatgctt atgaatctaa     840
agacacttga ctgggataag ccaacacttg ctgtgttagg agttcctgtt gagattttgc     900
caaagattat cagtaattca gagaaaatcg gtgtggtcgc caaagagttc ccgtttgcag     960
gagttcccat ctcggggtgt cttggagatc agcatgctgc tatgcttggg cagctgtgcc    1020
agaagggtga agcgaaaagc acctatggaa ctggtgcctt catccttctt aacacagggg    1080
aagagcctac ccaatcctcc catggccttc ttagtaccat tgcttacaag cttggtccag    1140
ctgcacccac taactatgct cttgaagggt ccattgcaat tgcaggcgca gcagttcagt    1200
ggctgaggga cagccttgga atcattcagt cagcagctga gatcgaaaag ttggctgaaa    1260
```

```
cagtgccaga ttcaggtgga gtgtactttg tgccagcatt taatgggttg tttgcaccat    1320
ggtggagaga tgatgcgagg ggaatttgca tcggaatcac aaggttcaca ataaggggc     1380 acattgctcg agcagtgctc gagagtatgt gttttcaggt gaatgatgtc ctcagctcca    1440
tgcacaagga tgctggagag gcaggagaag taaagagcgc agaaggagag ttcttattgc    1500
gtgttgatgg tggtgctact gttaataatc ttctaatgca gatccaggct gatttattag    1560
gcagccctgt tgtcagacca gctgacatag agaccacagc cctcggagct gcatatgctg    1620
ctgggttggc tgcaggagtt tggaccaagg agaaggtttt tgcaggtttg caca           1674
```

<210> SEQ ID NO 27
<211> LENGTH: 628
<212> TYPE: DNA
<213> ORGANISM: Zea mays
<220> FEATURE:
<221> NAME/KEY: misc_feature
<222> LOCATION: (116)..(116)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (491)..(495)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (612)..(627)
<223> OTHER INFORMATION: n is a, c, g, or t

<400> SEQUENCE: 27

```
cagaaaagga ggaggcatct gaagagattc attcgctgca taaaacgctc gatggaatga     60
tcgagcacaa agcagaatta gaaatacagg tagttacatg cttgtcaaat tttctnctta   120
attgtagctt caatatatgt tctcatatac atagcagtag aaagaaancc tgttgtttgt   180
ttaactaagt agaacaattt tcaggtatct tctactatac aagagcacga agaactgaag   240
agcaagtacc aaaatacaat ggaagagaaa cagacgttga gtgataaata tgaaaccnca   300
aagaaagagc tcgaggatgc aatagccaag ttggaggagg aaatgaatgt agacaagtca   360 gaaaagagt ctcacatctc aaaactggag cgacagatta cattatctga gataaagtac    420
atggaggagg taagtgtccc ctgttcatct ctctccaaac tatttgggat ttgacctggg    480
aatgatatct nnnnngtata acatatgtac tattttcaga taaagaccat gcaagtggag    540
acaactgaaa agaatgaagc actaacagcc aagatgcagg aacacacaga cctacagcat    600
gagaaagntg annnnnnnnn nnnnnnnc                                         628
```

<210> SEQ ID NO 28
<211> LENGTH: 734
<212> TYPE: DNA
<213> ORGANISM: Zea mays
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature

```
<222> LOCATION: (483)..(483)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (643)..(643)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (648)..(649)
<223> OTHER INFORMATION: n is a, c, g, or t
<220> FEATURE:
<221> NAME/KEY: misc_feature
<222> LOCATION: (651)..(653)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t
<220> FEATURE:
<221> NAME/KEY: misc_feature
<222> LOCATION: (659)..(662)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (677)..(678)
<223> OTHER INFORMATION: n is a, c, g, or t
<220> FEATURE:
<221> NAME/KEY: misc_feature
<222> LOCATION: (694)..(697)
<223> OTHER INFORMATION: n is a, c, g, or t
<220> FEATURE:
<221> NAME/KEY: misc_feature
<222> LOCATION: (699)..(701)
<223> OTHER INFORMATION: n is a, c, g, or t
<220> FEATURE:
<221> NAME/KEY: misc_feature
<222> LOCATION: (703)..(707)
<223> OTHER INFORMATION: n is a, c, g, or t
<220> FEATURE:
<221> NAME/KEY: misc_feature
<222> LOCATION: (709)..(711)
<223> OTHER INFORMATION: n is a, c, g, or t
<220> FEATURE:
<221> NAME/KEY: misc_feature
<222> LOCATION: (718)..(719)
<223> OTHER INFORMATION: n is a, c, g, or t
<220> FEATURE:
```

```
<221> NAME/KEY: misc_feature
<222> LOCATION: (726)..(733)
<223> OTHER INFORMATION: n is a, c, g, or t

<400> SEQUENCE: 28
cctgcagtgt agttgtaacc acaagatagg ctttccacat gcntaccttc caatgcatct    60
actaaagttg gagtgctcct attaaggaag tcacctaaac caagctgccc ttccttgcct   120
ttaccccatg taaacacttt cccatttgta gtcaccactg ctacatggga agaacctgat   180
gatatatgtc tgacaaactc gctcttaagt agtccttcaa cagcagaaac agttttacca   240
tctgcatggg ggttccctaa ttgcccatgc atcgaactgc cactagtaaa gaccacacca   300
gtaacagaga gagcaacagt gagtgccgtc ccgcaggaca cctgaataaa atcatagtct   360
gtgagtgaat caacacatgt tggtataagc ttcatctttt tgtcagcatg acccagcttc   420
ccccgatctg catcgcccca tgtgaacagc ttgcttcttg gtgaattgct cttgaaatca   480
ctnatcactt ccacaatggc agctgtgtgc catggcccac atgccacaca tttcactctt   540
gagcctttca aagactctac ttctttngnc cgggtagttc cttgtgtatc tnnatgacca   600
anaacaccaa atgtnccatc nccatatgtg tataactgac canannannt nnntanngnn   660
nngtgccaag naccacnngc aatcttcaca acannnntnn ngnnnnntnn nctaaacnnt   720
ttatgnnnnn nnna                                                     734

<210> SEQ ID NO 29
<211> LENGTH: 459
<212> TYPE: DNA
<213> ORGANISM: Zea mays
<220> FEATURE:
<221> NAME/KEY: misc_feature
<222> LOCATION: (44)..(44)
<223> OTHER INFORMATION: n is a, c, g, or t

<400> SEQUENCE: 29
cacagatctc caaaaacttt gtggcctcaa atcaattgga gtantgaatt cccactccct    60
tatctgttat cttctttctt gccagggttt ggtgcaggat cctcgcgttc cagggcagct   120
gttgccaggg ctgctccagc aatcaacaat tctcagactc ttgataatgc tcctccacat   180
cctgctgatg gagatgcccc tccacatgct gccgatggag gtgctcctcc acatgctgca   240
gatggagatg ctcctccaat gaacaatgaa gaaattgcaa accaagatga aattatgatt   300
ggtgaagtag ctgtagatga tgaagatgaa gacgcaaact ctcatccagt tccagccagg   360
gatgcgtcga tggaaagtga gcttgccaat gaactgaagg gggatgcctt ggatgactac   420
gatattgatg tcagtaacga aggacaggct atcgcagag                          459

<210> SEQ ID NO 30
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t

<400> SEQUENCE: 30
tacttaactt gcacaaccta gtcacattag aaaaaatatg gtacttgtgt tcagtgtccc    60
aacagcatgt caatcgacta gaatctacta ctttgtacca ntgctgcaca actagcgctg   120
```

```
cattatgtag actctattat ttacacacat aagagntaaa tttcaattaa ctatgaactc      180
cagctcgcaa tgcacagcac a                                               201
```

<210> SEQ ID NO 31
<211> LENGTH: 210
<212> TYPE: DNA
<213> ORGANISM: Zea mays
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (202)..(202)
<223> OTHER INFORMATION: n is a, c, g, or t

<400> SEQUENCE: 31

```
atggttatgg ctatgtacat tacatagaat ttggtacgta catgatcatc atctgcatga      60
ctgcattttg tgtatggcgt ttgtcagttn gcaatgacag ggtgttgatt tattctgtgc     120
cgtaagcatt ctatgtctca gctttcccat ggaactcaat caaaacagaa catacgattt     180
cagatagact gggtgtaact gncatttcc                                       210
```

<210> SEQ ID NO 32
<211> LENGTH: 995
<212> TYPE: DNA
<213> ORGANISM: Zea mays
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (961)..(968)
<223> OTHER INFORMATION: n is a, c, g, or t

<400> SEQUENCE: 32

```
ccttttatta atcagggatc ttcgaaatac aggttgctgg tggtgacggt acagcaagtt      60
ggctgcttgg agtagttagt gacctgaaac tatcacatcc acctcctgtt gctaccgtac     120
ctcttgggac tggaaacaac ctccctttt catttggatg ggtaagttaa cacctttgc       180 ttattttgag cacaccgaat tcttaattat gattaatatt ctacctctat gtgttttata    240
tgtctagaaa attttatgtt tttggtgcaa atggagaatg tagggtagag taaaaaaat     300 gattgttaga caaacatgat aaaactataa aagtttgcca cgagaaacac actatattta    360
ttagtgcatg ctaacaaaaa tgttatgact gagcatcagt ctcagttaaa aaaacataat    420
tttttgtttt aatatagaaa actagaagac ttgttattaa atttgtataa atgtataatg    480
ttgtttatat gtaattttc cagttaaaat tgcaatgttc tttagcagtt aggggcttgt    540
accaagtttt acaattaaaa aaaacaatat tctattttaa tctgactgca gggaaagaag    600
aatcccgcta ctgaccaggc agcagtgaaa tcattcctgg atcaagtaaa aggagcaaga    660
gaaatgaata tcgataggta ctgtcttgct tacaaaggat aaaagataat gttttgtcat    720
gcactgcatg agctcatcca tccatctcat atgatgaagt gttttatgct ctttttccaat    780 tattgtttta cttaacaaca ttagaacata tccttatgtt cagggtacga aagaaaacac    840
tcaattcagc ttctagttgt atttttctgt ntcagctggc atatcatcat gaggatgcga    900
attccacagg aaggcccatg tgatcctatt gctcccttag atcttccaca ttcgttgcat    960
nnnnnnnncc gcgtatcagc ttgtgactct ctcaa                               995
```

<210> SEQ ID NO 33
<211> LENGTH: 849
<212> TYPE: DNA
<213> ORGANISM: Zea mays
<220> FEATURE:
<221> NAME/KEY: misc_feature
<222> LOCATION: (460)..(460)
<223> OTHER INFORMATION: n is a, c, g, or t

<400> SEQUENCE: 33

| | | | | | |
|---|---|---|---|---|---|
| ttgacgtcct | gcttgttgca | ttgctacttg | tcagcattct | attgccacat | ggaacacttg | 60 |
| gatgcaagca | gaagtgagac | actattgcat | ttgtttgttt | ttttgagtgc | atcttctgtt | 120 |
| tatttcaaac | ttcagattag | ctgttatctg | caactagcta | ggaaggtact | cgcgagaaga | 180 |
| aaaaaaaata | atgaagctag | gaaggaaggg | tgtacgaata | ataccttcca | ggaaagggta | 240 |
| cggtcaactt | gaccagcaac | gtaggaagca | aggccggaat | catttgtctg | atacgtcaag | 300 |
| agatgtttgg | ttagaaaagt | ctgaagaaat | agatgcatct | ttatgtatag | cccaatgcca | 360 |
| agctcggctt | ccagctaacc | ttgtccatcg | tgccaagatc | cagcgcttgg | aagttttca | 420 |
| acaccagatg | tggaggtaag | gcgaacctgc | atggtttcan | agtacatatg | cagtgtgtat | 480 |
| aggactcctt | atagtgaaaa | aaaaaagaaa | cgttcgtccg | tgcagcattc | tgggttcagt | 540 |
| tcttagatta | gcacctgttc | ttaatgtcag | cttccctgcg | gccaagtatt | ggagtgtcta | 600 |
| cggtgagtgc | aatagccttg | aagccagcca | tctcagccct | tttcacgagt | tgccgtacga | 660 |
| tgttcctgtc | cttgtagacc | tgatggagac | gacgatacat | ggtataaggt | cagagtgtga | 720 |
| tgaacagaag | ataagcaacg | tttcttgtga | gttcatgaag | gaagataata | atgcatacat | 780 |
| agagctggaa | gaaacgtatg | cccggcccaa | ctgagttgac | ctcttcaacg | ctggaagtag | 840 |
| accatgagg | | | | | | 849 |

<210> SEQ ID NO 34
<211> LENGTH: 718
<212> TYPE: DNA
<213> ORGANISM: Zea mays
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (231)..(237)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t -continued

```
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (511)..(511)
<223> OTHER INFORMATION: n is a, c, g, or t
<220> FEATURE:
<221> NAME/KEY: misc_feature
<222> LOCATION: (553)..(554)
<223> OTHER INFORMATION: n is a, c, g, or t
<220> FEATURE:
<221> NAME/KEY: misc_feature
<222> LOCATION: (556)..(556)
<223> OTHER INFORMATION: n is a, c, g, or t
<220> FEATURE:
<221> NAME/KEY: misc_feature
<222> LOCATION: (582)..(583)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (606)..(607)
```

```
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (614)..(614)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (639)..(641)
<223> OTHER INFORMATION: n is a, c, g, or t
<220> FEATURE:
<221> NAME/KEY: misc_feature
<222> LOCATION: (650)..(652)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (667)..(668)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (676)..(686)
<223> OTHER INFORMATION: n is a, c, g, or t
<220> FEATURE:
<221> NAME/KEY: misc_feature
<222> LOCATION: (688)..(699)
<223> OTHER INFORMATION: n is a, c, g, or t
<220> FEATURE:
<221> NAME/KEY: misc_feature
<222> LOCATION: (704)..(716)
<223> OTHER INFORMATION: n is a, c, g, or t

<400> SEQUENCE: 34
cgtaacttgc gaanaacgaa cgagttttgc cacagcagga cgatccttgt accgtcgtcc    60
gcaagggttg taatttctca nggaccgtta cgacangatt gtatgtcagg ttttgacagt   120
ttgngccaat gcaattcttc taatgaaaaa gacaagtgca tgtgantggt tagcatctgc   180
ctatcgccta tcgggtatca tgtggagtcg tctggtatac cgtcctacac nnnnnnncnt   240
gagaacgaag cnaccttacc cccaacnatc accttgtagc gatccgaagt tgttcatctt   300
ngagtttcag ttctctaact ccatcgtagc taagcgtttc agcaatgngt caagaganan   360
atttaactat ttgtnaccgt taggaaggcc acatnttngt ttncttgttt tacntggcaa   420
ctgtacgatt tttnatcgna aacgctaact ggtctatttt attgatgtac catnttaaat   480
tagcatgtca cggtggatcn tagtcttttt nccggagaga cacctggaaa gtcatttta    540
ccttcgcatt ttnnantatt tagtgcgtta tgtgcaattt gnntagaatt ctatcatnta   600
gattgnnata tntnaatatt naatgcaata ctagtagtnn ngattttgn nnactnatt    660
gaagtannat gagntnnnnn nnnnnnannn nnnnnnnnnt gagnnnnnnn nnnnnnca      718

<210> SEQ ID NO 35
<211> LENGTH: 388
<212> TYPE: DNA
<213> ORGANISM: Zea mays
<220> FEATURE:
<221> NAME/KEY: misc_feature
```

-continued

<222> LOCATION: (225)..(225)
<223> OTHER INFORMATION: n is a, c, g, or t

<400> SEQUENCE: 35
ctcttttgct tggaacattt gtagaggaga agggataaga tcaacgagaa gctgaaagca      60
ttacaggagc ttcttccaaa ctgcaacaag gtaacatgca ttgcgtctta attttaatcc     120
gaccataccc cttctgctgt tctcttttc gtttgatctc agaatagctt gtttcagacc     180
gacaaagttt cgatgctaga cgaagcaatc gactacctaa aatcncttca gctacagctt     240
caggtactga atgaaatcat atcagataca caattgttgg ttacactaga catttattta     300 ttttatctt tctctcctgc atcctttcct gttttattta ttcagcctcc agatattatg     360
ggtgctatag tagatcatca cattgtca                                        388

<210> SEQ ID NO 36
<211> LENGTH: 437
<212> TYPE: DNA
<213> ORGANISM: Zea mays
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (200)..(200)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t

<400> SEQUENCE: 36
cgggcccgcg gtgggagtgn ccgacgccga cgtccgctcg acattcggcg ccttcgggga      60
ggtcgcagga gtccaggctg ccgacgacag cggcgcccgc atcatcgtcc ggttccacga     120
gcccgccgcc gcggaggccg ccatggctgc gctccacggg cgcccctgcg acctccttgc     180
gggtcgcgtg ctgcacatan ggtactcggt gcccgtgaag ccaaaggctc gncctggggg     240
ctctgtaccg gtggctcacg cggcatcgga gctcggaatc cccgggattt acatggttca     300
ggagttcgtg actgccgctg aggaacaggt tagccaattt tgagacatct ctgtttgttg     360
cccaaatttg aggttttttg ctaaatagcc ctgcttcgat gtgctgagtg gtactacatc     420
ttttgccagg agttant                                                    437

<210> SEQ ID NO 37
<211> LENGTH: 660
<212> TYPE: DNA
<213> ORGANISM: Zea mays
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (170)..(170)

```
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (570)..(571)
<223> OTHER INFORMATION: n is a, c, g, or t
<220> FEATURE:
<221> NAME/KEY: misc_feature
<222> LOCATION: (596)..(596)
<223> OTHER INFORMATION: n is a, c, g, or t
<220> FEATURE:
<221> NAME/KEY: misc_feature
<222> LOCATION: (608)..(612)
<223> OTHER INFORMATION: n is a, c, g, or t
<220> FEATURE:
<221> NAME/KEY: misc_feature
<222> LOCATION: (624)..(625)
<223> OTHER INFORMATION: n is a, c, g, or t
<220> FEATURE:
<221> NAME/KEY: misc_feature
<222> LOCATION: (637)..(645)
<223> OTHER INFORMATION: n is a, c, g, or t
<220> FEATURE:
<221> NAME/KEY: misc_feature
<222> LOCATION: (647)..(649)
<223> OTHER INFORMATION: n is a, c, g, or t
<220> FEATURE:
<221> NAME/KEY: misc_feature
<222> LOCATION: (651)..(653)
<223> OTHER INFORMATION: n is a, c, g, or t

<400> SEQUENCE: 37
ttttgcaagg accttttctg gtttacatgc tagaggaatc gagcctggtg ttctttatcc    60
agctgtctct gttgagcagt ttcacgaacc ccatgcttat aagtaacttc atgcttgcat   120
atctccttac atttaggtct nacttattca gtttatagan taaacanatn ttttaccat    180 tatcatatta anatttagct aaagtagaca acnatctttt gtacaggttg aatttcctat   240
caatcaaccg gtttgagagg aaaaagaatc ttgatcttgc catttcagca tttgctttgc   300
tccgttctgc tgcttggact ntacctggtg atgctctaca agaagcaaca ttaacagtgg   360
caggtgttta tattttattt ttccttctag ttgcatgttc aatgttacaa cacnccggt    420 tttaaaccat atgaaatatt gactgctgat ttcctacnat gccnattatt taggtggcta   480
tgataagcgt ctcaaggaaa atgttgaata ccttgaggaa ctcaaaagac tcgcattgac   540
ggaaggggtt tctggacagg ttaantttgn nacatcttgc tcaacatctg aaaganacga   600
```

```
gcttctcnnn nnctgcctct gcgnnttata cactccnnnn nnnnntnnnt nnngcttaca    660
```

<210> SEQ ID NO 38
<211> LENGTH: 201
<212> TYPE: DNA
<213> ORGANISM: Zea mays
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t

<400> SEQUENCE: 38

```
gagcaagcag cacctcttac ccgggagcag tttaagaagc atgacanaat ggtcgaatct     60
cctgctccag ttaccgctgn gggttcggaa tgctgcatca nactcaatga acaggagcaa    120
gtagcacctc ctaccaagct gcaatcgaag aagcgtggta ganatgttaa agatcctgct    180
gcagntacta cagggctttg                                                 201
```

<210> SEQ ID NO 39
<211> LENGTH: 201
<212> TYPE: DNA
<213> ORGANISM: Zea mays
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 39

```
gaaaaaaatg gcccatctaa aatataaaga taatattcaa ctatgattca cgaacaatgn     60
tccatttggc cagcgcacac agaatgcaag tgaccttttc ncaagccatg cacataaagc    120
cgaaacaact atgcttttta gaaaaaggag aaattgagga agatgacagt agccatgaga    180
ctcggcatgt actactcctt g                                               201
```

<210> SEQ ID NO 40
<211> LENGTH: 1028
<212> TYPE: DNA
<213> ORGANISM: Zea mays
<220> FEATURE:
<221> NAME/KEY: misc_feature
<222> LOCATION: (574)..(574)
<223> OTHER INFORMATION: n is a, c, g, or t
<220> FEATURE:
<221> NAME/KEY: misc_feature
<222> LOCATION: (960)..(962)
<223> OTHER INFORMATION: n is a, c, g, or t
<220> FEATURE:
<221> NAME/KEY: misc_feature
<222> LOCATION: (994)..(994)

```
<223> OTHER INFORMATION: n is a, c, g, or t
<220> FEATURE:
<221> NAME/KEY: misc_feature
<222> LOCATION: (997)..(1003)
<223> OTHER INFORMATION: n is a, c, g, or t

<400> SEQUENCE: 40
caatccaata ccaaatcaga aggaatatta gaaaaggctt cacttgttaa atatgtcaag      60
gcattcatgt actgcaagaa tagagggggc agagaatccc atcagatagg tgctgtagaa     120
tgtggataaa gcctgaacaa gatggtctac ttgcaaaact gaagcagaga agtgtaaaa     180
tatacagttc agaccactga ggctaaaaga acaaatctac attgggtaaa tgtcaacatt    240
cagattttaa aacataccat tttaacattg ttatggcagt ccagaagtgg tctacgagca   300
accagattgt aagccaaaca tccaaagcta acatatcac aagcagagcc aactttagaa   360
tctctacttt ggaccaattc tggtgcagta tagttcaacg atggttgaag aggtaaagct   420
gtatcctcga catcatagtc ctagaaagaa acaagcaga taaattgtta acaggtcagg    480
gcattggaag caacaaaaaa aatcacaaaa cgtatcttga agacacaaat cacagaagat   540
gtcaccaaag tacttaggaa tgggtatgat gaancgctaa atatgcttag ttgaccattg   600
ataacttaac aatgtagcgg tctaataatg actaacatag gttcgtggtg cacatcgtat   660
atgccattac aaatcccagc agtagcaatg tgctaaacac aatcgccagt tcgccacatc   720
acagtagtgg tatattctta actttatat gaaaagatca gttcaagaca agaagaaact    780
ctgccagaaa aatatgtatc atgcaaaact gtgtgacaat ttagaaatta aatgattgca   840
aaaaaagaa caatataagt tcagtggaat attttctgtt acagcaaact tcaaagggat    900
aatacagatt agtaatattc ccaaaatatg gtagaagaat ctgcaaatta aagccaccan   960
nntgacaaac taaatgtata tcacttacta accnaannnn nnnatagttg tgatgaagtc   1020
aaactcaa                                                            1028

<210> SEQ ID NO 41
<211> LENGTH: 347
<212> TYPE: DNA
<213> ORGANISM: Zea mays
<220> FEATURE:
<221> NAME/KEY: misc_feature
<222> LOCATION: (230)..(230)
<223> OTHER INFORMATION: n is a, c, g, or t

<400> SEQUENCE: 41
agttatcaca ttagcttttt ccggtggcct gtttggtaca gcttataagc tgttcatggc      60
caaactgtac gcttttctgc aacttattct ggctgcgctt agtcccacca tcccatttgt     120
gctaaaaagt agatgggtca aacctactta tttttgactgt gttttactcc atttgtgcag    180
cttctctacg aagcgcttcc tatataccct agaagaacga ccgttgtgcn agcaagactg    240
cgatgcaagc gagctttctg atcctttaaa tcctaatcca actgtaggtc acatttaaca    300
cttaaacctc ttcaccacca gcttacgcag ctttttttcaa aaaaaaa                 347

<210> SEQ ID NO 42
<211> LENGTH: 873
<212> TYPE: DNA
<213> ORGANISM: Zea mays
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
```

```
<222> LOCATION: (106)..(106)
<223> OTHER INFORMATION: n is a, c, g, or t
<220> FEATURE:
<221> NAME/KEY: misc_feature
<222> LOCATION: (167)..(167)
<223> OTHER INFORMATION: n is a, c, g, or t
<220> FEATURE:
<221> NAME/KEY: misc_feature
<222> LOCATION: (170)..(171)
<223> OTHER INFORMATION: n is a, c, g, or t
<220> FEATURE:
<221> NAME/KEY: misc_feature
<222> LOCATION: (246)..(253)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (305)..(311)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (343)..(343)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t

<400> SEQUENCE: 42 cgtgtttttcc agttgacgtt cacggaagtc ttgtgtctttt tggatagact gatagtgata    60
```

```
ggcacgcata acngtaaaca tattctgtgc tccgtgctca tatgancact ttaaatctag    120
tgtatacgtg agtaatctag ctctgatatc atctcagcct tgatagncan ncagagagta    180
aatgaacacg gaataagatc ccgcataact acctagccac agacactgct gctcctggcg    240
agtggnnnnn nnncgaacaa ggtttcccat cttttngngc ntgccatacn tggattttt     300 ttaannnnnn ntgtatcnaa attgaanttg gaagtgtata ctntcccagt cgcacaaaga    360
gtgttctttc gacttttgag aagtngnnnn nnnnnnnnnn nnnnnnnnnn nnnnnnnnnn    420
nnnnnnnnnn nnnnnnnnnn nctncntcnn tcctaaaata ggttngttta gcacttantt    480
tttatgttta tattcaaata gatgatgacg aatttacaaa tatatatcaa acatatgcat    540
taagtataca ttaagtctag tcaacagaga gagtaagtat tattataata tttgctaaat    600
attttttcat aataaacatt ttttagatac aaaggttgat aatacgtttt ctataaatct    660
agtcaaacta aacaaagttt gacctgaaca taaccctaag tgacactttt ttggtgtaac    720
gctagctaga gcaccaacag cttagcaatg cttgcagtga catgttttta tttcatttct    780
tttcttgtat ccctgttcat cttcaccatt tgcacttgtt ggatgatagg cattcaatga    840
tgcagatgtg ccttgctaga acatcatgta cta                                 873
```

<210> SEQ ID NO 43
<211> LENGTH: 710
<212> TYPE: DNA
<213> ORGANISM: Zea mays
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (539)..(545)
<223> OTHER INFORMATION: n is a, c, g, or t
<220> FEATURE:
<221> NAME/KEY: misc_feature
<222> LOCATION: (547)..(552)
<223> OTHER INFORMATION: n is a, c, g, or t
<220> FEATURE:
<221> NAME/KEY: misc_feature
<222> LOCATION: (559)..(570)
<223> OTHER INFORMATION: n is a, c, g, or t
<220> FEATURE:
<221> NAME/KEY: misc_feature
<222> LOCATION: (583)..(584)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (592)..(593)
<223> OTHER INFORMATION: n is a, c, g, or t
<220> FEATURE:
<221> NAME/KEY: misc_feature
<222> LOCATION: (602)..(605)
<223> OTHER INFORMATION: n is a, c, g, or t
<220> FEATURE:
<221> NAME/KEY: misc_feature
<222> LOCATION: (610)..(611)
<223> OTHER INFORMATION: n is a, c, g, or t
<220> FEATURE:
<221> NAME/KEY: misc_feature
<222> LOCATION: (621)..(627)
<223> OTHER INFORMATION: n is a, c, g, or t
<220> FEATURE:
<221> NAME/KEY: misc_feature

```
<222> LOCATION: (629)..(630)
<223> OTHER INFORMATION: n is a, c, g, or t
<220> FEATURE:
<221> NAME/KEY: misc_feature
<222> LOCATION: (632)..(642)
<223> OTHER INFORMATION: n is a, c, g, or t
<220> FEATURE:
<221> NAME/KEY: misc_feature
<222> LOCATION: (646)..(658)
<223> OTHER INFORMATION: n is a, c, g, or t
<220> FEATURE:
<221> NAME/KEY: misc_feature
<222> LOCATION: (664)..(670)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (674)..(707)
<223> OTHER INFORMATION: n is a, c, g, or t

<400> SEQUENCE: 43
cccctaccaa atcgagcaca gctcagaaga ggcagggag gatcactctc ctaccancca      60
aaagtcacct cgacactgga cgtgatacaa gagacacaaa acatgggcca gaagacacca    120
tgcatcagac agttctgaga acttattcaa cagcaaaagt catcttcgga tttgttggct   180
tcctcgttcc accatccttt ttggcatctt ttcctgtaga acagaccacg aatccaacca   240
aaagaagcaa gcataaatca catcagtagg gtcataaaag accttgttgt taaagcacac   300
atcattccta aacttccaaa tggcccagag aatggctcct atgcctagaa caatcanatt   360
cctcgtggtt ttcttataaa tgttcatcca gtcctcaaaa agagaatcca ggttttgagg   420
acatctcttc acatccaggg caacctgaag aactctccac acaaaagtgg ccactgggca   480
attgagaaaa aggtgattgg tggattccaa acaccacag aaacaacaat cagtcaacnn    540
nnnnnannnn nnttttcnn nnnnnnnnnn gagataattt ttnntctnca gnncaagcca   600
cnnnnaaacn naaattttg nnnnnnncnn annnnnnnnn nnaacnnnnn nnnnnnnta    660 tgannnnnnn tngnnnnnnn nnnnnnnnnn nnnnnnnnnn nnnnnnnatt              710

<210> SEQ ID NO 44
<211> LENGTH: 254
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 44
agggtagtat atgtgcattc atcgttttc attagccttg attagnccaa agtgatagtt     60
tatgcttggt catcgagagt ttggtgatca gacgatgaag attgtgagtg gcacaactta   120
agaggtaaac agttgtgtga ttcaacatag tagagtgaca aatgatcgac tcatagagag   180
ccctcgtatg agacgtgagc gacactcctt cataggtgtt ctaataagga ttagttagaa   240
gtgtcaactc ttga                                                     254

<210> SEQ ID NO 45
<211> LENGTH: 710
<212> TYPE: DNA
<213> ORGANISM: Zea mays
<220> FEATURE:
<221> NAME/KEY: misc_feature
<222> LOCATION: (132)..(132)
```

-continued

```
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (208)..(209)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (612)..(616)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (649)..(656)
<223> OTHER INFORMATION: n is a, c, g, or t
<220> FEATURE:
<221> NAME/KEY: misc_feature
<222> LOCATION: (661)..(684)
<223> OTHER INFORMATION: n is a, c, g, or t
<220> FEATURE:
<221> NAME/KEY: misc_feature
```

```
<222> LOCATION: (687)..(695)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (701)..(708)
<223> OTHER INFORMATION: n is a, c, g, or t

<400> SEQUENCE: 45
ctcatgtatg cattcgatgt agttccctga ggtaaatgac cacaccctga cagaatcttc      60
actgacagac gccagatagt tgcccgcggc atcccaacat actgactgaa taatctgtac     120
gtggccctac anaaaaaaca caagccnaaa ttacagagta catcgagaat agtgcagagt     180
aaatgcaaan aacatacagt gaagttanna cttagaatag ccgctaagtt gcatacctac     240
acttancgca atttaggaat gacatggacn tcaaggaact gattataatt caggaaagaa     300
acaaaatttc agcctggatg gtgatgagct gatcaaatgc tcattatacc acaagagttc     360
tcatcatacc acaataangt ataaacntac actcgtntgt atgttgtatc tcaataatct     420
agtactcnct ccattccaaa ttataanana attttgcttt tctagttata ttacttttac     480
tatatatcta gacatagtgc gtatctaagg gggtntntta ttgcactaga gcagtagagc     540
taatagttag ttggctaaaa aatagctagt ggaattagct agataacaaa tatctagcta     600
actaatagct annnnnctaa aatagctcat anntaaacta nnagctngnn nnnnnngata     660
nnnnnnnnnn nnnnnnnnnn nnnctnnnn nnnnnagtnc nnnnnnnnat                710

<210> SEQ ID NO 46
<211> LENGTH: 1793
<212> TYPE: DNA
<213> ORGANISM: Zea mays
<220> FEATURE:
<221> NAME/KEY: misc_feature
<222> LOCATION: (1440)..(1440)
<223> OTHER INFORMATION: n is a, c, g, or t

<400> SEQUENCE: 46
ttggtgtcgc tcgccatatc cccttttccc cctcccttc gtctcccgac tcctgcgatc       60
cgccccacct gaaccctact ccacgtcgcc tcgcctcgcc tcgccggttg ggttgtggct     120
gagccgatct gacccgatcg ggtgggtcct tgcgccgccg ctgcgtgggc tcatctcggt     180
cgcccgcctg ctcggctcga tcggccgggg acggcggcgg ctagatctgc gatggagggc     240
aacaaggacg acgcggccaa gtgcctgcgc atcggcaagg gcgcgctcga agccggggac     300
cgcgcgcgcg ccatcaaatt tatgtccaag gcaaagcgcc tcgacccctc gctacccatc     360
gatgacctgc tcacctccct tctcaacgcg caagacgact cccggcttc ctcatcatca     420 tcgccgcctc caccaccgca aactgccgca gcagggcat cggaggcagc tgaggctgat     480
gggctgagag agaggaagca aagggcaag aagagggagg aggaggaggc gactcctgct     540
gccagggagt acaccgcgga gcagctcgag gttgtgcgcc aggtcaagaa gcacaccagg     600
gactactacc agatcctcgg cctggaaaag gactgcagtg tcgaggacgt gcgcaaggcc     660
taccggaagc tctcgctcaa ggtgcacccc gacaagaaca aggcccctgg cgcagaggac     720
gccttcaagg ccgtctccaa ggccttccag tgcctgagtg atgcggagag ccgcaagcgc     780
tacgaccttg ttggctcgga tgagccagta gcacaccaca ggagggcctc cactgcccgc     840
gcatacaatg ggttctatga ggatgacttt gacccagatg agatattcag aaacttcttc     900
```

-continued

```
tttggcggta tggcgcctgc aaccaccagg cagtttggac agtttggaac tttccatttt    960
aggactggtg ggatgcatgc ccatgcccat gcccaacaaa actctggtgg ctcaactgtc   1020
aggatgctta ttcagctgtt gcctgtccta ctgctgctgt tgctcaactt cctgccatcc   1080
tctgagcctg tctactcgct gtcccgttca taccctttatg agcataagtt ccaaaccccca  1140 cgtggagttg catactatgt caagatgtct aatttcgagg agcagtatcc acaccaaagc   1200
actgagcgag cgacgctgga gcggcatgtt gagagggatt attactccat aatcacacag   1260
aattgcaggg ctgagctgca gcgtcgccaa tgggggctgt cataccagac accacattgt   1320
gatatgctta aaaattttga ggctgcagca aagtaataac tcatccaatt ctgtaaggtt   1380
gacatgggga gagagactgc tggccactca tgtaaaggcg ctgccttagc cgccagcttn   1440
aagtttgagg ggacatttta gtttggctta gtagtaaatt ttgtggaata agtgcctttg   1500
ataactatac accactgtcc agatgctccc tcttagtatt ggcaaggagt gcgttaatta   1560
gttacttcaa aaagatatgc aagcttcata ggggttgatc acatgcaaac cagtgtatgt   1620
atatgaagta tatctatctc attcttttaa cttttttgaa gtgaagactg tagttaaaac   1680
agaaatgcaa ctataacaca aatgtgatat tcattttata ttaaaaaaag aaaaaaaaaa   1740
tccgacgggg cgcccggtac cccgatcatc ggacatcatt ccgttggtat tgg          1793
```

```
<210> SEQ ID NO 47
<211> LENGTH: 551
<212> TYPE: DNA
<213> ORGANISM: Zea mays
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t

<400> SEQUENCE: 47
```

```
agatatgaag gtccggcaaa aaagttgccc tgggttgcaa ataaggctgc tgctgcacca    60
tcggatgaat cggccctaaa ccatcagnta ctgtgggttg agccatgcta ccatcagagc   120
ttcttgtact gctgaacagc cagtcttgac cacccaaatc tgaaccttca ttctccatca   180
atagcggatt ccaggtaaca aacagatctc tgaacttctt attttttcttc tcagtttttgt 240 ggattttctt ccgatctgaa cgggagagct tagcttcctt cccttgatct gcttccacag   300
tccttccaga gaacaaggc tcttcttttg gcaaagagnt gataggctcc cgctgtttag    360
gaacaggcaa gtccttgggt ttctgcaaaa caggaggatg tggagcttgt ggcaggcaaa   420
cagcagatcc catttccttc tgtgacacct tcgcctgagg atcaactctc tgtgacacca   480
tggaaggtgg atgctnaatt ctctgttgcg tcttaacagg tggaggacaa aatcttcggg   540
tcactctagc a                                                        551
```

```
<210> SEQ ID NO 48
<211> LENGTH: 580
<212> TYPE: DNA
<213> ORGANISM: Zea mays
<220> FEATURE:
<221> NAME/KEY: misc_feature
<222> LOCATION: (166)..(166)
<223> OTHER INFORMATION: n is a, c, g, or t
```

<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (540)..(542)
<223> OTHER INFORMATION: n is a, c, g, or t
<220> FEATURE:
<221> NAME/KEY: misc_feature
<222> LOCATION: (544)..(544)
<223> OTHER INFORMATION: n is a, c, g, or t
<220> FEATURE:
<221> NAME/KEY: misc_feature
<222> LOCATION: (546)..(548)
<223> OTHER INFORMATION: n is a, c, g, or t
<220> FEATURE:
<221> NAME/KEY: misc_feature
<222> LOCATION: (559)..(560)
<223> OTHER INFORMATION: n is a, c, g, or t
<220> FEATURE:
<221> NAME/KEY: misc_feature
<222> LOCATION: (565)..(574)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t

<400> SEQUENCE: 48

```
taccggaatg ctccaaggtg aggagctctc acaagcgtac gccagtggag atgtatttgc    60
aatgccttca gaatccgaga ccctcgggca agtagtgctg gagtccatgg cttctggagt   120
cccagtcgtt gctgctcgtg ctggagggat acctgatata ataccnaagg acaaggaggg   180
taagacaagc tttctgttta cacccggaga tctcgatgag tgtgtgagga agatagagca   240
gctcctcagt tcaaaagatc tcagggaaac cattggaatg ctgccagag aagagatgga    300
gaagtgtgac tggaggncag cctcgaagaa aatccgcaac gagcactaca gcaccgcnat   360
atcgtactgg cggaagaaga tgggcaagac taacnagncc tccttgtttc nggattcttc   420
tgtcgctgcc ctctccaact agttgctgtt aataactaaa gaatttgtac attgtaccca   480
aacagcttgc gagttttgtg tggctagctg cattcaaatg tccacagtct gactgactan   540
nncntnnntt cgattcatnn acatnnnnnn nnnncttang                         580
```

<210> SEQ ID NO 49
<211> LENGTH: 811
<212> TYPE: DNA
<213> ORGANISM: Zea mays
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (70)..(70)

```
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (425)..(428)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (575)..(575)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t

<400> SEQUENCE: 49
cagcgcaatg agaggattga gngcctctgc gtctaggttt tgctttgtgc acaagcgttc      60
agaaccgaan gacacggcat gcacgctgtn caggtggtca tttcgccgcc gagcatgaac     120
agngcgcggc tgccatggac atggtcagtc tctggcaaag gttacgggtt tgctcgctgt     180
acaacaagcc gccatttcat tccgactagt aagaaaaata ttttcatggc gcggctctgg     240
ctgctcttgt tacattacta ttgctacatc aggacgccaa aaagaagaaa aaaacaaac     300 agaaaggtga aaccaggacg gccttcttcc aaggtggtgc ctgggacaca aaacactccc     360
ttttttctct ctcccgaaaa ccgggactcg acgtttacat tcaaaactgc gcnaaaaaaa     420
aaaannnnct gnccattcat ggtacttaat tggnaaagag atcctctact tgtttgaaaa     480
tctaacctag cnctgatggt ctttgccgtt cagcggatca tacctaatct tacagtcaga     540
aagcncctcc tcgaatatnt atctgcncgt tgaanacggt aggattagga atcggggcgt     600
cagtcgcagc aaattttcca cacaaaaaaa aaactatttg agaaaacacn ntatgcaga     660 acaacagaag cagtgtccca ggcaccacca ggggcacaga aacacatggc aagaggagtc    720
```

```
acccacctgt tagctagtac aaaacatgcc gaccgatgga accttgggag aaatgaactt    780
cacccagcca gagccagcca tcagaaggtg a                                   811

<210> SEQ ID NO 50
<211> LENGTH: 679
<212> TYPE: DNA
<213> ORGANISM: Zea mays
<220> FEATURE:
<221> NAME/KEY: misc_feature
<222> LOCATION: (103)..(105)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (567)..(569)
<223> OTHER INFORMATION: n is a, c, g, or t
<220> FEATURE:
<221> NAME/KEY: misc_feature
<222> LOCATION: (573)..(575)
<223> OTHER INFORMATION: n is a, c, g, or t
<220> FEATURE:
<221> NAME/KEY: misc_feature
<222> LOCATION: (584)..(586)
<223> OTHER INFORMATION: n is a, c, g, or t
<220> FEATURE:
<221> NAME/KEY: misc_feature
<222> LOCATION: (608)..(620)
<223> OTHER INFORMATION: n is a, c, g, or t
<220> FEATURE:
<221> NAME/KEY: misc_feature
<222> LOCATION: (641)..(646)
<223> OTHER INFORMATION: n is a, c, g, or t
<220> FEATURE:
<221> NAME/KEY: misc_feature
<222> LOCATION: (649)..(651)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (658)..(664)
<223> OTHER INFORMATION: n is a, c, g, or t
<220> FEATURE:
<221> NAME/KEY: misc_feature
<222> LOCATION: (667)..(676)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t

<400> SEQUENCE: 50
tgctgttgaa tgtgtctggt ttgtatctct aatttctgat ttcatgaatt ggtttacatg     60
tcttacgaac ctaacaccct ttcactggtt tgccattatg ttnnnattga tatagcacat   120
gtgtctttca tataatcttt gctgaacatt gctcttgacc aacatggtta acaggtctga   180
cggggaaatg gtattcgtgg acgataagca gttgaaagct aaggagcccc tggtggtatg   240
acctcattgt tttctcattt cacataatga agtaaaaatg gaatgacgcc acaacaatta   300
ttattctggt ttgcagctta ttgattacta tgagcaacac cttcgctana accccacctc   360
gtgataagga tgcattgacg ctgctgggtt tcagttgcat gtgctgcacc tatgtttgga   420
```

```
acaaatggaa atgtatttaa atgtagcatt ttttgtgcta gatgcatttg tagtattatt    480
tgagtaagta gataattagt aagtagccaa tgctgagtgc aagtgaaaca tgatagcatg    540
gtttgtcaaa ctaactgctc gatattnnna ctnnnttcaa attnnnttat taatcgtgat    600
aatcatgnnn nnnnnnnnnn gtcgatttgg accaatagtg nnnnnncgnn nangtnannn    660
nnnnaannnn nnnnnntna                                                 679
```

```
<210> SEQ ID NO 51
<211> LENGTH: 640
<212> TYPE: DNA
<213> ORGANISM: Zea mays
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (280)..(282)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (500)..(504)
<223> OTHER INFORMATION: n is a, c, g, or t
<220> FEATURE:
<221> NAME/KEY: misc_feature
<222> LOCATION: (513)..(514)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (539)..(548)
<223> OTHER INFORMATION: n is a, c, g, or t
<220> FEATURE:
<221> NAME/KEY: misc_feature
<222> LOCATION: (551)..(554)
<223> OTHER INFORMATION: n is a, c, g, or t
<220> FEATURE:
<221> NAME/KEY: misc_feature
<222> LOCATION: (569)..(574)
<223> OTHER INFORMATION: n is a, c, g, or t
```

```
<220> FEATURE:
<221> NAME/KEY: misc_feature
<222> LOCATION: (577)..(582)
<223> OTHER INFORMATION: n is a, c, g, or t
<220> FEATURE:
<221> NAME/KEY: misc_feature
<222> LOCATION: (584)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (629)..(633)
<223> OTHER INFORMATION: n is a, c, g, or t

<400> SEQUENCE: 51
ctcggacgga ggaanctcca gtcgacagca angactactg gggcgcgcac tcacttccac      60
ggccactggg tctcggactc accgtgaagc cacngcaatc tgatggacat ggactaggtt     120
aacatctcct nagcctgaaa cgtgacagct gacatgggtn agagtgaaaa naaaattagt     180
ttaggcatta ggggacacga cgcagaacgg ggtggctcga ggccaagcgg gcggcggacc     240
cgagcggata aggacgagct cggncctcaa ctgtcgctgn nntggcgcat gacacaaaca     300
caaagcatng tttcctgttg gtaatttacc accactagcg ctagcctacn actggtatgt     360
tttttgtttt tgtttttttt tgcattggat cgtagaatta taaactttat aatatgccat     420
aaaagctgaa ggttgcagta ttagtttaaa ttattctatt tgttaattta aaacgttgtc     480
gcaggctcgc agctgctgtn nnntctgct ttnncctccc ccggtctaca aagaccncnn      540
nnnnnnnntc nnnnatgctc ttcttcctnn nnnngcnnnn nnannnnnnn nnnnnnnnnn     600
nnnnnnnnnn nnnnnnnnnn nnnccntnn nnnctacata                            640

<210> SEQ ID NO 52
<211> LENGTH: 18
<212> TYPE: DNA
<213> ORGANISM: Zea mays

<400> SEQUENCE: 52
cgtcaccatc gccatcgt                                                    18

<210> SEQ ID NO 53
<211> LENGTH: 17
<212> TYPE: DNA
<213> ORGANISM: Zea mays

<400> SEQUENCE: 53
ctggacgcgt ggacgat                                                     17

<210> SEQ ID NO 54
<211> LENGTH: 21
<212> TYPE: DNA
<213> ORGANISM: Zea mays

<400> SEQUENCE: 54
tgcaggttgc gtattttgtg a                                                21

<210> SEQ ID NO 55
<211> LENGTH: 25
<212> TYPE: DNA
<213> ORGANISM: Zea mays

<400> SEQUENCE: 55
```

-continued agcccactga atatggaatc attag    25

<210> SEQ ID NO 56
<211> LENGTH: 23
<212> TYPE: DNA
<213> ORGANISM: Zea mays

<400> SEQUENCE: 56
catgggaagc tgagttcaga tct    23

<210> SEQ ID NO 57
<211> LENGTH: 21
<212> TYPE: DNA
<213> ORGANISM: Zea mays

<400> SEQUENCE: 57
cctcagcatt tttggcaagt g    21

<210> SEQ ID NO 58
<211> LENGTH: 24
<212> TYPE: DNA
<213> ORGANISM: Zea mays

<400> SEQUENCE: 58
ctgctcaagt ttgaagatgt cgtt    24

<210> SEQ ID NO 59
<211> LENGTH: 22
<212> TYPE: DNA
<213> ORGANISM: Zea mays

<400> SEQUENCE: 59
taaaaattgc acgagcaaaa cg    22

<210> SEQ ID NO 60
<211> LENGTH: 24
<212> TYPE: DNA
<213> ORGANISM: Zea mays

<400> SEQUENCE: 60
tggaggtgca gagtctatct gatc    24

<210> SEQ ID NO 61
<211> LENGTH: 25
<212> TYPE: DNA
<213> ORGANISM: Zea mays

<400> SEQUENCE: 61
cttcatcttt caacacaacc tacga    25

<210> SEQ ID NO 62
<211> LENGTH: 21
<212> TYPE: DNA
<213> ORGANISM: Zea mays

<400> SEQUENCE: 62
cggaggttcc actgcaaaga g    21

<210> SEQ ID NO 63
<211> LENGTH: 24
<212> TYPE: DNA
<213> ORGANISM: Zea mays

<400> SEQUENCE: 63

```
cgagagactg gataagttgt gtga                                          24

<210> SEQ ID NO 64
<211> LENGTH: 15
<212> TYPE: DNA
<213> ORGANISM: Zea mays

<400> SEQUENCE: 64
ttgccccgcc ttgct                                                    15

<210> SEQ ID NO 65
<211> LENGTH: 27
<212> TYPE: DNA
<213> ORGANISM: Zea mays

<400> SEQUENCE: 65
gatctattga atcgaaccct tgtctga                                       27

<210> SEQ ID NO 66
<211> LENGTH: 23
<212> TYPE: DNA
<213> ORGANISM: Zea mays

<400> SEQUENCE: 66
gggttttgac gtgttggatt tgt                                           23

<210> SEQ ID NO 67
<211> LENGTH: 16
<212> TYPE: DNA
<213> ORGANISM: Zea mays

<400> SEQUENCE: 67
cggccgagct gcaaga                                                   16

<210> SEQ ID NO 68
<211> LENGTH: 23
<212> TYPE: DNA
<213> ORGANISM: Zea mays

<400> SEQUENCE: 68
gatcagctga gagagcctag cta                                           23

<210> SEQ ID NO 69
<211> LENGTH: 24
<212> TYPE: DNA
<213> ORGANISM: Zea mays

<400> SEQUENCE: 69
cgctgatagt tagaggcctc tttc                                          24

<210> SEQ ID NO 70
<211> LENGTH: 21
<212> TYPE: DNA
<213> ORGANISM: Zea mays

<400> SEQUENCE: 70
ccctgttagt ttgccaacca a                                             21

<210> SEQ ID NO 71
<211> LENGTH: 22
<212> TYPE: DNA
<213> ORGANISM: Zea mays
```

```
<400> SEQUENCE: 71
ccaaacacgc ttgtgcaact aa                                              22

<210> SEQ ID NO 72
<211> LENGTH: 21
<212> TYPE: DNA
<213> ORGANISM: Zea mays

<400> SEQUENCE: 72
ccattagcga cgttgctcaa g                                               21

<210> SEQ ID NO 73
<211> LENGTH: 24
<212> TYPE: DNA
<213> ORGANISM: Zea mays

<400> SEQUENCE: 73
gcgaagcaaa tcacataggt acca                                            24

<210> SEQ ID NO 74
<211> LENGTH: 25
<212> TYPE: DNA
<213> ORGANISM: Zea mays

<400> SEQUENCE: 74
acgtgttgtc tcaccctatc tctat                                           25

<210> SEQ ID NO 75
<211> LENGTH: 25
<212> TYPE: DNA
<213> ORGANISM: Zea mays

<400> SEQUENCE: 75
ctatctgacg actgcttgct ttcta                                           25

<210> SEQ ID NO 76
<211> LENGTH: 21
<212> TYPE: DNA
<213> ORGANISM: Zea mays

<400> SEQUENCE: 76
cgtcgtcttc aagctctcga a                                               21

<210> SEQ ID NO 77
<211> LENGTH: 25
<212> TYPE: DNA
<213> ORGANISM: Zea mays

<400> SEQUENCE: 77
ggttgccaat cagtacctat ttcag                                           25

<210> SEQ ID NO 78
<211> LENGTH: 24
<212> TYPE: DNA
<213> ORGANISM: Zea mays

<400> SEQUENCE: 78
ggaagagaaa cagacgttga gtga                                            24

<210> SEQ ID NO 79
<211> LENGTH: 21
<212> TYPE: DNA
<213> ORGANISM: Zea mays
```

```
<400> SEQUENCE: 79
gcttgcttct tggtgaattg c                                            21

<210> SEQ ID NO 80
<211> LENGTH: 25
<212> TYPE: DNA
<213> ORGANISM: Zea mays

<400> SEQUENCE: 80
ctccaaaaac tttgtggcct caaat                                        25

<210> SEQ ID NO 81
<211> LENGTH: 25
<212> TYPE: DNA
<213> ORGANISM: Zea mays

<400> SEQUENCE: 81
ccaacagcat gtcaatcgac tagaa                                        25

<210> SEQ ID NO 82
<211> LENGTH: 23
<212> TYPE: DNA
<213> ORGANISM: Zea mays

<400> SEQUENCE: 82
gcatgactgc attttgtgta tgg                                          23

<210> SEQ ID NO 83
<211> LENGTH: 25
<212> TYPE: DNA
<213> ORGANISM: Zea mays

<400> SEQUENCE: 83
ttcagggtac gaaagaaaac actca                                        25

<210> SEQ ID NO 84
<211> LENGTH: 23
<212> TYPE: DNA
<213> ORGANISM: Zea mays

<400> SEQUENCE: 84
caacaccaga tgtggaggta agg                                          23

<210> SEQ ID NO 85
<211> LENGTH: 24
<212> TYPE: DNA
<213> ORGANISM: Zea mays

<400> SEQUENCE: 85
ggagtcgtct ggtataccgt ccta                                         24

<210> SEQ ID NO 86
<211> LENGTH: 23
<212> TYPE: DNA
<213> ORGANISM: Zea mays

<400> SEQUENCE: 86
ccgacaaagt ttcgatgcta gac                                          23

<210> SEQ ID NO 87
<211> LENGTH: 18
<212> TYPE: DNA
```

<213> ORGANISM: Zea mays

<400> SEQUENCE: 87
ggtcgcgtgc tgcacata                                         18

<210> SEQ ID NO 88
<211> LENGTH: 21
<212> TYPE: DNA
<213> ORGANISM: Zea mays

<400> SEQUENCE: 88
catttgcttt gctccgttct g                                     21

<210> SEQ ID NO 89
<211> LENGTH: 22
<212> TYPE: DNA
<213> ORGANISM: Zea mays

<400> SEQUENCE: 89
cgaatctcct gctccagtta cc                                    22

<210> SEQ ID NO 90
<211> LENGTH: 19
<212> TYPE: DNA
<213> ORGANISM: Zea mays

<400> SEQUENCE: 90
cagcgcacac agaatgcaa                                        19

<210> SEQ ID NO 91
<211> LENGTH: 26
<212> TYPE: DNA
<213> ORGANISM: Zea mays

<400> SEQUENCE: 91
cacaaatcac agaagatgtc accaaa                                26

<210> SEQ ID NO 92
<211> LENGTH: 23
<212> TYPE: DNA
<213> ORGANISM: Zea mays

<400> SEQUENCE: 92
ccatttgtgc agcttctcta cga                                   23

<210> SEQ ID NO 93
<211> LENGTH: 30
<212> TYPE: DNA
<213> ORGANISM: Zea mays

<400> SEQUENCE: 93
gtgtcttttg gatagactga tagtgatagg                            30

<210> SEQ ID NO 94
<211> LENGTH: 21
<212> TYPE: DNA
<213> ORGANISM: Zea mays

<400> SEQUENCE: 94
cccagagaat ggctcctatg c                                     21

<210> SEQ ID NO 95
<211> LENGTH: 29

```
<212> TYPE: DNA
<213> ORGANISM: Zea mays

<400> SEQUENCE: 95
ggtagtatat gtgcattcat cgtttttca                                29

<210> SEQ ID NO 96
<211> LENGTH: 23
<212> TYPE: DNA
<213> ORGANISM: Zea mays

<400> SEQUENCE: 96
gccgctaagt tgcataccta cac                                      23

<210> SEQ ID NO 97
<211> LENGTH: 21
<212> TYPE: DNA
<213> ORGANISM: Zea mays

<400> SEQUENCE: 97
tgctggccac tcatgtaaag g                                        21

<210> SEQ ID NO 98
<211> LENGTH: 24
<212> TYPE: DNA
<213> ORGANISM: Zea mays

<400> SEQUENCE: 98
ccagagaaac aaggctcttc tttt                                     24

<210> SEQ ID NO 99
<211> LENGTH: 19
<212> TYPE: DNA
<213> ORGANISM: Zea mays

<400> SEQUENCE: 99
cgaagaaaat ccgcaacga                                           19

<210> SEQ ID NO 100
<211> LENGTH: 24
<212> TYPE: DNA
<213> ORGANISM: Zea mays

<400> SEQUENCE: 100
tctaggtttt gctttgtgca caag                                     24

<210> SEQ ID NO 101
<211> LENGTH: 27
<212> TYPE: DNA
<213> ORGANISM: Zea mays

<400> SEQUENCE: 101
tggtttgcag cttattgatt actatga                                  27

<210> SEQ ID NO 102
<211> LENGTH: 19
<212> TYPE: DNA
<213> ORGANISM: Zea mays

<400> SEQUENCE: 102
ggcgcatgac acaaacaca                                           19

<210> SEQ ID NO 103
```

-continued

```
<211> LENGTH: 21
<212> TYPE: DNA
<213> ORGANISM: Zea mays

<400> SEQUENCE: 103
cgtcttgaag tcgagcatga c                                              21

<210> SEQ ID NO 104
<211> LENGTH: 21
<212> TYPE: DNA
<213> ORGANISM: Zea mays

<400> SEQUENCE: 104
tggtaacaat ggcgtcgtca a                                              21

<210> SEQ ID NO 105
<211> LENGTH: 20
<212> TYPE: DNA
<213> ORGANISM: Zea mays

<400> SEQUENCE: 105
ggccatcaac attgccaact                                                20

<210> SEQ ID NO 106
<211> LENGTH: 29
<212> TYPE: DNA
<213> ORGANISM: Zea mays

<400> SEQUENCE: 106
gtctatatat gtaaccaccc tctatgcaa                                      29

<210> SEQ ID NO 107
<211> LENGTH: 24
<212> TYPE: DNA
<213> ORGANISM: Zea mays

<400> SEQUENCE: 107
gtgtacaagc aacagaccaa caac                                           24

<210> SEQ ID NO 108
<211> LENGTH: 30
<212> TYPE: DNA
<213> ORGANISM: Zea mays

<400> SEQUENCE: 108 gtatttttttt tcttttttag acgttgcttt                                    30

<210> SEQ ID NO 109
<211> LENGTH: 31
<212> TYPE: DNA
<213> ORGANISM: Zea mays

<400> SEQUENCE: 109
gtttctagat gactttagac attcagagtg g                                   31

<210> SEQ ID NO 110
<211> LENGTH: 18
<212> TYPE: DNA
<213> ORGANISM: Zea mays

<400> SEQUENCE: 110
gagcgcttcg tgtttgca                                                  18
```

-continued

```
<210> SEQ ID NO 111
<211> LENGTH: 25
<212> TYPE: DNA
<213> ORGANISM: Zea mays

<400> SEQUENCE: 111
gcactaccta tgcgtatgtc aaaga                                              25

<210> SEQ ID NO 112
<211> LENGTH: 25
<212> TYPE: DNA
<213> ORGANISM: Zea mays

<400> SEQUENCE: 112
gaggcatgtc ctttcgtact taatg                                              25

<210> SEQ ID NO 113
<211> LENGTH: 23
<212> TYPE: DNA
<213> ORGANISM: Zea mays

<400> SEQUENCE: 113
gagttttctt tggcggttca tct                                                23

<210> SEQ ID NO 114
<211> LENGTH: 26
<212> TYPE: DNA
<213> ORGANISM: Zea mays

<400> SEQUENCE: 114
ctcaggtttg tcaatgtctt caagtg                                             26

<210> SEQ ID NO 115
<211> LENGTH: 19
<212> TYPE: DNA
<213> ORGANISM: Zea mays

<400> SEQUENCE: 115
atcgaggcgg gactaccta                                                     19

<210> SEQ ID NO 116
<211> LENGTH: 23
<212> TYPE: DNA
<213> ORGANISM: Zea mays

<400> SEQUENCE: 116
agagagctag agacttggaa gca                                                23

<210> SEQ ID NO 117
<211> LENGTH: 26
<212> TYPE: DNA
<213> ORGANISM: Zea mays

<400> SEQUENCE: 117
agctacaata tacagttgcg aacgaa                                             26

<210> SEQ ID NO 118
<211> LENGTH: 21
<212> TYPE: DNA
<213> ORGANISM: Zea mays

<400> SEQUENCE: 118
gcacgaactc agaaccagtg a                                                  21
```

<210> SEQ ID NO 119
<211> LENGTH: 25
<212> TYPE: DNA
<213> ORGANISM: Zea mays

<400> SEQUENCE: 119
cgtagtagta cgttgtgtag aagca                                         25

<210> SEQ ID NO 120
<211> LENGTH: 27
<212> TYPE: DNA
<213> ORGANISM: Zea mays

<400> SEQUENCE: 120
aagacttcag ttaacttact ggatgcc                                       27

<210> SEQ ID NO 121
<211> LENGTH: 22
<212> TYPE: DNA
<213> ORGANISM: Zea mays

<400> SEQUENCE: 121
agcatgagaa aagcatggac aa                                            22

<210> SEQ ID NO 122
<211> LENGTH: 27
<212> TYPE: DNA
<213> ORGANISM: Zea mays

<400> SEQUENCE: 122
gttggtagga ttggaactta ggttaca                                       27

<210> SEQ ID NO 123
<211> LENGTH: 24
<212> TYPE: DNA
<213> ORGANISM: Zea mays

<400> SEQUENCE: 123
tcatctgttc cctttcctct agca                                          24

<210> SEQ ID NO 124
<211> LENGTH: 29
<212> TYPE: DNA
<213> ORGANISM: Zea mays

<400> SEQUENCE: 124
ttaatcagta attggctcct tgagatgtt                                     29

<210> SEQ ID NO 125
<211> LENGTH: 23
<212> TYPE: DNA
<213> ORGANISM: Zea mays

<400> SEQUENCE: 125
cgaagctcga tgcaaaacca att                                           23

<210> SEQ ID NO 126
<211> LENGTH: 23
<212> TYPE: DNA
<213> ORGANISM: Zea mays

<400> SEQUENCE: 126
aaaccaaaag cactcctctc tga                                           23

<210> SEQ ID NO 127
<211> LENGTH: 20
<212> TYPE: DNA
<213> ORGANISM: Zea mays

<400> SEQUENCE: 127
ggttcagcca agccttcaag    20

<210> SEQ ID NO 128
<211> LENGTH: 23
<212> TYPE: DNA
<213> ORGANISM: Zea mays

<400> SEQUENCE: 128
atccttgaca gcatccacat ttt    23

<210> SEQ ID NO 129
<211> LENGTH: 21
<212> TYPE: DNA
<213> ORGANISM: Zea mays

<400> SEQUENCE: 129
tcctccaact tggctattgc a    21

<210> SEQ ID NO 130
<211> LENGTH: 17
<212> TYPE: DNA
<213> ORGANISM: Zea mays

<400> SEQUENCE: 130
gtgggccatg gcacaca    17

<210> SEQ ID NO 131
<211> LENGTH: 22
<212> TYPE: DNA
<213> ORGANISM: Zea mays

<400> SEQUENCE: 131
accaaaccct ggcaagaaag aa    22

<210> SEQ ID NO 132
<211> LENGTH: 24
<212> TYPE: DNA
<213> ORGANISM: Zea mays

<400> SEQUENCE: 132
tctacataat gcagcgctag ttgt    24

<210> SEQ ID NO 133
<211> LENGTH: 24
<212> TYPE: DNA
<213> ORGANISM: Zea mays

<400> SEQUENCE: 133
tgcttacggc acagaataaa tcaa    24

<210> SEQ ID NO 134
<211> LENGTH: 23
<212> TYPE: DNA
<213> ORGANISM: Zea mays

<400> SEQUENCE: 134

```
tgtggaattc gcatcctcat gat                                          23

<210> SEQ ID NO 135
<211> LENGTH: 19
<212> TYPE: DNA
<213> ORGANISM: Zea mays

<400> SEQUENCE: 135
ctgcacggac gaacgtttc                                               19

<210> SEQ ID NO 136
<211> LENGTH: 22
<212> TYPE: DNA
<213> ORGANISM: Zea mays

<400> SEQUENCE: 136
cttcggatcg ctacaaggtg at                                           22

<210> SEQ ID NO 137
<211> LENGTH: 29
<212> TYPE: DNA
<213> ORGANISM: Zea mays

<400> SEQUENCE: 137
accaacaatt gtgtatctga tatgatttc                                    29

<210> SEQ ID NO 138
<211> LENGTH: 19
<212> TYPE: DNA
<213> ORGANISM: Zea mays

<400> SEQUENCE: 138
cgtgagccac cggtacaga                                               19

<210> SEQ ID NO 139
<211> LENGTH: 25
<212> TYPE: DNA
<213> ORGANISM: Zea mays

<400> SEQUENCE: 139
gccactgtta atgttgcttc ttgta                                        25

<210> SEQ ID NO 140
<211> LENGTH: 21
<212> TYPE: DNA
<213> ORGANISM: Zea mays

<400> SEQUENCE: 140
aggtgctact tgctcctgtt c                                            21

<210> SEQ ID NO 141
<211> LENGTH: 25
<212> TYPE: DNA
<213> ORGANISM: Zea mays

<400> SEQUENCE: 141
catagttgtt tcggctttat gtgca                                        25

<210> SEQ ID NO 142
<211> LENGTH: 28
<212> TYPE: DNA
<213> ORGANISM: Zea mays

<400> SEQUENCE: 142
```

-continued accgctacat tgttaagtta tcaatggt                                              28

<210> SEQ ID NO 143
<211> LENGTH: 25
<212> TYPE: DNA
<213> ORGANISM: Zea mays

<400> SEQUENCE: 143
ctggtggtga agaggtttaa gtgtt                                                 25

<210> SEQ ID NO 144
<211> LENGTH: 22
<212> TYPE: DNA
<213> ORGANISM: Zea mays

<400> SEQUENCE: 144
catatgagca cggagcacag aa                                                    22

<210> SEQ ID NO 145
<211> LENGTH: 28
<212> TYPE: DNA
<213> ORGANISM: Zea mays

<400> SEQUENCE: 145
gactggatga acatttataa gaaaacca                                              28

<210> SEQ ID NO 146
<211> LENGTH: 25
<212> TYPE: DNA
<213> ORGANISM: Zea mays

<400> SEQUENCE: 146
ccaaactctc gatgaccaag cataa                                                 25

<210> SEQ ID NO 147
<211> LENGTH: 25
<212> TYPE: DNA
<213> ORGANISM: Zea mays

<400> SEQUENCE: 147
gctgaaattt tgtttctttc ctgaa                                                 25

<210> SEQ ID NO 148
<211> LENGTH: 31
<212> TYPE: DNA
<213> ORGANISM: Zea mays

<400> SEQUENCE: 148
caaaggcact tattccacaa aatttactac t                                          31

<210> SEQ ID NO 149
<211> LENGTH: 23
<212> TYPE: DNA
<213> ORGANISM: Zea mays

<400> SEQUENCE: 149
aaggacttgc ctgttcctaa aca                                                   23

<210> SEQ ID NO 150
<211> LENGTH: 20
<212> TYPE: DNA
<213> ORGANISM: Zea mays

```
<400> SEQUENCE: 150
agggcagcga cagaagaatc                                              20

<210> SEQ ID NO 151
<211> LENGTH: 16
<212> TYPE: DNA
<213> ORGANISM: Zea mays

<400> SEQUENCE: 151
tcggcggcga aatgac                                                  16

<210> SEQ ID NO 152
<211> LENGTH: 21
<212> TYPE: DNA
<213> ORGANISM: Zea mays

<400> SEQUENCE: 152
gcagcgtcaa tgcatcctta t                                            21

<210> SEQ ID NO 153
<211> LENGTH: 25
<212> TYPE: DNA
<213> ORGANISM: Zea mays

<400> SEQUENCE: 153
gctagcgcta gtggtggtaa attac                                        25

<210> SEQ ID NO 154
<211> LENGTH: 15
<212> TYPE: DNA
<213> ORGANISM: Zea mays

<400> SEQUENCE: 154
acctcatcgg cgccg                                                   15

<210> SEQ ID NO 155
<211> LENGTH: 16
<212> TYPE: DNA
<213> ORGANISM: Zea mays

<400> SEQUENCE: 155
catggtcccc gatgtg                                                  16

<210> SEQ ID NO 156
<211> LENGTH: 14
<212> TYPE: DNA
<213> ORGANISM: Zea mays

<400> SEQUENCE: 156
tctgggaccg aagc                                                    14

<210> SEQ ID NO 157
<211> LENGTH: 16
<212> TYPE: DNA
<213> ORGANISM: Zea mays

<400> SEQUENCE: 157
actgatattc aaattc                                                  16

<210> SEQ ID NO 158
<211> LENGTH: 14
<212> TYPE: DNA
<213> ORGANISM: Zea mays
```

```
<400> SEQUENCE: 158
aggcccagca ttca                                                    14

<210> SEQ ID NO 159
<211> LENGTH: 14
<212> TYPE: DNA
<213> ORGANISM: Zea mays

<400> SEQUENCE: 159
tgtggagagg aacg                                                    14

<210> SEQ ID NO 160
<211> LENGTH: 16
<212> TYPE: DNA
<213> ORGANISM: Zea mays

<400> SEQUENCE: 160
ctgttttcgt aaattc                                                  16

<210> SEQ ID NO 161
<211> LENGTH: 15
<212> TYPE: DNA
<213> ORGANISM: Zea mays

<400> SEQUENCE: 161
caggagtacg catcc                                                   15

<210> SEQ ID NO 162
<211> LENGTH: 23
<212> TYPE: DNA
<213> ORGANISM: Zea mays

<400> SEQUENCE: 162
tctaactaaa tcataagggt gca                                          23

<210> SEQ ID NO 163
<211> LENGTH: 20
<212> TYPE: DNA
<213> ORGANISM: Zea mays

<400> SEQUENCE: 163
ttgtgagatt tactaactaa                                              20

<210> SEQ ID NO 164
<211> LENGTH: 19
<212> TYPE: DNA
<213> ORGANISM: Zea mays

<400> SEQUENCE: 164
tctgaatcat cgtcatctt                                               19

<210> SEQ ID NO 165
<211> LENGTH: 16
<212> TYPE: DNA
<213> ORGANISM: Zea mays

<400> SEQUENCE: 165
tagccgtggt ggctga                                                  16

<210> SEQ ID NO 166
<211> LENGTH: 17
<212> TYPE: DNA
```

```
<213> ORGANISM: Zea mays

<400> SEQUENCE: 166
cacctgcctg tagagca                                                  17

<210> SEQ ID NO 167
<211> LENGTH: 17
<212> TYPE: DNA
<213> ORGANISM: Zea mays

<400> SEQUENCE: 167
tatgtcggcc agactat                                                  17

<210> SEQ ID NO 168
<211> LENGTH: 18
<212> TYPE: DNA
<213> ORGANISM: Zea mays

<400> SEQUENCE: 168
acaaggtctc atgagaag                                                 18

<210> SEQ ID NO 169
<211> LENGTH: 16
<212> TYPE: DNA
<213> ORGANISM: Zea mays

<400> SEQUENCE: 169
ccgactgatg atgcat                                                   16

<210> SEQ ID NO 170
<211> LENGTH: 16
<212> TYPE: DNA
<213> ORGANISM: Zea mays

<400> SEQUENCE: 170
aagccgatgc tttgat                                                   16

<210> SEQ ID NO 171
<211> LENGTH: 13
<212> TYPE: DNA
<213> ORGANISM: Zea mays

<400> SEQUENCE: 171
cttgcagatc ctc                                                      13

<210> SEQ ID NO 172
<211> LENGTH: 17
<212> TYPE: DNA
<213> ORGANISM: Zea mays

<400> SEQUENCE: 172 tcacccttt aagagct                                                   17

<210> SEQ ID NO 173
<211> LENGTH: 18
<212> TYPE: DNA
<213> ORGANISM: Zea mays

<400> SEQUENCE: 173
caacacttag ataaaacc                                                 18

<210> SEQ ID NO 174
<211> LENGTH: 14
```

```
<212> TYPE: DNA
<213> ORGANISM: Zea mays

<400> SEQUENCE: 174
atgcagcgac catc                                                   14

<210> SEQ ID NO 175
<211> LENGTH: 20
<212> TYPE: DNA
<213> ORGANISM: Zea mays

<400> SEQUENCE: 175
aatcggtcat ttatgtctac                                             20

<210> SEQ ID NO 176
<211> LENGTH: 16
<212> TYPE: DNA
<213> ORGANISM: Zea mays

<400> SEQUENCE: 176
actccacgtc acctca                                                 16

<210> SEQ ID NO 177
<211> LENGTH: 20
<212> TYPE: DNA
<213> ORGANISM: Zea mays

<400> SEQUENCE: 177
ctcgctttct agcttgttaa                                             20

<210> SEQ ID NO 178
<211> LENGTH: 14
<212> TYPE: DNA
<213> ORGANISM: Zea mays

<400> SEQUENCE: 178
aacaccgtcg ccgg                                                   14

<210> SEQ ID NO 179
<211> LENGTH: 16
<212> TYPE: DNA
<213> ORGANISM: Zea mays

<400> SEQUENCE: 179
ccatcaacca taataa                                                 16

<210> SEQ ID NO 180
<211> LENGTH: 15
<212> TYPE: DNA
<213> ORGANISM: Zea mays

<400> SEQUENCE: 180
aaaccacaaa gaaag                                                  15

<210> SEQ ID NO 181
<211> LENGTH: 17
<212> TYPE: DNA
<213> ORGANISM: Zea mays

<400> SEQUENCE: 181
tgtggaagtg attagtg                                                17

<210> SEQ ID NO 182
```

-continued

```
<211> LENGTH: 19
<212> TYPE: DNA
<213> ORGANISM: Zea mays

<400> SEQUENCE: 182
caattggagt aatgaattc                                                19

<210> SEQ ID NO 183
<211> LENGTH: 18
<212> TYPE: DNA
<213> ORGANISM: Zea mays

<400> SEQUENCE: 183
actttgtacc attgctgc                                                 18

<210> SEQ ID NO 184
<211> LENGTH: 16
<212> TYPE: DNA
<213> ORGANISM: Zea mays

<400> SEQUENCE: 184
tgtcagttcg caatga                                                   16

<210> SEQ ID NO 185
<211> LENGTH: 15
<212> TYPE: DNA
<213> ORGANISM: Zea mays

<400> SEQUENCE: 185
cagctgacac agaaa                                                    15

<210> SEQ ID NO 186
<211> LENGTH: 20
<212> TYPE: DNA
<213> ORGANISM: Zea mays

<400> SEQUENCE: 186
ctgcatatgt actatgaaac                                               20

<210> SEQ ID NO 187
<211> LENGTH: 14
<212> TYPE: DNA
<213> ORGANISM: Zea mays

<400> SEQUENCE: 187
cgaagcaacc ttac                                                     14

<210> SEQ ID NO 188
<211> LENGTH: 15
<212> TYPE: DNA
<213> ORGANISM: Zea mays

<400> SEQUENCE: 188
ctgaagggat tttag                                                    15

<210> SEQ ID NO 189
<211> LENGTH: 13
<212> TYPE: DNA
<213> ORGANISM: Zea mays

<400> SEQUENCE: 189
aggctcgccc tgg                                                      13
```

```
<210> SEQ ID NO 190
<211> LENGTH: 15
<212> TYPE: DNA
<213> ORGANISM: Zea mays

<400> SEQUENCE: 190
caccaggtat agtcc                                                    15

<210> SEQ ID NO 191
<211> LENGTH: 16
<212> TYPE: DNA
<213> ORGANISM: Zea mays

<400> SEQUENCE: 191
ctgcatcaga ctcaat                                                   16

<210> SEQ ID NO 192
<211> LENGTH: 18
<212> TYPE: DNA
<213> ORGANISM: Zea mays

<400> SEQUENCE: 192
tgaccttttc acaagcca                                                 18

<210> SEQ ID NO 193
<211> LENGTH: 19
<212> TYPE: DNA
<213> ORGANISM: Zea mays

<400> SEQUENCE: 193
catatttagc gtttcatca                                                19

<210> SEQ ID NO 194
<211> LENGTH: 17
<212> TYPE: DNA
<213> ORGANISM: Zea mays

<400> SEQUENCE: 194
cagtcttgct tgcacaa                                                  17

<210> SEQ ID NO 195
<211> LENGTH: 16
<212> TYPE: DNA
<213> ORGANISM: Zea mays

<400> SEQUENCE: 195
cgcataacag taaaca                                                   16

<210> SEQ ID NO 196
<211> LENGTH: 16
<212> TYPE: DNA
<213> ORGANISM: Zea mays

<400> SEQUENCE: 196
acaatcaaat tcctcg                                                   16

<210> SEQ ID NO 197
<211> LENGTH: 18
<212> TYPE: DNA
<213> ORGANISM: Zea mays

<400> SEQUENCE: 197
cttgattaga ccaaagtg                                                 18
```

```
<210> SEQ ID NO 198
<211> LENGTH: 15
<212> TYPE: DNA
<213> ORGANISM: Zea mays

<400> SEQUENCE: 198
atggacatca aggaa                                                  15

<210> SEQ ID NO 199
<211> LENGTH: 17
<212> TYPE: DNA
<213> ORGANISM: Zea mays

<400> SEQUENCE: 199
cctcaaactt gaagctg                                                17

<210> SEQ ID NO 200
<211> LENGTH: 16
<212> TYPE: DNA
<213> ORGANISM: Zea mays

<400> SEQUENCE: 200
ctatcacctc tttgcc                                                 16

<210> SEQ ID NO 201
<211> LENGTH: 16
<212> TYPE: DNA
<213> ORGANISM: Zea mays

<400> SEQUENCE: 201
acgatattgc ggtgct                                                 16

<210> SEQ ID NO 202
<211> LENGTH: 16
<212> TYPE: DNA
<213> ORGANISM: Zea mays

<400> SEQUENCE: 202
agaaccgaac gacacg                                                 16

<210> SEQ ID NO 203
<211> LENGTH: 13
<212> TYPE: DNA
<213> ORGANISM: Zea mays

<400> SEQUENCE: 203
ttcgctacaa ccc                                                    13

<210> SEQ ID NO 204
<211> LENGTH: 14
<212> TYPE: DNA
<213> ORGANISM: Zea mays

<400> SEQUENCE: 204
agcatcgttt cctg                                                   14

<210> SEQ ID NO 205
<211> LENGTH: 15
<212> TYPE: DNA
<213> ORGANISM: Zea mays

<400> SEQUENCE: 205
acctcattgg cgccg                                                  15
```

<210> SEQ ID NO 206
<211> LENGTH: 16
<212> TYPE: DNA
<213> ORGANISM: Zea mays

<400> SEQUENCE: 206
catggtctcc gatgtg                                                     16

<210> SEQ ID NO 207
<211> LENGTH: 14
<212> TYPE: DNA
<213> ORGANISM: Zea mays

<400> SEQUENCE: 207
tgggactgaa gcga                                                       14

<210> SEQ ID NO 208
<211> LENGTH: 17
<212> TYPE: DNA
<213> ORGANISM: Zea mays

<400> SEQUENCE: 208
aactgatatt caacttc                                                    17

<210> SEQ ID NO 209
<211> LENGTH: 14
<212> TYPE: DNA
<213> ORGANISM: Zea mays

<400> SEQUENCE: 209
aggcccatca ttca                                                       14

<210> SEQ ID NO 210
<211> LENGTH: 14
<212> TYPE: DNA
<213> ORGANISM: Zea mays

<400> SEQUENCE: 210
tggagtggaa cgct                                                       14

<210> SEQ ID NO 211
<211> LENGTH: 17
<212> TYPE: DNA
<213> ORGANISM: Zea mays

<400> SEQUENCE: 211
tctgttttct taaattc                                                    17

<210> SEQ ID NO 212
<211> LENGTH: 16
<212> TYPE: DNA
<213> ORGANISM: Zea mays

<400> SEQUENCE: 212
acaggagtat gcatcc                                                     16

<210> SEQ ID NO 213
<211> LENGTH: 19
<212> TYPE: DNA
<213> ORGANISM: Zea mays

<400> SEQUENCE: 213

```
actaaatcat gagggtgca                                           19

<210> SEQ ID NO 214
<211> LENGTH: 20
<212> TYPE: DNA
<213> ORGANISM: Zea mays

<400> SEQUENCE: 214
tgtgagattt actaactcat                                          20

<210> SEQ ID NO 215
<211> LENGTH: 19
<212> TYPE: DNA
<213> ORGANISM: Zea mays

<400> SEQUENCE: 215
tctgaatcat catcatctt                                           19

<210> SEQ ID NO 216
<211> LENGTH: 16
<212> TYPE: DNA
<213> ORGANISM: Zea mays

<400> SEQUENCE: 216
tagccgtgat ggctga                                              16

<210> SEQ ID NO 217
<211> LENGTH: 15
<212> TYPE: DNA
<213> ORGANISM: Zea mays

<400> SEQUENCE: 217
cctgcctgca gagca                                               15

<210> SEQ ID NO 218
<211> LENGTH: 16
<212> TYPE: DNA
<213> ORGANISM: Zea mays

<400> SEQUENCE: 218
atgtcgacca gactat                                              16

<210> SEQ ID NO 219
<211> LENGTH: 17
<212> TYPE: DNA
<213> ORGANISM: Zea mays

<400> SEQUENCE: 219
caaggtctca agagaag                                             17

<210> SEQ ID NO 220
<211> LENGTH: 16
<212> TYPE: DNA
<213> ORGANISM: Zea mays

<400> SEQUENCE: 220
ccgactgatc atgcat                                              16

<210> SEQ ID NO 221
<211> LENGTH: 15
<212> TYPE: DNA
<213> ORGANISM: Zea mays

<400> SEQUENCE: 221
```

```
agccgatgcc ttgat                                                    15

<210> SEQ ID NO 222
<211> LENGTH: 13
<212> TYPE: DNA
<213> ORGANISM: Zea mays

<400> SEQUENCE: 222
cttgctgatc ctc                                                      13

<210> SEQ ID NO 223
<211> LENGTH: 15
<212> TYPE: DNA
<213> ORGANISM: Zea mays

<400> SEQUENCE: 223
caccccttta agagc                                                    15

<210> SEQ ID NO 224
<211> LENGTH: 16
<212> TYPE: DNA
<213> ORGANISM: Zea mays

<400> SEQUENCE: 224
acacttagac aaaacc                                                   16

<210> SEQ ID NO 225
<211> LENGTH: 13
<212> TYPE: DNA
<213> ORGANISM: Zea mays

<400> SEQUENCE: 225
tgcagcaacc atc                                                      13

<210> SEQ ID NO 226
<211> LENGTH: 18
<212> TYPE: DNA
<213> ORGANISM: Zea mays

<400> SEQUENCE: 226
tcggtcattt atctctac                                                 18

<210> SEQ ID NO 227
<211> LENGTH: 14
<212> TYPE: DNA
<213> ORGANISM: Zea mays

<400> SEQUENCE: 227
tccacgccac ctca                                                     14

<210> SEQ ID NO 228
<211> LENGTH: 18
<212> TYPE: DNA
<213> ORGANISM: Zea mays

<400> SEQUENCE: 228
cgctttctag catgttaa                                                 18

<210> SEQ ID NO 229
<211> LENGTH: 14
<212> TYPE: DNA
<213> ORGANISM: Zea mays
```

-continued

```
<400> SEQUENCE: 229
aacaccgtgg ccgg                                              14

<210> SEQ ID NO 230
<211> LENGTH: 15
<212> TYPE: DNA
<213> ORGANISM: Zea mays

<400> SEQUENCE: 230
aaccacaata atttc                                             15

<210> SEQ ID NO 231
<211> LENGTH: 13
<212> TYPE: DNA
<213> ORGANISM: Zea mays

<400> SEQUENCE: 231
aaaccgcaaa gaa                                               13

<210> SEQ ID NO 232
<211> LENGTH: 16
<212> TYPE: DNA
<213> ORGANISM: Zea mays

<400> SEQUENCE: 232
agtgatcagt gatttc                                            16

<210> SEQ ID NO 233
<211> LENGTH: 16
<212> TYPE: DNA
<213> ORGANISM: Zea mays

<400> SEQUENCE: 233
ttggagtagt gaattc                                            16

<210> SEQ ID NO 234
<211> LENGTH: 17
<212> TYPE: DNA
<213> ORGANISM: Zea mays

<400> SEQUENCE: 234
ctttgtacca ctgctgc                                           17

<210> SEQ ID NO 235
<211> LENGTH: 15
<212> TYPE: DNA
<213> ORGANISM: Zea mays

<400> SEQUENCE: 235
cagtttgcaa tgaca                                             15

<210> SEQ ID NO 236
<211> LENGTH: 16
<212> TYPE: DNA
<213> ORGANISM: Zea mays

<400> SEQUENCE: 236
ccagctgaaa cagaaa                                            16

<210> SEQ ID NO 237
<211> LENGTH: 20
<212> TYPE: DNA
<213> ORGANISM: Zea mays
```

```
<400> SEQUENCE: 237
ctgcatatgt actctgaaac                                               20

<210> SEQ ID NO 238
<211> LENGTH: 14
<212> TYPE: DNA
<213> ORGANISM: Zea mays

<400> SEQUENCE: 238
cgaagcgacc ttac                                                     14

<210> SEQ ID NO 239
<211> LENGTH: 16
<212> TYPE: DNA
<213> ORGANISM: Zea mays

<400> SEQUENCE: 239
agctgaagtg atttta                                                   16

<210> SEQ ID NO 240
<211> LENGTH: 14
<212> TYPE: DNA
<213> ORGANISM: Zea mays

<400> SEQUENCE: 240
aggctcgtcc tggg                                                     14

<210> SEQ ID NO 241
<211> LENGTH: 15
<212> TYPE: DNA
<213> ORGANISM: Zea mays

<400> SEQUENCE: 241
ccaggtagag tccaa                                                    15

<210> SEQ ID NO 242
<211> LENGTH: 16
<212> TYPE: DNA
<213> ORGANISM: Zea mays

<400> SEQUENCE: 242
ctgcatcaaa ctcaat                                                   16

<210> SEQ ID NO 243
<211> LENGTH: 16
<212> TYPE: DNA
<213> ORGANISM: Zea mays

<400> SEQUENCE: 243
accttttccc aagcca                                                   16

<210> SEQ ID NO 244
<211> LENGTH: 19
<212> TYPE: DNA
<213> ORGANISM: Zea mays

<400> SEQUENCE: 244
catatttagc gcttcatca                                                19

<210> SEQ ID NO 245
<211> LENGTH: 17
<212> TYPE: DNA
```

```
<213> ORGANISM: Zea mays

<400> SEQUENCE: 245
cagtcttgct agcacaa                                                    17

<210> SEQ ID NO 246
<211> LENGTH: 17
<212> TYPE: DNA
<213> ORGANISM: Zea mays

<400> SEQUENCE: 246
acgcataact gtaaaca                                                    17

<210> SEQ ID NO 247
<211> LENGTH: 15
<212> TYPE: DNA
<213> ORGANISM: Zea mays

<400> SEQUENCE: 247
caatcagatt cctcg                                                      15

<210> SEQ ID NO 248
<211> LENGTH: 16
<212> TYPE: DNA
<213> ORGANISM: Zea mays

<400> SEQUENCE: 248
tgattaggcc aaagtg                                                     16

<210> SEQ ID NO 249
<211> LENGTH: 14
<212> TYPE: DNA
<213> ORGANISM: Zea mays

<400> SEQUENCE: 249
tggacctcaa ggaa                                                       14

<210> SEQ ID NO 250
<211> LENGTH: 17
<212> TYPE: DNA
<213> ORGANISM: Zea mays

<400> SEQUENCE: 250
cctcaaactt caagctg                                                    17

<210> SEQ ID NO 251
<211> LENGTH: 15
<212> TYPE: DNA
<213> ORGANISM: Zea mays

<400> SEQUENCE: 251
agcctatcaa ctctt                                                      15

<210> SEQ ID NO 252
<211> LENGTH: 15
<212> TYPE: DNA
<213> ORGANISM: Zea mays

<400> SEQUENCE: 252
cgatatcgcg gtgct                                                      15

<210> SEQ ID NO 253
<211> LENGTH: 14
```

```
<212> TYPE: DNA
<213> ORGANISM: Zea mays

<400> SEQUENCE: 253
ccgaatgaca cggc                                                     14

<210> SEQ ID NO 254
<211> LENGTH: 14
<212> TYPE: DNA
<213> ORGANISM: Zea mays

<400> SEQUENCE: 254
cttcgctata accc                                                     14

<210> SEQ ID NO 255
<211> LENGTH: 14
<212> TYPE: DNA
<213> ORGANISM: Zea mays

<400> SEQUENCE: 255
agcatggttt cctg                                                     14

<210> SEQ ID NO 256
<211> LENGTH: 1108
<212> TYPE: DNA
<213> ORGANISM: Zea mays
<220> FEATURE:
<221> NAME/KEY: misc_feature
<222> LOCATION: (350)..(350)
<223> OTHER INFORMATION: n is a, c, g, or t

<400> SEQUENCE: 256
gctgcgtggg aggggggagcg gcggcatcaa cagccgcaga ggaaggctta ctctgaagcg   60
gaggggaagc aggctggcat tgctactggg agcatggcga ggtgctaagg acgtgcaggt  120
tccgcaatca ccgcatcttg gtgttcttat ttcaggtcgt agtgggagat gaacctctca  180
ccgcccaaga tgtcggagcc atcgcttgaa agtgacggta tgtcatggat cacaattttg  240
gcattgattc agttcagaac ttctcaactt gtgttgatgt ctgcatggga tagtggatta  300
tgcaatgttg tcattgtgca ttgatgtttc caaacaaatg atgaaaaccn gcttgctctt  360
gtatatatgc acgattacat tcgttcattc atattcttca ttgatttgct caaaagaaa  420
aggttcatgc attgctcggc ttcactcatg gttcacatgt tctagtatta ttggtattca  480
ctgaacctcc tcttgtctgt agccaagtac gaatagtagg gttcacatga actctgcttt  540
ctggtggctt cctgttccac tcatgtgtgt ttggcatttt gcaggggaac aaaggtgtct  600
gaactcggag ctatggcatg catgcgcagg gcccttgtg tcccttcctg tggttgggag   660
ccgggtcgtc tactttcccc agggccatag tgagcaggtc ggtcactcgg tcacaaagca  720
gtttctttga ataaactaga catgaccgag tttgttgact tcagactatc aggttttgtg  780
aatggggaat gaaatgatc acttgagctg ctacctttct ggttcttttg attgtatatg   840
tcaaatggat cgactgaaca taacacttcc gaagattcaa ctgaaaaatt actttggcca  900
actatacaca taaagataat cttgtattca aataatcaaa tttgttcaaa ggttgttatc  960
acttgaaatc acttttttaag tcaatctagt tttgtacagg tttatttata gagaatcact 1020
tgctctcatg cctttgtgct taagaggttc ttttgtttgt ttttattttc atgcaggttg 1080
ctgcatcaac taataaagaa gtgacgct                                    1108

<210> SEQ ID NO 257
```

```
<211> LENGTH: 708
<212> TYPE: DNA
<213> ORGANISM: Zea mays
<220> FEATURE:
<221> NAME/KEY: misc_feature
<222> LOCATION: (456)..(456)
<223> OTHER INFORMATION: n is a, c, g, or t

<400> SEQUENCE: 257
cattgctcgc ggtataacat catttgtctt ctttcctatt ttattgtcct ttcccttttg      60
tgctgcaagt tttaaccttt tccatggtac ctgtcatgct agtcatctgg gaaagcattg     120
cggaaggata aaccttcaca agatgtagaa gaaacctctg ttaaagaatc aaaaccatca     180
gctggtactt tgacattttc ctctcatttt caggctttta tttgtgatat gtggtagctc     240
cttgcgtgga tagttgatta ctgcctcttt tttttcttcc tgttctgtac aatagcaatt     300
ttgccagaat gttctgatga tcagtctttt ggtagttgac ttaattttat tagaaatagt     360
aataatgtta gtttgctgaa tattaccctc ccatattgaa ctggaaaatg gaagttttag     420
tgtgaagtac atttttttca tgtttgacag tttganacat ttacaccctg tactcttcca     480
ggtgaagatg attcgtcaaa aatatgttat aaatgcaaaa aggctggaca tctttctcgc     540
gattgcccag aaagcacatc tgaggtggac cgaaatgatg gcagtattag tagaagcaga     600
gacgatacgg gtaccaatac tgctcctgct ggtggcaaca gtcctatgga cgaagacgat     660
gttcaagaaa ttggtgatga agagaaagaa aagttgattg acttggac                  708

<210> SEQ ID NO 258
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 258
aaccgactgt ttttttttc tataggaaaa ggacatcata tatatatatt aatagagcat       60
gccttggaag atgataaaat gactttgaat aatttgcatt ngtgaagctg atcggaaaaa     120
aaggtccatg tgcacttaca tttgatgttt tcccttcgaa catccaacat atgtgcatgc     180
agaggacnca aaacggttag a                                               201

<210> SEQ ID NO 259
<211> LENGTH: 714
<212> TYPE: DNA
<213> ORGANISM: Zea mays
<220> FEATURE:
<221> NAME/KEY: misc_feature
<222> LOCATION: (35)..(41)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (651)..(652)
<223> OTHER INFORMATION: n is a, c, g, or t
```

```
<220> FEATURE:
<221> NAME/KEY: misc_feature
<222> LOCATION: (668)..(669)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (695)..(696)
<223> OTHER INFORMATION: n is a, c, g, or t
<220> FEATURE:
<221> NAME/KEY: misc_feature
<222> LOCATION: (702)..(709)
<223> OTHER INFORMATION: n is a, c, g, or t

<400> SEQUENCE: 259
ctcagcagtt ttaagtttct ctatagttca cactnnnnnn nacaaatccg gctgtgccca    60
aacaactcta ttnaacagag aagcatcgaa actagcatgg agcaaaatct gaattcctta   120
aatctccaac ctaaaacact tagccgacca aaaagcccct gcttcccaaa cgattcgcca   180
agttcgttaa agattttggg ggaaaacgag gcctaaacaa cgggaagtaa gggaaatcaa   240
tagaaaaaac atggttttgg tgagaacctg tgcctagcng cgctctgggg aagattggct   300
gagggagctg cgttttgggg gagtgcaaga ggagcacggt atccagggaa gatgtgcggg   360
agagagatat atattggata cagctcaaga ggggaggaac gctcctcctt aattgttcaa   420
ggcaacgctc ctgccttctt ccaaaaaaaa gaggggagga tcctgacaaa attccagcaa   480
agataggtgt gagagtttat tgctgccttc cttttctgct tgccttttt atctcctcaa    540 aagagttgtg tttgtgttct atcccccgta aaacacaatt tggaaagtgt ttctcaaaaa   600
ttctgatgca tgcattgact ctcttttttt tgtcactatc ctggatttct nngtattctt   660
atttccanng tantgataac taaaaaaatg aancnntagt tnnnnnnnnt atat         714

<210> SEQ ID NO 260
<211> LENGTH: 1924
<212> TYPE: DNA
<213> ORGANISM: Zea mays
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (83)..(104)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t

<400> SEQUENCE: 260
nnnnnnnncc caacatctcc ccgtccaggt cgttgggtca gccctatcc ttcaccttca     60 cgacttcacc tgcttctcca ctnnnnnnnn nnnnnnnnnn nnntcgtgc gccctgctca    120 gatccatcgc acgggcttg ccgcaccact gcgccaagca aaaggtgggc ggccagcggc    180
gcgtgcgcag atcatgcact ggtaggacta atttgcaaga tcttggaccg ggatggttcg   240
cctgttagtt gtcttatgaa gattggtaag gggagaaaga agatgaggaa taaacagcga   300
aaatcatctg ccctcggttc tgatgcagga tgtggatctt ctttatcctg tattgtatgg   360
```

```
agcttggtgg gttttggtct tgtctgcttc attttcctta aacatcaagc agacagtggt    420
cagacccatg tttatttcag tcctcttcat gcgaccagag aattagagga catcgaggag    480
gatcatttcc gcttgccacc tcctcacaag gtgaatcctc gtgcagtgaa aaggagggga    540
cctcgtaaac aaccaaaggt tatagatgat tatctggagg agtcttcagc agtacatgca    600
ctgttctttc cagatcaaat gactgctgtg gatccaacaa aaggaggaaa tgatagcatg    660
tatttctatc ctggtagagt gtggctagac actgatggaa acaccattca agcccatggt    720 gggggggatta tgtatgatca caagactgcc agattctatt ggtatggaga aaacaaggat    780
ggaccaacat accaagctcg ccccaaagga cacagaggg  ttgacatcat tggggtaagc    840
tgctactcat caaaagacct gtggtcgtgg actcatgaag gaattgtgct tcgtggtgag    900
ccttctaatg tcatccatga cctttataaa tcaaaggtgc ttgagagacc taaggtgata    960
tataatgatc gcactgaaaa atatatcatg tggatgcana tcgatgatgc taactacacc   1020
aaagcatctg tcggtgtggc cgtgagtagc tctccgactg gacctttac  ttaccttttac   1080 agctttcgtc cacatggttg tgagagtaga gacatgacag tcttcaaaga tgacgatgga   1140
atggcttacc tcttctattc ttctcgtgac aatactgagc tccatgttag cccattgaca   1200
gaggactacc ttcagatcac agcagcaatg aagagaatac taataaggcg gcatcgtgag   1260
gctccagccg tcttcaagca ccaggggacc tactacatga tcacctctgg ttgctcaggc   1320
tgggctccca acagggcatt ggcacatgct gcagagtcta tcatgggccc atgggagaca   1380
ctgggaaacc cttgcgttgg aggcaacagg ttttaccgcc ttacaacatt cttatctcaa   1440
agcacatttg tgcttcccct ccctggtttg tctggtgcat ttatcttcat ggcggatagg   1500
tggagtccgt caaacttgag agactcccgg tatgtgtggc ttcctctatt cgtcggaggg   1560
ctcgcagaca aacctttaga ttacagtttt ggtttccctc tgtggtcaag ggtatcgatt   1620
tattggcaca agaaatggcg cctcccagaa gattggaaga ttgcaaacac agcaaataca   1680
taagatagct agctatactt gaaccgatag atcgttcata aacttgcttg aggattctaa   1740
tcgcttgctc ctcaagcttt tgtacaaaac agtcatccta aacatgcttc agtgatatat   1800
cttttttttt ggcgtgtgca tgtgtctgta acttctcttg gaaaaagaag tgtgtttcag   1860
ataactgtat tgataattgg tatgaccata ctctgtcgtt tatgccagga cagcaaggtg   1920
catc                                                                1924
```

<210> SEQ ID NO 261
<211> LENGTH: 384
<212> TYPE: DNA
<213> ORGANISM: Zea mays
<220> FEATURE:
<221> NAME/KEY: misc_feature
<222> LOCATION: (106)..(106)
<223> OTHER INFORMATION: n is a, c, g, or t

<400> SEQUENCE: 261

```
atcattcctt tatctattgg aaatctcaaa gggttaaatg tctttgatgc acatcattgc     60
aacttggggg ggccaattcc agcaagcata ggcaacatgt cgaatngtt  gacacttgat    120 ttatcaaaga actccctcga tggttcaatt tccaatgaga ttttcaaact gtcatccctt    180
gacccttatc tatttaaagt tttaaactta tcatacaatt cgctatcggg acatcttcct    240
tctgagatga gtagtttggg gaacctgaac caactagttc tgtctgggaa ccgattgtct    300
ggcgagatac ctgagagtat tggggaatgc actgtgctgc aatacctat  attggatata    360 taactcaatc gatggaagca tacc                                           384
```

<210> SEQ ID NO 262
<211> LENGTH: 201
<212> TYPE: DNA
<213> ORGANISM: Zea mays
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 262
ttgtgcactg tagtttgtat attatatgtg aagtgctggt gtgtatngct catgatgtta    60
ttctttaatt ttggacaggc aagatcttcg agaaggtttg ngaggcatgc cacatatctg    120
tcaacaagac accaatntat ggagataatg gctcgatatc gccaggtggt gtgcggattg    180
gttagttctt tcaactcgat a                                              201

<210> SEQ ID NO 263
<211> LENGTH: 2699
<212> TYPE: DNA
<213> ORGANISM: Zea mays
<220> FEATURE:
<221> NAME/KEY: misc_feature
<222> LOCATION: (1946)..(1946)
<223> OTHER INFORMATION: n is a, c, g, or t

<400> SEQUENCE: 263
gcaaggcaag tagccgctgc gcggtgctgc cacctgacct gactgccgtc ccggtccccg    60
gtccatccga acgccgttac ggggccgccc accgcgacgg aacggaaagg tgcggtcaac    120
ccaccccgtc ccagtcccat caccgccggg ggccgggtgg ataaacaaac ccagcggccc    180
ccgcccccgg cccgcctcat tcccttcctt cctttgctcc tccctgcct cgcctctctc    240 ccctctcctc gcctccagct cctgctcggc ccgctcgcgt ccagctgcgc gcgcgcctgc    300
ggtggccgtg aaggacagcc cgagggacgc gccgggtgca ctgatctggg ggccgcgtgt    360
ccccggtggt ggggcgaggc ggcgccggct tccaggaatg ggcagcttgt agtggctgtt    420
tcttttgcat atgcactttc tattgttgtt gtcatttcaa aggaggccat agtctcctgg    480
attttgtatg ccttgttatc tggaattggt gaccatagat gtcatttcgt agcatagtcc    540
gtgatgttag ggatggcttc ggcagcttgt cgaggagaag ctttgaggtg accctcgcaa    600
gcatttatgg ccttactggg catcacaaag ggaagaccca gagctcatca catgtgctcg    660
acgactcacc ttccataatt cgtgaaagtc gatgggcgaa tctacctcct gaactcatcc    720
gtgatatcat acggagactg gaggctgatg agagcacctg gccagcgcgg aagcacgtcg    780
tttgcttcgc agctgtttgt aggacatgga gagaaatgtg taaagagatt gtgttgagcc    840
cggagttttg tggcaagctc accttccctg tgtctctaaa acagcctggt cctcgagatg    900
gaaatacaat ggtccagtgt tttataaaga ggaataagtc aaaatccact taccatctct    960
acctgtgcct tagcaatgtt gttacttcag aaagtgggaa attcctctta tcagctaaac   1020
gacaccgcaa aaccacatgc accgagtaca ctatatcaat ggattctggc aacatctcaa   1080
gatcaaaaag aacctacatt ggaaaaataa ggtctaactt ccttggcaca agattttaa   1140

```
tttatgatac acaaccgccc tataatgggg ctgtagttcc tcctgccgga aggacaagca    1200
ggaggttcaa ctccacaaaa gtctctccaa agctgccttc agtcagttac aacatcgcac    1260
aggtatcgta tgagttaaat gtccttggca cgagaggtcc taggcggatg cgttgcatca    1320
tgcactccat acctgcatca tcagtggagc caggtggcac agtgcctgga cagccagagc    1380
agattgtacc tcgagccctg gaggattcat tccgcagcac ggcttccttc tcgcagtcgt    1440
tccgtagcac tgcctcattc tccaagtcca tcatggactc atccatggat ttcaatagcg    1500
ctcgcttctc tgacatcgct ggcagcagcg ctcgcttcac gggcgttcct ggtagcagcg    1560
ctcgcttcgc gggcgttcct ggcagcagcg ctcgcttctc gggcattgct ggcgccagac    1620
tggacaacga cgaggagagt gaaaccaagg agaggccact ggtgcttcgt aataagccgc    1680
ctaggtggca cgaacagctg cagtgttggt gcctcaactt ccgtggccgt gtgacaattg    1740
cctcggtgaa gaacttccag ctgatcgccg cggctacccc gccaccggca ggtgcgccaa    1800 cccccctctca gcctgccccg tcagatcccg acaaggtgat tctccagttt ggcaaagtgg    1860
caagggatat gttcacgatg gactatcgct accctctctc ggctttccag gcctttgcca    1920
tttgtctgag tagctttgat acaaanttag cctgtgaata aatggagaag aacaaaggta    1980
aaggagaaca tcaggttgct tgcattaggc catcagtgta cctctttcca tctggctctc    2040
gtgttgcctt ggttgtattt gtgcttaatg tagccatgaa gttggtggcc atatatggac    2100
gcatgtgttg ttgttggccc tctcccttag aagtgattaa aagttgcatt tggaccacat    2160
gttacccgat ctgtaatata cttgcagtgg cattgcatgc cgcgtgataa caaagttccc    2220
gttcgtgatt ggacttgtat ggtttcagaa aagcagcaaa caaagtttgg tacggtgtgc    2280
attttttttt cctcgtctct ggattggtta ctgtttgaag tgaactgcat cttgtctttc    2340 gccctgtgt cttttgagaa gcgagcaaga gggcttacg gctttgtctc acctcaaaag     2400
ggatcgccgc cgagtgccaa accccaccca cccatacatc catcctttta tcagtggtta    2460
tgagcacgac tatatgtaat catcattgcc tgcattacct acaacgcgta tccctcacag    2520
cgttgcgcat tagattcaga tttagacggg caacaatgcc tgtgtgtgac atgggagctc    2580
gagcatcata tcacatgaac ctgcttgtgc atgccttttc ggcccgaata aagccgagct    2640
ctttcggtgt ggccctgtct tttgttatga gttgtttcgg ggggaagacg ccggaacag     2699
```

<210> SEQ ID NO 264
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (145)..(145)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t

<400> SEQUENCE: 264

```
gaaggtggtt gctccgccgg agaggaagta cagcgtttgg attggtggct ccattctggc      60
ctctctcagt accttccagc aggttgttag tttgttactg nctcaaaatc taaattcaac     120
```

```
gtttctgctt gctttgcagt tctantgnat atgaagtttg anttattaat cttgttattg    180
tgttgtgtag atgtggatct c                                              201

<210> SEQ ID NO 265
<211> LENGTH: 26
<212> TYPE: DNA
<213> ORGANISM: Zea mays

<400> SEQUENCE: 265
atgtctgcat gggatagtgg attatg                                          26

<210> SEQ ID NO 266
<211> LENGTH: 29
<212> TYPE: DNA
<213> ORGANISM: Zea mays

<400> SEQUENCE: 266
tgaactggaa aatggaagtt ttagtgtga                                       29

<210> SEQ ID NO 267
<211> LENGTH: 26
<212> TYPE: DNA
<213> ORGANISM: Zea mays

<400> SEQUENCE: 267
agagcatgcc ttggaagatg ataaaa                                          26

<210> SEQ ID NO 268
<211> LENGTH: 18
<212> TYPE: DNA
<213> ORGANISM: Zea mays

<400> SEQUENCE: 268
cggctgtgcc caaacaac                                                   18

<210> SEQ ID NO 269
<211> LENGTH: 28
<212> TYPE: DNA
<213> ORGANISM: Zea mays

<400> SEQUENCE: 269
aggtgatata taatgatcgc actgaaaa                                        28

<210> SEQ ID NO 270
<211> LENGTH: 21
<212> TYPE: DNA
<213> ORGANISM: Zea mays

<400> SEQUENCE: 270
tccagcaagc ataggcaaca t                                               21

<210> SEQ ID NO 271
<211> LENGTH: 22
<212> TYPE: DNA
<213> ORGANISM: Zea mays

<400> SEQUENCE: 271
ggacaggcaa gatcttcgag aa                                              22

<210> SEQ ID NO 272
<211> LENGTH: 24
<212> TYPE: DNA
```

<213> ORGANISM: Zea mays

<400> SEQUENCE: 272
tgccatttgt ctgagtagct ttga                                   24

<210> SEQ ID NO 273
<211> LENGTH: 21
<212> TYPE: DNA
<213> ORGANISM: Zea mays

<400> SEQUENCE: 273
ggcctctctc agtaccttcc a                                      21

<210> SEQ ID NO 274
<211> LENGTH: 29
<212> TYPE: DNA
<213> ORGANISM: Zea mays

<400> SEQUENCE: 274
gaatatgaat gaacgaatgt aatcgtgca                              29

<210> SEQ ID NO 275
<211> LENGTH: 25
<212> TYPE: DNA
<213> ORGANISM: Zea mays

<400> SEQUENCE: 275
tttgacgaat catcttcacc tggaa                                  25

<210> SEQ ID NO 276
<211> LENGTH: 25
<212> TYPE: DNA
<213> ORGANISM: Zea mays

<400> SEQUENCE: 276
tcaaatgtaa gtgcacatgg acctt                                  25

<210> SEQ ID NO 277
<211> LENGTH: 23
<212> TYPE: DNA
<213> ORGANISM: Zea mays

<400> SEQUENCE: 277
gattttgctc catgctagtt tcg                                    23

<210> SEQ ID NO 278
<211> LENGTH: 24
<212> TYPE: DNA
<213> ORGANISM: Zea mays

<400> SEQUENCE: 278
ccgacagatg ctttggtgta gtta                                   24

<210> SEQ ID NO 279
<211> LENGTH: 25
<212> TYPE: DNA
<213> ORGANISM: Zea mays

<400> SEQUENCE: 279
gaagatgtcc cgatagcgaa ttgta                                  25

<210> SEQ ID NO 280
<211> LENGTH: 23

<212> TYPE: DNA
<213> ORGANISM: Zea mays

<400> SEQUENCE: 280
ctggcgatat cgagccatta tct                                    23

<210> SEQ ID NO 281
<211> LENGTH: 25
<212> TYPE: DNA
<213> ORGANISM: Zea mays

<400> SEQUENCE: 281
gcaacctgat gttctccttt acctt                                  25

<210> SEQ ID NO 282
<211> LENGTH: 25
<212> TYPE: DNA
<213> ORGANISM: Zea mays

<400> SEQUENCE: 282
caaagcaagc agaaacgttg aattt                                  25

<210> SEQ ID NO 283
<211> LENGTH: 20
<212> TYPE: DNA
<213> ORGANISM: Zea mays

<400> SEQUENCE: 283
aaatgatgaa aaccagcttg                                        20

<210> SEQ ID NO 284
<211> LENGTH: 19
<212> TYPE: DNA
<213> ORGANISM: Zea mays

<400> SEQUENCE: 284
tgacagtttg aaacattta                                         19

<210> SEQ ID NO 285
<211> LENGTH: 17
<212> TYPE: DNA
<213> ORGANISM: Zea mays

<400> SEQUENCE: 285
tttgcattgg tgaagct                                           17

<210> SEQ ID NO 286
<211> LENGTH: 17
<212> TYPE: DNA
<213> ORGANISM: Zea mays

<400> SEQUENCE: 286
cttctctgtt gaataga                                           17

<210> SEQ ID NO 287
<211> LENGTH: 14
<212> TYPE: DNA
<213> ORGANISM: Zea mays

<400> SEQUENCE: 287
tggatgcaca tcga                                              14

<210> SEQ ID NO 288

```
<211> LENGTH: 16
<212> TYPE: DNA
<213> ORGANISM: Zea mays

<400> SEQUENCE: 288
tgtcaacaga ttcgac                                                       16

<210> SEQ ID NO 289
<211> LENGTH: 15
<212> TYPE: DNA
<213> ORGANISM: Zea mays

<400> SEQUENCE: 289
catgcctcgc aaacc                                                        15

<210> SEQ ID NO 290
<211> LENGTH: 20
<212> TYPE: DNA
<213> ORGANISM: Zea mays

<400> SEQUENCE: 290
attcacaggc taattttgta                                                   20

<210> SEQ ID NO 291
<211> LENGTH: 21
<212> TYPE: DNA
<213> ORGANISM: Zea mays

<400> SEQUENCE: 291
agtttgttac tgtctcaaaa t                                                 21

<210> SEQ ID NO 292
<211> LENGTH: 18
<212> TYPE: DNA
<213> ORGANISM: Zea mays

<400> SEQUENCE: 292
atgatgaaaa ccggcttg                                                     18

<210> SEQ ID NO 293
<211> LENGTH: 17
<212> TYPE: DNA
<213> ORGANISM: Zea mays

<400> SEQUENCE: 293
acagtttgag acattta                                                      17

<210> SEQ ID NO 294
<211> LENGTH: 16
<212> TYPE: DNA
<213> ORGANISM: Zea mays

<400> SEQUENCE: 294
ttgcattcgt gaagct                                                       16

<210> SEQ ID NO 295
<211> LENGTH: 18
<212> TYPE: DNA
<213> ORGANISM: Zea mays

<400> SEQUENCE: 295
atgcttctct gttaaata                                                     18
```

```
<210> SEQ ID NO 296
<211> LENGTH: 16
<212> TYPE: DNA
<213> ORGANISM: Zea mays

<400> SEQUENCE: 296
tggatgcata tcgatg                                                    16

<210> SEQ ID NO 297
<211> LENGTH: 16
<212> TYPE: DNA
<213> ORGANISM: Zea mays

<400> SEQUENCE: 297
tgtcaacaaa ttcgac                                                    16

<210> SEQ ID NO 298
<211> LENGTH: 15
<212> TYPE: DNA
<213> ORGANISM: Zea mays

<400> SEQUENCE: 298
catgcctcac aaacc                                                     15

<210> SEQ ID NO 299
<211> LENGTH: 17
<212> TYPE: DNA
<213> ORGANISM: Zea mays

<400> SEQUENCE: 299
cacaggctaa ctttgta                                                   17

<210> SEQ ID NO 300
<211> LENGTH: 18
<212> TYPE: DNA
<213> ORGANISM: Zea mays

<400> SEQUENCE: 300
ttgttactgc ctcaaaat                                                  18
```

METHODS AND COMPOSITIONS FOR PRODUCING CORN PLANTS WITH RESISTANCE TO LATE WILT

CROSS-REFERENCE TO RELATED APPLICATIONS AND INCORPORATION OF SEQUENCE LISTING

This application claims the benefit of U.S. Provisional Application No. 62/373,777, filed Aug. 11, 2016, which is incorporated by reference herein in its entirety. A sequence listing contained in the file named "P34458US01_SEQ.txt" which is 120,269 bytes in size (measured in MS-Windows®) and created on Aug. 10, 2017, is filed electronically herewith and incorporated by reference in its entirety.

FIELD

The present disclosure relates to the field of agricultural biotechnology. More specifically, this disclosure relates to methods for producing corn plants or seeds with improved late wilt resistance.

BACKGROUND

Corn (*Zea mays* L.) is one of the most important commercial crops in the world. Like many commercial crops, corn is subjected to numerous potentially detrimental environmental conditions (e.g., moisture availability, temperature stresses, soil conditions, pests, disease) that can reduce, or entirely eliminate, crop yield. Crop disease alone accounted for the loss of more than 1.3 billion bushels of corn in the United States and Ontario, Canada in 2012. See Mueller, Corn Disease Loss Estimates from the United States and Ontario, Canada—2012. *Purdue Extension Publication BP*-96-12-W (2014).

Late wilt, or black bundle disease, is a vascular wilt disease of corn. It was first reported in Egypt in 1960 and is an important disease in Egypt and parts of India. Late wilt is characterized by relatively rapid wilting of maize plants, typically at the age of 70 to 80 days, before tasseling and until shortly before maturity. First symptoms appear approximately 60 days after sowing and include the development of light green stripes on the leaves; the stripes become translucent, and the entire leaf rolls inward from the edges. Later, drying-out ascends upwards in the plant and includes leaf yellowing and dehydration, color alteration of the vascular bundles to a yellow-brown hue and then the appearance of red-brown stripes on the lower internode, the symptoms advancing to the fifth internode or further. With disease progression, the lower stem dries out (particularly at the internodes) and has a shrunken and hollow appearance, with dark yellow to brownish macerated pith and brownish-black vascular bundles.

Late wilt is caused by the soilborne fungus, *Harpophora maydis* (with synonyms: *Cephalosporium maydis* Samra, Sabet, & Hingorani and *Acremonium maydis*). *Harpophora* spp. are characterized by fast-growing, thin colonies with sickle-shaped conidia. Older hyphae are heavily pigmented, younger hyphae are nearly hyaline, and phialides are intermediate in pigmentation relative to the older and younger hyphae.

Attempts have been made to control *H. maydis* using chemical and biological methods with limited success. Some fungicides that were tested worked well in pots but failed in field experiments, while others achieved promising results. Since *H. maydis* is a poor saprophytic competitor, various attempts at biological control by inoculating corn seed with competitive or antagonistic organisms (*Macrophomina phaseolina, Trichurus spiralis, Bacillus subtilis, Pseudomonas fluorescens, Verticillium tricorpus*) have been evaluated; however, success on a field scale has not been demonstrated consistently. See Degani and Cernica, *Advances in Microbiology,* 2014, 4, 94-105. Another potential approach for controlling late wilt is using resistant germplasm. However, little is known regarding the genetic basis of late wilt resistance.

There is a need in corn breeding to identify corn germplasm that provides resistance to LW infection. There is also a need to develop polymorphic markers for monitoring and introgressing LW resistance alleles, and further develop agronomically elite corn lines comprising LW resistance for enhancing plant productivity.

SUMMARY

The present disclosure identifies genetic loci conferring LW resistance in corn, and provides molecular markers linked to these resistance loci. This disclosure further provides methods for introgressing resistance alleles of genetic loci conferring LW resistance into plant varieties previously lacking such alleles, thereby providing plants with LW resistance. The genetic loci, markers, and methods provided herein therefore allow for production of new varieties with enhanced LW resistance.

In one aspect, this disclosure provides a method of creating a population of corn plants or seeds comprising genotyping a first population of corn plants or seeds at one or more marker loci associated with and within about 10 cM of one or more LW resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; selecting from the first population one or more corn plants or seeds comprising one or more LW resistance alleles of the one or more marker loci; and producing from the selected one or more corn plants or seeds a second population of corn plants or seeds comprising the one or more LW QTLs.

In one aspect, this disclosure provides a method of introgressing an LW resistance QTL comprising crossing a first corn plant comprising an LW resistance QTL with a second corn plant of a different genotype to produce one or more progeny plants or seeds; and selecting a progeny plant or seed comprising an LW resistance allele of a polymorphic locus linked to the LW resistance QTL, where the polymorphic locus is within about 10 cM of any one of marker loci selected from the group consisting of SEQ ID NOs:1 to 51 and 256 to 264 and associated with one or more LW resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

In one aspect, this disclosure provides an LW resistant corn plant or seed comprising a combination of two or more, three or more, four or more, five or more, or six or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

In one aspect, this disclosure provides a method for selecting a corn plant or seed comprising isolating nucleic acids from a corn plant or seed; analyzing the nucleic acids to detect a polymorphic marker associated with and within 10 cM of an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; and selecting a corn plant or seed comprising the LW resistance QTL.

In one aspect, this disclosure provides a method comprising providing a set of corn seeds comprising one or more, two or more, three or more, four or more, five or more, or six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

In one aspect, this disclosure provides a method of growing a population of corn plants in a field plot, said method comprising planting a population of corn seeds comprising one or more, two or more, three or more, four or more, five or more, or six or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

BRIEF DESCRIPTION OF THE SEQUENCES

SEQ ID NOs:1 to 51 and 256 to 264 list sequences of exemplary SNP marker loci associated with an LW resistance QTL. Example resistant and susceptible alleles of these marker loci are listed in Table 4. SEQ ID NOs:52 to 255 list the sequences of exemplary primers and probes which can be used to detect the SNP marker loci of SEQ ID NOs:1 to 51 and 256 to 264.

DETAILED DESCRIPTION

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

As used herein, "plant" refers to a whole plant and/or progeny of the same. A progeny plant can be from any filial generation, e.g., $F_1$, $F_2$, $F_3$, $F_4$, $F_5$, $F_6$, $F_7$, etc. A "plant part" refers to any part of a plant, comprising a cell or tissue culture derived from a plant, plant components or organs (e.g., leaves, stems, roots, etc.), plant tissues, seeds, and plant cells. A plant cell is a biological cell of a plant, taken from a plant or derived through culture from a cell taken from a plant.

As used herein, a "corn plant" or "maize plant" refers to a plant of species Zea mays L and includes all plant varieties that can be bred with corn, including wild maize species.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed, or tissues from which new plants can be grown, or plant parts, such as leaves, stems, pollen, or cells that can be cultured into a whole plant.

As used herein, the phrase "associated with" or "linked to" refers to a recognizable and/or assayable relationship between two entities. For example, the phrase "associated with LW resistance" refers to a trait, locus, gene, allele, marker, phenotype, etc., or the expression thereof, the presence or absence of which can influence an extent, degree, and/or rate at which a plant or a part of interest thereof that has an LW resistance trait. As such, a marker is "associated with" a trait when it is linked to it and when the presence of the marker is an indicator of whether and/or to what extent the desired trait or trait form will occur in a plant/germplasm comprising the marker. Similarly, a marker is "associated with" an allele when it is linked to it and when the presence of the marker is an indicator of whether the allele is present in a plant/germplasm comprising the marker. For example, "a marker associated with a resistance allele" refers to a marker whose presence or absence can be used to predict whether and to what extent a plant will display an LW resistance phenotype.

As used herein, a "centimorgan" (cM) is a unit of measure of recombination frequency and genetic distance between two loci. One cM is equal to a 1% chance that a marker at one genetic locus will be separated from a marker at a second locus due to crossing over in a single generation.

As used herein, "closely linked" means that the marker or locus is within about 20 cM, 15 cM, 10 cM, 5 cM, 4 cM, 3 cM, 2 cM, 1 cM, 0.5 cM, or less than 0.5 cM of another marker or locus. For example, 20 cM means that recombination occurs between the marker and the locus with a frequency of equal to or less than about 20%.

As used herein, "locus" is a chromosome region or chromosomal region where a polymorphic nucleic acid, trait determinant, gene, or marker is located. A locus can represent a single nucleotide, a few nucleotides or a large number of nucleotides in a genomic region. The loci of this disclosure comprise one or more polymorphisms in a population (e.g., alternative alleles are present in some individuals).

As used herein, "allele" refers to an alternative nucleic acid sequence at a particular locus. The length of an allele can be as small as one nucleotide base. For example, a first allele can occur on one chromosome, while a second allele occurs on a second homologous chromosome, e.g., as occurs for different chromosomes of a heterozygous individual, or between different homozygous or heterozygous individuals in a population.

As used herein, "crossed," "cross," or "crossing" means to produce progeny via fertilization (e.g., cells, seeds, or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot et al., Marker-assisted Backcrossing: A Practical Example, in *Techniques Et Utilisations Des Marqueurs Moleculaires Les Colloques*, 72:45-56 (1995); and Openshaw et al., Marker-assisted Selection in Backcross Breeding, in Proceedings Of The Symposium "Analysis Of Molecular Marker Data," pp. 41-43 (1994). The initial cross gives rise to the $F_1$ generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "agronomically elite background" means any line that has resulted from breeding and selection for superior agronomic performance. Similarly, an "elite germplasm" or elite strain of germplasm is an agronomically superior germplasm. Numerous elite lines are available and known to those of skill in the art of corn breeding.

As used herein, "genotype" is the genetic constitution of an individual (or group of individuals) at one or more genetic loci, as contrasted with the observable trait (phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. The term "genotype" can also refer to determining the genetic constitution of an individual (or group of individuals) at one or more genetic loci.

As used herein, a "haplotype" is the genotype of an individual at a plurality of genetic loci. Typically, the genetic loci described by a haplotype are physically and genetically linked, e.g., in the same chromosome interval. A haplotype can also refer to a combination of SNP alleles located within a single gene.

As used herein, "marker assay" means a method for detecting a polymorphism at a particular locus using a particular method, e.g. measurement of at least one phenotype (such as seed color, flower color, or other visually detectable traits), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism can manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation can comprise, but is not limited to, one or more nucleotide base changes, the insertion of one or more nucleotides or the deletion of one or more nucleotides. A polymorphism can arise from random processes in nucleic acid replication, through mutagenesis, as a result of mobile genomic elements, from copy number variation and during the process of meiosis, such as unequal crossing over, genome duplication, and chromosome breaks and fusions. The variation can be commonly found or can exist at low frequency within a population, the former having greater utility in general plant breeding and the latter can be associated with rare but important phenotypic variation. Useful polymorphisms can include a single nucleotide polymorphisms (SNP), an insertion or deletion in DNA sequence (indel), a simple sequence repeats of DNA sequence (SSR), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, microRNA, small interfering RNA, a tolerance locus, a satellite marker, a transgene, mRNA, double-stranded RNA, a transcriptional profile, and a methylation pattern can also comprise a polymorphism. In addition, the presence, absence, or variation in copy number of the preceding can comprise a polymorphism.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker," "molecular marker," or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of markers and integrated genetic maps have been developed for corn (e.g., the UMC 98 map, the Nested Association Mapping (NAM) map, the Intermated B73/Mo17 (IBM2) Neighbors 2008 genetic map, and the LHRF Gnp2004 map. See maizegdb.org/data_center/map for more). All markers are used to define a specific locus in corn genomes. Large numbers of these markers have been mapped. See maizegdb.org/data_center/marker. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed.

Molecular markers have been widely used to determine genetic composition in corn. In an aspect, markers used herein exhibit LOD scores of 2 or greater, 3 or greater, 4 or greater, 5 or greater, 6 or greater, 7 or greater, 8 or greater, or 9 or greater with an associated trait of interest (e.g., LW resistance), measuring using a method known in the art such as Qgene Version 2.23 (1996) and default parameters. Without being limiting, examples of molecular markers and molecular marker systems include SNPs, indels, RFLPs, SSRs, restriction site-associated DNA (RAD), diversity array technology (DArT), and genotyping by sequencing (GBS).

As used herein, "linkage disequilibrium" (LD) refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. Linkage disequilibrium can be measured using any one of the methods provided in Hedrick, Gametic disequilibrium measures: proceed with caution. *Genetics*, 117:331-41(1987). The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time.

As used herein, a "genetic map" is the relationship of genetic linkage among loci on one or more chromosomes (or linkage groups) within a given species, generally depicted in a diagrammatic or tabular form. Genetic mapping is the process of defining the linkage relationships of loci through the use of genetic markers, populations segregating for the markers, and standard genetic principles of recombination frequency. A genetic map location is a location on a genetic map relative to surrounding genetic markers on the same linkage group where a specified marker can be found within a given species. In contrast, a "physical map" of the genome refers to absolute distances (for example, measured in base pairs or isolated and overlapping contiguous genetic fragments, e.g., contigs). In general, the closer two markers or genomic loci are on the genetic map, the closer they lie to one another on the physical map. A physical map of the genome does not take into account the genetic behavior (e.g., recombination frequencies) between different points on the physical map. A lack of precise proportionality between genetic distances and physical distances can exist due to the fact that the likelihood of genetic recombination is not uniform throughout the genome; some chromosome regions are cross-over "hot spots," while other regions demonstrate only rare recombination events, if any. Genetic mapping variability can also be observed between different populations of the same crop species. In spite of this variability in the genetic map that can occur between populations, genetic map and marker information derived from one population generally remains useful across multiple populations in identification of plants with desired traits, counter-selection of plants with undesirable traits and in MAS breeding. As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that this disclosure be limited to any particular mapping populations, use of any particular software, or any particular set of software parameters to determine linkage of a particular marker or haplotypes with a desired phenotype. It is well within the ability of one of ordinary skill in the art to extrapolate the novel features described herein to any gene pool or population of interest, and using any particular software and software parameters. Indeed, observations regarding genetic markers and haplotypes in populations in addition to those described herein are readily made using the teaching of the present disclosure.

As used herein, "selecting" or "selection" in the context of marker-assisted selection or breeding refer to the act of picking or choosing desired individuals, normally from a population, based on certain pre-determined criteria.

As used herein, "primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers can be provided in double-stranded form, though the single-stranded form is more typically used. A primer can further contain a detectable label (e.g., a 5' end label).

As used herein, "probe" refers to an oligonucleotide (synthetic or occurring naturally) that is complementary (though not necessarily fully complementary) to a polynucleotide of interest and forms a duplex structure by hybridization with at least one strand of the polynucleotide of interest. Typically, probes are oligonucleotides from 10 to 50 nucleotides in length, but longer or shorter sequences can be employed. A probe can further contain a detectable label.

As used herein, a "population of plants" or a "population of seeds" means a set comprising any number, at least two, of individuals, objects, or data from which samples are taken for evaluation. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants or seeds. The population members need not be identical to the population members selected for use in subsequent cycles of analyses or those ultimately selected to obtain final progeny plants or seeds. Often, a population of plants or seeds is derived from a single biparental cross, but can also derive from two or more crosses between the same or different parents. Although a population of plants or seeds can comprise any number of individuals, those of skill in the art will recognize that plant breeders commonly use population sizes ranging from one or two hundred individuals to several thousand, and that the highest performing 5% to 20% of a population is what is commonly selected to be used in subsequent crosses in order to improve the performance of subsequent generations of the population.

As used herein, "cultivar" and "variety" are used synonymously and mean a group of plants within a species (e.g., *Z. mays* L.) that share certain genetic traits that separate them from other possible varieties within that species. Corn cultivars can be inbreds or hybrids, though commercial corn cultivars are mostly hybrids to take advantage of hybrid vigor. Individuals within a corn hybrid cultivar are homogeneous, nearly genetically identical, with most loci in the heterozygous state.

As used herein, the term "inbred" means a line that has been bred for genetic homogeneity.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines.

As used herein, "introgression" refers to the transmission of a desired allele of a genetic locus from one genetic background to another.

As used herein, the term "chromosome interval" or "chromosomal interval" designates a contiguous linear span of genomic DNA that resides on a single chromosome.

As used herein, "flanked by," when used to describe a chromosomal interval, refers to two loci physically surrounding the chromosomal interval, with one locus on each side of the chromosomal interval. As referenced herein, a chromosomal interval flanked by two marker loci includes the two marker loci.

As used herein, a "resistant allele" or "resistance allele" is an allele at a particular locus that confers, or contributes to, LW resistance, or alternatively, is an allele that allows the identification of plants that comprise LW resistance. A resistant allele of a marker is a marker allele that segregates with LW resistance, or alternatively, segregates with LW susceptibility, therefore providing the benefit of identifying plants having LW susceptibility. A resistant allelic form of a chromosome interval is a chromosome interval that includes a nucleotide sequence that contributes to LW resistance at one or more genetic loci physically located in the chromosome interval.

As used herein, "genetic element" or "gene" refers to a heritable sequence of DNA, e.g., a genomic sequence, with functional significance. The term "gene" can also be used to refer to, e.g., a cDNA and/or an mRNA encoded by a genomic sequence, as well as to that genomic sequence.

As used herein, the terms "phenotype," or "phenotypic trait," or "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "resistance" and "enhanced resistance" are used interchangeably herein and refer to any type of increase in resistance, or any type of decrease in susceptibility. A plant or plant variety exhibiting resistance need not possess absolute or complete resistance. Instead, a plant or plant variety with "enhanced resistance" will have a level of resistance which is higher than that of a comparable susceptible plant or variety. The level of LW resistance can be determined based on disease ratings as determined in Example 1. Briefly, resistance to LW infection of corn plants is scored using an LW resistance scale, wherein LW resistance is measured by rating the infection severity on a scale of 1 to 9 (Table 1).

As used herein, "quantitative trait locus" (QTL) or "quantitative trait loci" (QTLs) refer to a genetic domain that effects a phenotype that can be described in quantitative terms and can be assigned a "phenotypic value" which corresponds to a quantitative value for the phenotypic trait.

As used herein, "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "late wilt" or "LW" refers to a plant disease caused by the fungal pathogen *Harpophora maydis*, which is also sometimes referred to as *Cephalosporium maydis* or *Acremonium maydis*.

As used herein, "field plot" refers to a location that is suitable for growing corn. The location can be indoors (e.g., a greenhouse or a growth chamber) or outdoors; irrigated or non-irrigated; in the ground or in a container that holds soil.

As used herein, a "planting season" is the length of time, typically about 90-120 days, in which corn can be grown from seed to maturity. One skilled in the art would recognize that a "planting season" could be significantly shorter or longer than about 90-120 days depending on the corn variety being grown and environmental conditions.

As used herein, "transgenic" means a plant or seed whose genome has been altered by the stable integration of recombinant DNA. A transgenic line includes a plant regenerated from an originally-transformed plant cell and progeny transgenic plants from later generations or crosses of a transformed plant.

As used herein, "haploid" means a line that has had its normal chromosome complement reduced by half, typically by pollinating an ear with pollen from a haploid inducing line. In corn, haploid refers to an individual plant or seed that has a haploid chromosome complement where n=10, instead of the normal diploid chromosome complement where 2n=20. A "doubled haploid" refers to a haploid line (n=10) that has been induced, typically via chemical means, to double its chromosome complement and return to a diploid state (2n=20) that is homozygous at all loci within the genome.

As used herein, "yield penalty" refers to a reduction of seed yield in a line correlated with or caused by the presence of an LW resistance allele or LW resistance QTL as compared to a line that does not contain that LW resistance allele or LW resistance QTL.

As used herein, "seed yield" can refer to a measure of crop production such as test weight, seed number per plant, seed weight, seed number per unit area (i.e. seeds, or weight of seeds, per acre), bushels per acre, tons per acre, kilograms per hectare, or quintals per hectare.

*H. maydis* can cause a late-season severe stalk rot of widespread incidence and severity. Yield losses of up to 40 percent have been reported. Root tips of infected corn plants are stained red during early stages of infection, but above ground parts generally remain symptomless until tasseling when a rapid wilting of lower leaves progresses upward. Leaves appear streaked as tissue between the veins becomes dull green and then chlorotic before eventually rolling inward and appearing scorched while retaining somewhat of a green color. Yellow to reddish brown streaks appear on the basal internodes of the stalk. Wilting can occur suddenly so that non-infected ("escapes") or resistant plants are quite distinct. Stalks dry and have a shrunken and hollow appearance with dark yellow to brownish macerated pith and brownish-black vascular bundles. Lower parts of infected stalks become dry, shrunken and hollow.

*H. maydis* has no specific moisture requirements. Initially, this fungus grows superficially on corn roots, producing hyphae with short, thick-walled, swollen cells. Infection in corn occurs through the roots or mesocotyl. It was reported that three irrigations at an interval of 8 hours after inoculation supported maximum rate of disease development. As plants mature, fewer plants are infected, and they become immune about 50 days after planting.

After penetration, *H. maydis* colonizes xylem tissue and is rapidly translocated to the upper parts of the plant. When infections are severe, the fungus colonizes the kernels, resulting in seedborne dissemination and also causes seed rot and damping off.

No perfect (sexual) state has been identified for *H. maydis*. It can remain viable in the soil for several years in the absence of a host, and has been reported to persist on corn stubble for 12 to 15 months. Inoculum survival in soil is generally poor and restricted to the top 20 cm of soil. Although it is a weakly competitive saprophyte, the production of sclerotia in infested host debris ensures its long-term survival. The only reported hosts of *H. maydis* are corn, lupine, and cotton.

*H. maydis*-caused late wilt is often associated with infection by secondary invaders such as *H. acremonium, Sclerotium bataticola, Fusarium verticillioides* and various bacterial rots to present a "stalk rot complex". These saprobic organisms cause the stem symptoms to become more severe. Fewer ears are produced, and kernels that form are poorly developed and may be infected with the pathogen. Seed quantity is correlated negatively to disease severity.

A corn plant or seed provided herein possesses one or more LW resistance QTLs and/or one or more LW resistance alleles that confer enhanced resistance to LW compared to a corn plant or seed that lacks the one or more LW resistance QTLs and/or one or more LW resistance alleles. Further, a corn plant or seed provided herein provided herein does not suffer a yield penalty when grown in the absence of LW spores, conidia, and/or mycelia.

In an aspect, a corn plant or seed provided herein is a *Zea mays* L. corn plant or seed. In another aspect, a corn plant or seed provided herein is a *Zea mays* ssp. *mays* corn plant or seed. In yet another aspect, a corn plant or seed provided herein is a domesticated line, cultivar, or variety of corn plant or seed. In another aspect, a corn plant or seed provided herein is a sweet corn plant or sweet corn seed.

In an aspect, this disclosure provides quantitative trait loci (QTLs) that exhibit significant co-segregation with LW resistance. The QTLs of this disclosure can be tracked during plant breeding or introgressed into a desired genetic background in order to provide plants exhibiting enhanced LW resistance and one or more other beneficial traits. As an example, this disclosure identifies QTL intervals that are associated with LW resistance in corn varieties CV131061, CV806292, CV137694, and CV138811.

In an aspect, this disclosure provides molecular markers closely linked to one or more LW resistance QTLs and methods of using these markers for detection of and selection for LW resistance. An aspect of this disclosure includes specific markers and their resistance alleles, chromosome intervals comprising the markers, and methods of detecting markers genetically linked to LW resistance to identify plant lines with enhanced LW resistance. For example, one aspect of this disclosure provides a chromosome interval associated with LW resistance which is flanked by any two of marker loci SEQ ID NOs: 1 to 3. Another example of this disclosure provides a chromosome interval associated with LW resistance, where the interval is flanked by marker loci SEQ ID NOs: 47 and 48. Another example of this disclosure provides a chromosome interval associated with LW resistance which is flanked by marker loci SEQ ID NOs: 41 and 42. Another example of this disclosure provides a chromosome interval associated with LW resistance which is flanked by any two of marker loci SEQ ID NOs: 8 to 17, 21 to 23, and 26 to 38. Another example of this disclosure provides a chromosome interval associated with LW resistance which is flanked by marker loci SEQ ID NOs: 45 and 46. Another example of this disclosure provides a chromosome interval associated with LW resistance which is flanked by marker loci SEQ ID NOs: 24 and 25. Another example of this disclosure provides a chromosome interval associated with LW resistance which is flanked by any two of marker loci SEQ ID NOs: 4 to 7 and 18 to 20. Another example of this disclosure provides a chromosome interval associated with LW resistance which is flanked by marker loci SEQ ID NOs: 49 and 50. Further provided are chromosome intervals associated with LW resistance listed in Table 7 (as defined by two flanking public markers).

Also provided herein are markers, e.g., SEQ ID NOs:1 to 51 and 256 to 264 and those that are within about 20 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 15 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 10 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 5 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 4 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 3 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 2 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 1 cM or less from these SEQ ID NOs, that are useful for tracking LW resistant alleles and can be used in MAS breeding programs to produce plants with enhanced LW resistance.

Also provided herein are markers, e.g., SEQ ID NOs:1 to 51 and 256 to 264 and those that are within about 0.5 cM or less from these SEQ ID NOs, that are useful for tracking LW resistant alleles and can be used in MAS breeding programs to produce plants with enhanced LW resistance.

This disclosure further provides methods of using the markers identified herein to introgress loci associated with LW resistance into LW susceptible plants. As an example, one skilled in the art can use this disclosure to create a novel corn plant or seed with LW resistance by crossing a donor line comprising a QTL provided herein with any desired recipient line, with or without MAS.

In another aspect, this disclosure further provides methods for introgressing multiple LW resistance QTLs identified herein to generate an enhanced LW resistant population of corn plants or seeds.

In an aspect, this disclosure provides a method of creating a population of corn plants or seeds, where the method comprises the steps of: (a) genotyping a first population of corn plants or seeds at one or more marker loci associated with one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; (b) selecting from the first population one or more corn plants or seeds comprising one or more LW resistance alleles of the one or more marker loci; and (c) producing from the selected one or more corn plants or seeds a second population of corn plants or seeds comprising one or more LW QTLs.

In an aspect, this disclosure provides a method of creating a population of corn plants or seeds, which method comprising the steps of: (a) genotyping a first population of corn plants, the population comprising at least one allele associated with LW resistance, wherein the LW resistance allele is associated with a marker selected from the group consisting of SEQ ID NOs:1 to 51 and 256 to 264; (b) selecting from the first population one or more corn plants or seeds comprising the LW resistance allele; and (c) producing from the selected corn plants or seeds a second population of corn plants or seeds comprising the at least one LW resistance allele.

In an aspect, this disclosure provides a method for introgressing a resistance allele of a locus conferring LW resistance, which method comprising the steps of: (a) crossing a first corn plant with a second corn plant, wherein the first corn plant comprises the resistance allele, wherein the LW resistance allele is associated with a marker selected from the group consisting of SEQ ID NOs:1 to 51 and 256 to 264; (b) genotyping a progeny corn plant or seed from the cross using a marker associated with the resistance allele; and (c) selecting a progeny plant or seed comprising the resistance allele.

In an aspect, this disclosure provides a method for introgressing an LW resistance QTL, which method comprising the steps of: (a) crossing a first corn plant comprising an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, with a second corn plant of a different genotype to produce one or more progeny plants or seeds; (b) assaying the one or more progeny plants or seeds at a marker locus associated with the LW resistance QTL; and (c) selecting a progeny plant or seed comprising the LW resistance QTL.

In an aspect, this disclosure provides a method for creating a population of corn plants or seeds with LW resistance, which method comprising the steps of: (a) concurrently detecting in a first population of corn plants or seeds the presence of a combination of two or more, three or more, four or more, five or more, or six or more introgressed LW resistance loci selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; (b) selecting from the first population one or more corn plants or seed comprising the one or more, two or more, three or more, four or more, five or more, or six or more introgressed LW resistance QTLs; and (c) producing a population of offspring from the selected one or more corn plants or seeds. In an aspect, a method comprises concurrent detection of one or more molecular markers located in at least one chromosome interval flanked by: any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15, and gpm84; any two of the marker loci selected from the group consisting of SEQ ID NO: 51, umc1380, and bcd386b; marker loci SEQ ID NOs: 257 and 257; or any two of marker loci selected from the group consisting of SEQ ID NOs: 44, and 258 to 264.

In an aspect, a method comprises concurrently detecting at least two, at least three, at least four, at least five, or at least six LW resistance QTLs selected from the group consisting of LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

In an aspect, this disclosure provides a method of producing a corn plant with enhanced LW resistance, which method comprising the steps of: (a) crossing a first corn plant comprising an LW resistance QTL with a second corn plant of a different genotype to produce one or more progeny plants or seeds; (b) selecting a progeny plant or seed comprising an LW resistance allele of a polymorphic locus linked to an LW resistance QTL, wherein a polymorphic locus is in a chromosomal segment flanked by: any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15, and gpm84; any two of the marker loci selected from the group consisting of SEQ ID NO: 51, umc1380, and bcd386b; marker loci SEQ ID NOs: 257 and 257; or any two of marker loci selected from the group consisting of SEQ ID NOs: 44, and 258 to 264; (c) crossing the selected progeny plant with itself or the second corn plant to produce one or more further progeny plants or seeds; and (d) selecting a further progeny plant or seed comprising the LW resistance allele. In an aspect, the further progeny plant in step (d) is an $F_2$ to $F_7$ progeny plant. In another aspect, the further progeny plant in step (d) comprises 2 to 7 generations of backcrossing. In yet another aspect, a method comprises using marker-assisted selection to select an LW resistance allele in at least one polymorphic locus selected from the group consisting of SEQ ID NOs:1 to 51 and 256 to 264.

In an aspect, this disclosure provides a method of obtaining a corn plant or seed with enhanced LW resistance, which method comprises the steps of: (a) detecting in a population of corn plants or seeds a plant or seed comprising an LW resistance allele at a polymorphic locus in a chromosomal segment flanked by any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15, and gpm84; any two of the marker loci selected from the group consisting of SEQ ID NO: 51, umc1380, and bcd386b; marker loci SEQ ID NOs: 257 and 257; or any two of marker loci selected from the group consisting of SEQ ID NOs: 44, and 258 to 264; and (b) selecting the plant or seed from the population based on the presence of the LW resistance allele.

In an aspect, this disclosure provides a method of producing a corn plant with enhanced LW resistance, which method comprising the steps of: (a) crossing a first corn plant comprising an LW resistance haplotype with a second corn plant of a different genotype to produce one or more progeny plants or seeds; (b) selecting a progeny plant or seed based on the presence of the LW resistance haplotype, wherein the haplotype comprises resistance alleles of two or more polymorphic loci in a chromosomal interval flanked by: any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15, and gpm84; any two of the marker loci selected from the group consisting of SEQ ID NO: 51, umc1380, and bcd386b; marker loci SEQ ID NOs: 257 and 257; or any two of marker loci selected from the group consisting of SEQ ID NOs: 44, and 258 to 264.

In an aspect, this disclosure provides a method of obtaining a corn plant or seed with enhanced LW resistance, which method comprising the steps of: (a) detecting in a population of corn plants or seeds a plant or seed comprising an LW resistance haplotype, wherein the haplotype comprises resistance alleles of two or more polymorphic loci in a chromosomal interval flanked by: any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15, and gpm84; any two of the marker loci selected from the group consisting of SEQ ID NO: 51, umc1380, and bcd386b; marker loci SEQ ID NOs: 257 and 257; or any two of marker loci selected from the group consisting of SEQ ID NOs: 44, and 258 to 264; and (b) selecting a plant or seed from the population based on the presence of the LW resistance haplotype. In another aspect, an LW resistance haplotype comprises resistance alleles of two or more polymorphic loci selected from the group consisting of SEQ ID NOs:1 to 51 and 256 to 264.

In an aspect, this disclosure provides a method of obtaining a corn plant or seed with enhanced LW resistance, which method comprising the steps of: (a) detecting in a population of corn plants or seeds a plant or seed comprising an LW resistance haplotype, wherein the haplotype comprises resistance alleles of two or more polymorphic loci in a chromosomal interval flanked by: any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15, and gpm84; any two of the marker loci selected from the group consisting of SEQ ID NO: 51, umc1380, and bcd386b; marker loci SEQ ID NOs: 257 and 257; or any two of marker loci selected from the group consisting of SEQ ID NOs: 44, and 258 to 264; and (b) selecting a plant or seed from the population based on the presence of the LW resistance haplotype. In yet another aspect, an LW resistance haplotype comprises resistance alleles of two or more polymorphic loci selected from the group consisting of SEQ ID NOs: 1 to 51 and 256 to 264.

In an aspect, this disclosure provides a method for selecting a corn plant or seed, which method comprising the steps of: (a) isolated nucleic acids from a corn plant or seed; (b) analyzing the nucleic acids to detect a polymorphic marker associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; and (c) selecting a corn plant or seed comprising the LW resistance QTL.

In an aspect, this disclosure provides a method for selecting a corn plant or seed, which method comprising the steps of: (a) detecting in a population of corn plants or seeds a corn plant or seed comprising an LW resistance allele of a marker locus associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; and (b) selecting a corn plant or seed comprising the LW resistance allele.

In an aspect, this disclosure provides a method for evaluating a collection of corn germplasm, which method comprising the steps of: (a) obtaining a collection of corn germplasm; (b) isolating nucleic acids from each germplasm; (c) assaying the nucleic acids for one or more markers linked to an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; and (d) selecting germplasm comprising an LW resistance QTL based on the marker assay.

In an aspect, a method provided herein comprises genotyping by a marker assay. As an example, a method provided herein comprises marker-assisted selection. As another example, a method provided herein comprises assaying a SNP marker. In yet another example, a method provided herein comprises the use of an oligonucleotide probe. In a further example, a method provided herein comprises using an oligonucleotide probe adjacent to a polymorphic nucleotide position in a marker locus being genotyped.

As an example, a corn plant or seed provided herein can be an inbred, a hybrid, a transgenic, a haploid, a doubled haploid, or in an agronomically elite background. These groups are not mutually exclusive, and a corn plant or seed could be in two or more groups (e.g., a plant could be a transgenic hybrid, another plant could be an inbred doubled haploid, etc.).

In an aspect, a method provided herein comprises genotyping a corn plant or seed at a polymorphic marker locus within about 20 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 15 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 10 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 5 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 4 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 3 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 2 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 1 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a polymorphic marker locus within about 0.5 cM or less of any one of marker loci SEQ ID NOs:1 to 51 and 256 to 264. In an aspect, this disclosure provides a method comprising genotyping a polymorphic locus or a combination of loci selected from the group consisting of SEQ ID NOs:1 to 51 and 256 to 264.

In an aspect, a method provided herein comprises genotyping a corn plant or seed at a marker locus associated with LW resistance QTL LW_1.01, which marker locus is located in a chromosomal interval flanked by any two of the marker loci selected from the group consisting of SEQ ID NOs: 1 to 3. In another aspect, a method provided herein comprises genotyping a corn plant or seed at a marker locus associated with LW resistance QTL LW_1.01, which marker locus is located in a chromosomal interval flanked by cl15737_2 and TIDP7101. In an aspect, a method provided herein comprises genotyping a corn plant or seed at a marker locus associated with LW resistance QTL LW_1.01, which marker locus is located in a chromosomal interval flanked by any two of the marker loci selected from the group consisting of SEQ ID NOs: 1 to 3, cl15737_2, and TIDP7101.

In an aspect, a method provided herein comprises genotyping a corn plant or seed at a marker locus associated with LW resistance QTL LW_1.02, which marker locus is located in a chromosomal interval flanked by marker loci SEQ ID NOs: 47 and 48. In another aspect, a method provided herein comprises genotyping a corn plant or seed at a marker locus associated with LW resistance QTL LW_1.02, which marker locus is located in a chromosomal interval flanked by gpm748b and mmp66. In an aspect, a method provided herein comprises genotyping a corn plant or seed at a marker locus associated with LW resistance QTL LW_1.02, which marker locus is located in a chromosomal interval flanked by any two of the marker loci selected from the group consisting of SEQ ID NOs: 47 and 48, gpm748b, and mmp66.

In an aspect, a method provided herein comprises genotyping a corn plant or seed at a marker locus associated with LW resistance QTL LW_1.03, which marker locus is located in a chromosomal interval flanked by marker loci SEQ ID NOs: 41 and 42. In another aspect, a method provided herein comprises genotyping a corn plant or seed at a marker locus associated with LW resistance QTL LW_1.03, which marker locus is located in a chromosomal interval flanked by umc1514 and umc1917. In an aspect, a method provided herein comprises genotyping a corn plant or seed at a marker locus associated with LW resistance QTL LW_1.03, which marker locus is located in a chromosomal interval flanked by any two of the marker loci selected from the group consisting of SEQ ID NOs: 41 and 42, umc1514, and umc1917.

In an aspect, a method provided herein comprises genotyping a corn plant or seed at a marker locus associated with LW resistance QTL LW_1.04, which marker locus is located in a chromosomal interval flanked by any two of the marker loci selected from the group consisting of SEQ ID NO: 43, isu92b, and bnlg100.

In an aspect, a method provided herein comprises genotyping a corn plant or seed at a marker locus associated with LW resistance QTL LW_2.01, which marker locus is located in a chromosomal interval flanked by any two of the marker loci selected from the group consisting of SEQ ID NOs: 8 to 17, 21 to 23, 26 to 38. In another aspect, a method provided herein comprises genotyping a corn plant or seed at a marker locus associated with LW resistance QTL LW_2.01, which marker locus is located in a chromosomal interval flanked by TIDP5226 and IDP682. In an aspect, a method provided herein comprises genotyping a corn plant or seed at a marker locus associated with LW resistance QTL LW_2.01, which marker locus is located in a chromosomal interval flanked by any two of the marker loci selected from the group consisting of SEQ ID NOs: 8 to 17, 21 to 23, 26 to 38, TIDP5226, and IDP682.

In another aspect, a method provided herein comprises genotyping a corn plant or seed at a marker locus associated with LW resistance QTL LW_3.01, which marker locus is located in a chromosomal interval flanked by any two marker loci selected from the group consisting of IDP6785, gpm358, SEQ ID NOs: 256 and 257.

In an aspect, a method provided herein comprises genotyping a corn plant or seed at a marker locus associated with LW resistance QTL LW_3.02, which marker locus is located in a chromosomal interval flanked by any two of the marker loci selected from the group consisting of SEQ ID NO: 44, 258 to 264, TIDP6314, and IDP73.

In an aspect, a method provided herein comprises genotyping a corn plant or seed at a marker locus associated with LW resistance QTL LW_3.03, which marker locus is located in a chromosomal interval flanked by marker loci SEQ ID NOs: 45 and 46. In another aspect, a method provided herein comprises genotyping a corn plant or seed at a marker locus associated with LW resistance QTL LW_3.03, which marker locus is located in a chromosomal interval flanked by TIDP4628 and agrr43b. In an aspect, a method provided herein comprises genotyping a corn plant or seed at a marker locus associated with LW resistance QTL LW_3.03, which marker locus is located in a chromosomal interval flanked by any two of the marker loci selected from the group consisting of SEQ ID NOs: 45 and 46, TIDP4628, and agrr43b.

In an aspect, a method provided herein comprises genotyping a corn plant or seed at a marker locus associated with LW resistance QTL LW_4.01, which marker locus is located in a chromosomal interval flanked by marker loci SEQ ID NOs: 24 and 25. In another aspect, a method provided herein comprises genotyping a corn plant or seed at a marker locus associated with LW resistance QTL LW_4.01, which marker locus is located in a chromosomal interval flanked by TIDP6171 and umc49d. In an aspect, a method provided herein comprises genotyping a corn plant or seed at a marker locus associated with LW resistance QTL LW_4.01, which marker locus is located in a chromosomal interval flanked by any two of the marker loci selected from the group consisting of SEQ ID NOs: 24 and 25, TIDP6171 and umc49d.

In an aspect, a method provided herein comprises genotyping a corn plant or seed at a marker locus associated with LW resistance QTL LW_4.02, which marker locus is located in a chromosomal interval flanked by any two of the marker loci selected from the group consisting of SEQ ID NOs: 4 to 7, 18 to 20. In another aspect, a method provided herein comprises genotyping a corn plant or seed at a marker locus associated with LW resistance QTL LW_4.02, which marker locus is located in a chromosomal interval flanked by c142326_1 and IDP498. In an aspect, a method provided herein comprises genotyping a corn plant or seed at a marker locus associated with LW resistance QTL LW_4.02, which marker locus is located in a chromosomal interval flanked by any two of the marker loci selected from the group consisting of SEQ ID NOs: 4 to 7, 18 to 20, c142326_1, and IDP498.

In another aspect, a method provided herein comprises genotyping a corn plant or seed at a marker locus associated with LW resistance QTL LW_5.01, which marker locus is located in a chromosomal interval flanked by phm5359 and npi75a.

In an aspect, a method provided herein comprises genotyping a corn plant or seed at a marker locus associated with LW resistance QTL LW_5.02, which marker locus is located in a chromosomal interval flanked by marker loci SEQ ID NOs: 49 and 50. In another aspect, a method provided herein comprises genotyping a corn plant or seed at a marker locus associated with LW resistance QTL LW_5.02, which marker locus is located in a chromosomal interval flanked by ole3 and umc43. In an aspect, a method provided herein comprises genotyping a corn plant or seed at a marker locus associated with LW resistance QTL LW_5.02, which marker locus is located in a chromosomal interval flanked by any two of the marker loci selected from the group consisting of SEQ ID NOs: 49 and 50, ole3, and umc43.

In another aspect, a method provided herein comprises genotyping a corn plant or seed at a marker locus associated with LW resistance QTL LW_6.01, which marker locus is located in a chromosomal interval flanked by pg11 and gpm674c.

In an aspect, a method provided herein comprises genotyping a corn plant or seed at a marker locus associated with LW resistance QTL LW_7.01, which marker locus is located in a chromosomal interval flanked by any two of the marker loci selected from the group consisting of SEQ ID NO: 39, prp4, and IDP4953.

In an aspect, a method provided herein comprises genotyping a corn plant or seed at a marker locus associated with LW resistance QTL LW_8.01, which marker locus is located in a chromosomal interval flanked by any two of the marker loci selected from the group consisting of SEQ ID NO: 40, gst15, and gpm84.

In an aspect, a method provided herein comprises genotyping a corn plant or seed at a marker locus associated with LW resistance QTL LW_10.01, which marker locus is located in a chromosomal interval flanked by any two of the marker loci selected from the group consisting of SEQ ID NO: 51, umc1380, and bcd386b.

In a further aspect, a method provided herein comprises genotyping a corn plant or seed at a marker locus located in a chromosomal interval flanked by any two of marker loci SEQ ID NOs: 1 to 3; marker loci SEQ ID NOs: 47 and 48; marker loci SEQ ID NOs: 41 and 42; any two of marker loci SEQ ID NOs: 8 to 17, 21 to 23, and 26 to 38; marker loci SEQ ID NOs: 45 and 46; marker loci SEQ ID NOs: 24 and 25; any two of marker loci SEQ ID NOs: 4 to 7 and 18 to 20; marker loci SEQ ID NOs: 49 and 50 marker loci SEQ ID NOs: 257 and 257; or any two of marker loci SEQ ID NOs: 44, and 258 to 264.

In another aspect, a method provided herein comprises genotyping a corn plant or seed by detecting a haplotype. In one aspect, a haplotype comprises an LW resistance allele at one or more, two or more, three or more, four or more, or five or more of marker loci SEQ ID NO: 1 to 51. In another aspect, a haplotype is selected from Table 2.

In an aspect, a corn plant or seed comprising LW resistance QTLs or LW resistant alleles provided herein exhibits intermediate resistance to LW infection from *H. maydis*. In another aspect, a corn plant or seed comprising LW resistance QTLs or LW resistant alleles provided herein exhibits at least mild resistance (e.g., LW resistance score of ≤5; see Table 1) to LW infection from *H. maydis*. In a further aspect, a corn plant or seed comprising LW resistance QTLs or LW resistant alleles provided herein exhibits resistance (e.g., LW resistance score of ≤3; see Table 1) to LW infection from *H. maydis*. In another aspect, a corn plant or seed comprising LW resistance QTLs or LW resistant alleles provided herein exhibits high resistance (e.g., LW resistance score of 1; see Table 1) to LW infection from *H. maydis*.

As used herein, a "low LW stress condition" refers to a condition where very few to no LW susceptible corn plants in a field plot (e.g., less than 10%) exhibit signs of LW infection. Signs of LW infection can include: dry stalk having a shrunken and hollow appearance with dark yellow to brownish macerated pith and brownish-black vascular bundles.

As used herein, a "high LW stress condition" refers to a condition where a plurality of LW susceptible corn plants in a field plot (e.g., more than 70%) exhibit signs of LW infection.

As an example, an LW resistance QTL or LW resistance allele provided herein does not confer a yield penalty under a low LW stress condition. In another example, a combination of two or more, three or more, four or more, five or more, or six or more LW resistance QTLs provided herein does not confer a yield penalty under a low LW stress condition.

In another aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of the LW rating score compared to a corn plant or seed without the one or more LW resistance QTLs under a similar growth condition (e.g., a high LW stress condition). In further aspects, a corn plant or seed exhibits a reduction of LW rating score of about 0.25 or more. In further aspects, a corn plant or seed exhibits a reduction of LW rating score of about 0.5 or more. In further aspects, a corn plant or seed exhibits a reduction of LW rating score of about 0.75 or more. In further aspects, a corn plant or seed exhibits a reduction of LW rating score of about 1 or more. In further aspects, a corn plant or seed exhibits a reduction of LW rating score of about 1.5 or more. In further aspects, a corn plant or seed exhibits a reduction of LW rating score of about 2 or more. In further aspects, a corn plant or seed exhibits a reduction of LW rating score of about 2.5 or more. In further aspects, a corn plant or seed exhibits a reduction of LW rating score of about 3 or more. In further aspects, a corn plant or seed exhibits a reduction of LW rating score of about 3.5 or more. In further aspects, a corn plant or seed exhibits a reduction of LW rating score of about 4 or more. In further aspects, a corn plant or seed exhibits a reduction of LW rating score of about 4.5 or more. In further aspects, a corn plant or seed exhibits a reduction of LW rating score of about 5 or more. In further aspects, a corn plant or seed exhibits a reduction of LW rating score of about 5.5 or more. In further aspects, a corn plant or seed exhibits a reduction of LW rating score of about 6 or more. In further aspects, a corn plant or seed exhibits a reduction of LW rating score of about 6.5 or more. In further aspects, a corn plant or seed exhibits a reduction of LW rating score of about 7 or more. In further aspects, a corn plant or seed exhibits a reduction of LW rating score of about or 7.5 or more.

In another aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of the LW rating score compared to a corn plant or seed without the two or more LW resistance QTLs under a similar growth condition (e.g., a high LW stress condition). In further aspects, a corn plant or seed exhibits a reduction of LW rating score of about 0.25 or more. In further aspects, a corn plant or seed exhibits a reduction of LW rating score of about 0.5 or more. In further aspects, a corn plant or seed exhibits a reduction of LW rating score of about 0.75 or more. In further aspects, a corn plant or seed exhibits a reduction of LW rating score of about 1 or more. In further aspects, a corn plant or seed exhibits a reduction of LW rating score of about 1.5 or more. In further aspects, a corn plant or seed exhibits a reduction of LW rating score of about 2 or more. In further aspects, a corn plant or seed exhibits a reduction of LW rating score of about 2.5 or more. In further aspects, a corn plant or seed exhibits a reduction of LW rating score of about 3 or more. In further aspects, a corn plant or seed exhibits a reduction of LW rating score of about 3.5 or more. In further aspects, a corn plant or seed exhibits a reduction of LW rating score of about 4 or more. In further aspects, a corn plant or seed exhibits a reduction of LW rating score of about 4.5 or more. In further aspects, a corn plant or seed exhibits a reduction of LW rating score of about 5 or more. In further aspects, a corn plant or seed exhibits a reduction of LW rating score of about 5.5 or more. In further aspects, a corn plant or seed exhibits a reduction of LW rating score of about 6 or more. In further aspects, a corn plant or seed exhibits a reduction of LW rating score of about 6.5 or more. In further aspects, a corn plant or seed exhibits a reduction of LW rating score of about 7 or more. In further aspects, a corn plant or seed exhibits a reduction of LW rating score of about or 7.5 or more.

In another aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of the LW rating score compared to a corn plant or seed without the three or more LW resistance QTLs under a similar growth condition (e.g., a high LW stress condition). In further aspects, a corn plant or seed exhibits a reduction of LW rating score of about 0.25 or more. In further aspects, a corn plant or seed exhibits a reduction of LW rating score of about 0.5 or more. In further aspects, a corn plant or seed exhibits a reduction of LW rating score of about 0.75 or more. In further aspects, a corn plant or seed exhibits a reduction of LW rating score of about 1 or more. In further aspects, a corn plant or seed exhibits a reduction of LW rating score of about 1.5 or more. In further aspects, a corn plant or seed exhibits a reduction of LW rating score of about 2 or more. In further aspects, a corn plant or seed exhibits a reduction of LW rating score of about 2.5 or more. In further aspects, a corn plant or seed exhibits a reduction of LW rating score of about 3 or more. In further aspects, a corn plant or seed exhibits a reduction of LW rating score of about 3.5 or more. In further aspects, a corn plant or seed exhibits a reduction of LW rating score of about 4 or more. In further aspects, a corn plant or seed exhibits a reduction of LW rating score of about 4.5 or more. In further aspects, a corn plant or seed exhibits a reduction of LW rating score of about 5 or more. In further aspects, a corn plant or seed exhibits a reduction of LW rating score of about 5.5 or more. In further aspects, a corn plant or seed exhibits a reduction of LW rating score of about 6 or more. In further aspects, a corn plant or seed exhibits a reduction of LW rating score of about 6.5 or more. In further aspects, a corn plant or seed exhibits a reduction of LW rating score of about 7 or more. In further aspects, a corn plant or seed exhibits a reduction of LW rating score of about or 7.5 or more.

In another aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of the LW rating score compared to a corn plant or seed without the four or more LW resistance QTLs under a similar growth condition (e.g., a high LW stress condition). In further aspects, a corn plant or seed exhibits a reduction of LW rating score of about 0.25 or more. In further aspects, a corn plant or seed exhibits a reduction of LW rating score of about 0.5 or more. In further aspects, a corn plant or seed exhibits a reduction of LW rating score of about 0.75 or more. In further aspects, a corn plant or seed exhibits a reduction of LW rating score of about 1 or more. In further aspects, a corn plant or seed exhibits a reduction of LW rating score of about 1.5 or more. In further aspects, a corn plant or seed exhibits a reduction of LW rating score of about 2 or more. In further aspects, a corn plant or seed exhibits a reduction of LW rating score of about 2.5 or more. In further aspects, a corn plant or seed exhibits a reduction of LW rating score of about 3 or more. In further aspects, a corn plant or seed exhibits a reduction of LW rating score of about 3.5 or more. In further aspects, a corn plant or seed exhibits a reduction of LW rating score of about 4 or more. In further aspects, a corn plant or seed exhibits a reduction of LW rating score of about 4.5 or more. In further aspects, a corn plant or seed exhibits a reduction of LW rating score of about 5 or more. In further aspects, a corn plant or seed exhibits a reduction of LW rating score of about 5.5 or more. In further aspects, a corn plant or seed exhibits a reduction of LW rating score of about 6 or more. In further aspects, a corn plant or seed exhibits a reduction of LW rating score of about 6.5 or more. In further aspects, a corn plant or seed exhibits a reduction of LW rating score of about 7 or more. In further aspects, a corn plant or seed exhibits a reduction of LW rating score of about or 7.5 or more.

In another aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of the LW rating score compared to a corn plant or seed without the five or more LW resistance QTLs under a similar growth condition (e.g., a high LW stress condition). In further aspects, a corn plant or seed exhibits a reduction of LW rating score of about 0.25 or more. In further aspects, a corn plant or seed exhibits a reduction of LW rating score of about 0.5 or more. In further aspects, a corn plant or seed exhibits a reduction of LW rating score of about 0.75 or more. In further aspects, a corn plant or seed exhibits a reduction of LW rating score of about 1 or more. In further aspects, a corn plant or seed exhibits a reduction of LW rating score of about 1.5 or more. In further aspects, a corn plant or seed exhibits a reduction of LW rating score of about 2 or more. In further aspects, a corn plant or seed exhibits a reduction of LW rating score of about 2.5 or more. In further aspects, a corn plant or seed exhibits a reduction of LW rating score of about 3 or more. In further aspects, a corn plant or seed exhibits a reduction of LW rating score of about 3.5 or more. In further aspects, a corn plant or seed exhibits a reduction of LW rating score of about 4 or more. In further aspects, a corn plant or seed exhibits a reduction of LW rating score of about 4.5 or more. In further aspects, a corn plant or seed exhibits a reduction of LW rating score of about 5 or more. In further aspects, a corn plant or seed exhibits a reduction of LW rating score of about 5.5 or more. In further aspects, a corn plant or seed exhibits a reduction of LW rating score of about 6 or more. In further aspects, a corn plant or seed exhibits a reduction of LW rating score of about 6.5 or more. In further aspects, a corn plant or seed exhibits a reduction of LW rating score of about 7 or more. In further aspects, a corn plant or seed exhibits a reduction of LW rating score of about or 7.5 or more.

In another aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of the LW rating score compared to a corn plant or seed without the six or more LW resistance QTLs under a similar growth condition (e.g., a high LW stress condition). In further aspects, a corn plant or seed exhibits a reduction of LW rating score of about 0.25 or more. In further aspects, a corn plant or seed exhibits a reduction of LW rating score of about 0.5 or more. In further aspects, a corn plant or seed exhibits a reduction of LW rating score of about 0.75 or more. In further aspects, a corn plant or seed exhibits a reduction of LW rating score of about 1 or more. In further aspects, a corn plant or seed exhibits a reduction of LW rating score of about 1.5 or more. In further aspects, a corn plant or seed exhibits a reduction of LW rating score of about 2 or more. In further aspects, a corn plant or seed exhibits a reduction of LW rating score of about 2.5 or more. In further aspects, a corn plant or seed exhibits a reduction of LW rating score of about 3 or more. In further aspects, a corn plant or seed exhibits a reduction of LW rating score of about 3.5 or more. In further aspects, a corn plant or seed exhibits a reduction of LW rating score of about 4 or more. In further aspects, a corn plant or seed exhibits a reduction of LW rating score of about 4.5 or more. In further aspects, a corn plant or seed exhibits a reduction of LW rating score of about 5 or more. In further aspects, a corn plant or seed exhibits a reduction of LW rating score of about 5.5 or more. In further aspects, a corn plant or seed exhibits a reduction of LW rating score of about 6 or more. In further aspects, a corn plant or seed exhibits a reduction of LW rating score of about 6.5 or more. In further aspects, a corn plant or seed exhibits a reduction of LW rating score of about 7 or more. In further aspects, a corn plant or seed exhibits a reduction of LW rating score of about or 7.5 or more.

In another aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the one or more LW resistance QTLs or LW resistance alleles under a similar growth condition (e.g., a high LW stress condition). In further aspects, a corn plant or seed exhibits a reduction of LW rating score of between 0.25 and 8. In further aspects, a corn plant or seed exhibits a reduction of LW rating score of between 0.25 and 7.5. In further aspects, a corn plant or seed exhibits a reduction of LW rating score of between 0.25 and 7. In further aspects, a corn plant or seed exhibits a reduction of LW rating score of between 0.25 and 6.5. In further aspects, a corn plant or seed exhibits a reduction of LW rating score of between 0.25 and 6. In further aspects, a corn plant or seed exhibits a reduction of LW rating score of between 0.25 and 5.5. In further aspects, a corn plant or seed exhibits a reduction of LW rating score of between 0.25 and 5. In further aspects, a corn plant or seed exhibits a reduction of LW rating score of between 0.25 and 4.5. In further aspects, a corn plant or seed exhibits a reduction of LW rating score of between 0.25 and 4. In further aspects, a corn plant or seed exhibits a reduction of LW rating score of between 0.25 and 3.5. In further aspects, a corn plant or seed exhibits a reduction of LW rating score of between 0.25 and 3. In further aspects, a corn plant or seed exhibits a reduction of LW rating score of between 0.25 and 2.5. In further aspects, a corn plant or seed exhibits a reduction of LW rating score of between 0.25 and 2. In further aspects, a corn plant or seed exhibits a reduction of LW rating score of between 0.25 and 1.5. In further aspects, a corn plant or seed exhibits a reduction of LW rating score of between 0.25 and 1. In further aspects, a corn plant or seed exhibits a reduction of LW rating score of between 1 and 8. In further aspects, a corn plant or seed exhibits a reduction of LW rating score of between 1 and 7. In further aspects, a corn plant or seed exhibits a reduction of LW rating score of between 1 and 6. In further aspects, a corn plant or seed exhibits a reduction of LW rating score of between 1 and 5. In further aspects, a corn plant or seed exhibits a reduction of LW rating score of between 1 and 4. In further aspects, a corn plant or seed exhibits a reduction of LW rating score of between 1 and 3. In further aspects, a corn plant or seed exhibits a reduction of LW rating score of between 1 and 2.

In another aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the two or more LW resistance QTLs or LW resistance alleles under a similar growth condition (e.g., a high LW stress condition). In further aspects, a corn plant or seed exhibits a reduction of LW rating score of between 0.25 and 8. In further aspects, a corn plant or seed exhibits a reduction of LW rating score of between 0.25 and 7.5. In further aspects, a corn plant or seed exhibits a reduction of LW rating score of between 0.25 and 7. In further aspects, a corn plant or seed exhibits a reduction of LW rating score of between 0.25 and 6.5. In further aspects, a corn plant or seed exhibits a reduction of LW rating score of between 0.25 and 6. In further aspects, a corn plant or seed exhibits a reduction of LW rating score of between 0.25 and 5.5. In further aspects, a corn plant or seed exhibits a reduction of LW rating score of between 0.25 and 5. In further aspects, a corn plant or seed exhibits a reduction of LW rating score of between 0.25 and 4.5. In further aspects, a corn plant or seed exhibits a reduction of LW rating score of between 0.25 and 4. In further aspects, a corn plant or seed exhibits a reduction of LW rating score of between 0.25 and 3.5. In further aspects, a corn plant or seed exhibits a reduction of LW rating score of between 0.25 and 3. In further aspects, a corn plant or seed exhibits a reduction of LW rating score of between 0.25 and 2.5. In further aspects, a corn plant or seed exhibits a reduction of LW rating score of between 0.25 and 2. In further aspects, a corn plant or seed exhibits a reduction of LW rating score of between 0.25 and 1.5. In further aspects, a corn plant or seed exhibits a reduction of LW rating score of between 0.25 and 1. In further aspects, a corn plant or seed exhibits a reduction of LW rating score of between 1 and 8. In further aspects, a corn plant or seed exhibits a reduction of LW rating score of between 1 and 7. In further aspects, a corn plant or seed exhibits a reduction of LW rating score of between 1 and 6. In further aspects, a corn plant or seed exhibits a reduction of LW rating score of between 1 and 5. In further aspects, a corn plant or seed exhibits a reduction of LW rating score of between 1 and 4. In further aspects, a corn plant or seed exhibits a reduction of LW rating score of between 1 and 3. In further aspects, a corn plant or seed exhibits a reduction of LW rating score of between 1 and 2.

In another aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the three or more LW resistance QTLs or LW resistance alleles under a similar growth condition (e.g., a high LW stress condition). In further aspects, a corn plant or seed exhibits a reduction of LW rating score of between 0.25 and 8. In further aspects, a corn plant or seed exhibits a reduction of LW rating score of between 0.25 and 7.5. In further aspects, a corn plant or seed exhibits a reduction of LW rating score of between 0.25 and 7. In further aspects, a corn plant or seed exhibits a reduction of LW rating score of between 0.25 and 6.5. In further aspects, a corn plant or seed exhibits a reduction of LW rating score of between 0.25 and 6. In further aspects, a corn plant or seed exhibits a reduction of LW rating score of between 0.25 and 5.5. In further aspects, a corn plant or seed exhibits a reduction of LW rating score of between 0.25 and 5. In further aspects, a corn plant or seed exhibits a reduction of LW rating score of between 0.25 and 4.5. In further aspects, a corn plant or seed exhibits a reduction of LW rating score of between 0.25 and 4. In further aspects, a corn plant or seed exhibits a reduction of LW rating score of between 0.25 and 3.5. In further aspects, a corn plant or seed exhibits a reduction of LW rating score of between 0.25 and 3. In further aspects, a corn plant or seed exhibits a reduction of LW rating score of between 0.25 and 2.5. In further aspects, a corn plant or seed exhibits a reduction of LW rating score of between 0.25 and 2. In further aspects, a corn plant or seed exhibits a reduction of LW rating score of between 0.25 and 1.5. In further aspects, a corn plant or seed exhibits a reduction of LW rating score of between 0.25 and 1. In further aspects, a corn plant or seed exhibits a reduction of LW rating score of between 1 and 8. In further aspects, a corn plant or seed exhibits a reduction of LW rating score of between 1 and 7. In further aspects, a corn plant or seed exhibits a reduction of LW rating score of between 1 and 6. In further aspects, a corn plant or seed exhibits a reduction of LW rating score of between 1 and 5. In further aspects, a corn plant or seed exhibits a reduction of LW rating score of between 1 and 4. In further aspects, a corn plant or seed exhibits a reduction of LW rating score of between 1 and 3. In further aspects, a corn plant or seed exhibits a reduction of LW rating score of between 1 and 2.

In another aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the four or more LW resistance QTLs or LW resistance alleles under a similar growth condition (e.g., a high LW stress condition). In further aspects, a corn plant or seed exhibits a reduction of LW rating score of between 0.25 and 8. In further aspects, a corn plant or seed exhibits a reduction of LW rating score of between 0.25 and 7.5. In further aspects, a corn plant or seed exhibits a reduction of LW rating score of between 0.25 and 7. In further aspects, a corn plant or seed exhibits a reduction of LW rating score of between 0.25 and 6.5. In further aspects, a corn plant or seed exhibits a reduction of LW rating score of between 0.25 and 6. In further aspects, a corn plant or seed exhibits a reduction of LW rating score of between 0.25 and 5.5. In further aspects, a corn plant or seed exhibits a reduction of LW rating score of between 0.25 and 5. In further aspects, a corn plant or seed exhibits a reduction of LW rating score of between 0.25 and 4.5. In further aspects, a corn plant or seed exhibits a reduction of LW rating score of between 0.25 and 4. In further aspects, a corn plant or seed exhibits a reduction of LW rating score of between 0.25 and 3.5. In further aspects, a corn plant or seed exhibits a reduction of LW rating score of between 0.25 and 3. In further aspects, a corn plant or seed exhibits a reduction of LW rating score of between 0.25 and 2.5. In further aspects, a corn plant or seed exhibits a reduction of LW rating score of between 0.25 and 2. In further aspects, a corn plant or seed exhibits a reduction of LW rating score of between 0.25 and 1.5. In further aspects, a corn plant or seed exhibits a reduction of LW rating score of between 0.25 and 1. In further aspects, a corn plant or seed exhibits a reduction of LW rating score of between 1 and 8. In further aspects, a corn plant or seed exhibits a reduction of LW rating score of between 1 and 7. In further aspects, a corn plant or seed exhibits a reduction of LW rating score of between 1 and 6. In further aspects, a corn plant or seed exhibits a reduction of LW rating score of between 1 and 5. In further aspects, a corn plant or seed exhibits a reduction of LW rating score of between 1 and 4. In further aspects, a corn plant or seed exhibits a reduction of LW rating score of between 1 and 3. In further aspects, a corn plant or seed exhibits a reduction of LW rating score of between 1 and 2.

In another aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the five or more LW resistance QTLs or LW resistance alleles under a similar growth condition (e.g., a high LW stress condition). In further aspects, a corn plant or seed exhibits a reduction of LW rating score of between 0.25 and 8. In further aspects, a corn plant or seed exhibits a reduction of LW rating score of between 0.25 and 7.5. In further aspects, a corn plant or seed exhibits a reduction of LW rating score of between 0.25 and 7. In further aspects, a corn plant or seed exhibits a reduction of LW rating score of between 0.25 and 6.5. In further aspects, a corn plant or seed exhibits a reduction of LW rating score of between 0.25 and 6. In further aspects, a corn plant or seed exhibits a reduction of LW rating score of between 0.25 and 5.5. In further aspects, a corn plant or seed exhibits a reduction of LW rating score of between 0.25 and 5. In further aspects, a corn plant or seed exhibits a reduction of LW rating score of between 0.25 and 4.5. In further aspects, a corn plant or seed exhibits a reduction of LW rating score of between 0.25 and 4. In further aspects, a corn plant or seed exhibits a reduction of LW rating score of between 0.25 and 3.5. In further aspects, a corn plant or seed exhibits a reduction of LW rating score of between 0.25 and 3. In further aspects, a corn plant or seed exhibits a reduction of LW rating score of between 0.25 and 2.5. In further aspects, a corn plant or seed exhibits a reduction of LW rating score of between 0.25 and 2. In further aspects, a corn plant or seed exhibits a reduction of LW rating score of between 0.25 and 1.5. In further aspects, a corn plant or seed exhibits a reduction of LW rating score of between 0.25 and 1. In further aspects, a corn plant or seed exhibits a reduction of LW rating score of between 1 and 8. In further aspects, a corn plant or seed exhibits a reduction of LW rating score of between 1 and 7. In further aspects, a corn plant or seed exhibits a reduction of LW rating score of between 1 and 6. In further aspects, a corn plant or seed exhibits a reduction of LW rating score of between 1 and 5. In further aspects, a corn plant or seed exhibits a reduction of LW rating score of between 1 and 4. In further aspects, a corn plant or seed exhibits a reduction of LW rating score of between 1 and 3. In further aspects, a corn plant or seed exhibits a reduction of LW rating score of between 1 and 2.

In another aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the six or more LW resistance QTLs or LW resistance alleles under a similar growth condition (e.g., a high LW stress condition). In further aspects, a corn plant or seed exhibits a reduction of LW rating score of between 0.25 and 8. In further aspects, a corn plant or seed exhibits a reduction of LW rating score of between 0.25 and 7.5. In further aspects, a corn plant or seed exhibits a reduction of LW rating score of between 0.25 and 7. In further aspects, a corn plant or seed exhibits a reduction of LW rating score of between 0.25 and 6.5. In further aspects, a corn plant or seed exhibits a reduction of LW rating score of between 0.25 and 6. In further aspects, a corn plant or seed exhibits a reduction of LW rating score of between 0.25 and 5.5. In further aspects, a corn plant or seed exhibits a reduction of LW rating score of between 0.25 and 5. In further aspects, a corn plant or seed exhibits a reduction of LW rating score of between 0.25 and 4.5. In further aspects, a corn plant or seed exhibits a reduction of LW rating score of between 0.25 and 4. In further aspects, a corn plant or seed exhibits a reduction of LW rating score of between 0.25 and 3.5. In further aspects, a corn plant or seed exhibits a reduction of LW rating score of between 0.25 and 3. In further aspects, a corn plant or seed exhibits a reduction of LW rating score of between 0.25 and 2.5. In further aspects, a corn plant or seed exhibits a reduction of LW rating score of between 0.25 and 2. In further aspects, a corn plant or seed exhibits a reduction of LW rating score of between 0.25 and 1.5. In further aspects, a corn plant or seed exhibits a reduction of LW rating score of between 0.25 and 1. In further aspects, a corn plant or seed exhibits a reduction of LW rating score of between 1 and 8. In further aspects, a corn plant or seed exhibits a reduction of LW rating score of between 1 and 7. In further aspects, a corn plant or seed exhibits a reduction of LW rating score of between 1 and 6. In further aspects, a corn plant or seed exhibits a reduction of LW rating score of between 1 and 5. In further aspects, a corn plant or seed exhibits a reduction of LW rating score of between 1 and 4. In further aspects, a corn plant or seed exhibits a reduction of LW rating score of between 1 and 3. In further aspects, a corn plant or seed exhibits a reduction of LW rating score of between 1 and 2.

In another aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the one or more LW resistance QTLs under a similar growth condition (e.g., a high LW stress condition). In further aspects, a corn plant or seed exhibits a reduction of LW rating score of between 5% and 90%. In further aspects, a corn plant or seed exhibits a reduction of LW rating score of 5% and 80%. In further aspects, a corn plant or seed exhibits a reduction of LW rating score of between 5% and 70%. In further aspects, a corn plant or seed exhibits a reduction of LW rating score of between 5% and 60%. In further aspects, a corn plant or seed exhibits a reduction of LW rating score of between 5% and 50%. In further aspects, a corn plant or seed exhibits a reduction of LW rating score of between 5% and 40%. In further aspects, a corn plant or seed exhibits a reduction of LW rating score of between 5% and 30%. In further aspects, a corn plant or seed exhibits a reduction of LW rating score of between 5% and 20%. In further aspects, a corn plant or seed exhibits a reduction of LW rating score of between 5% and 15%. In further aspects, a corn plant or seed exhibits a reduction of LW rating score of or between 5% and 10%.

In another aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the two or more LW resistance QTLs under a similar growth condition (e.g., a high LW stress condition). In further aspects, a corn plant or seed exhibits a reduction of LW rating score of between 5% and 90%. In further aspects, a corn plant or seed exhibits a reduction of LW rating score of 5% and 80%. In further aspects, a corn plant or seed exhibits a reduction of LW rating score of between 5% and 70%. In further aspects, a corn plant or seed exhibits a reduction of LW rating score of between 5% and 60%. In further aspects, a corn plant or seed exhibits a reduction of LW rating score of between 5% and 50%. In further aspects, a corn plant or seed exhibits a reduction of LW rating score of between 5% and 40%. In further aspects, a corn plant or seed exhibits a reduction of LW rating score of between 5% and 30%. In further aspects, a corn plant or seed exhibits a reduction of LW rating score of between 5% and 20%. In further aspects, a corn plant or seed exhibits a reduction of LW rating score of between 5% and 15%. In further aspects, a corn plant or seed exhibits a reduction of LW rating score of or between 5% and 10%.

In another aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the three or more LW resistance QTLs under a similar growth condition (e.g., a high LW stress condition). In further aspects, a corn plant or seed exhibits a reduction of LW rating score of between 5% and 90%. In further aspects, a corn plant or seed exhibits a reduction of LW rating score of 5% and 80%. In further aspects, a corn plant or seed exhibits a reduction of LW rating score of between 5% and 70%. In further aspects, a corn plant or seed exhibits a reduction of LW rating score of between 5% and 60%. In further aspects, a corn plant or seed exhibits a reduction of LW rating score of between 5% and 50%. In further aspects, a corn plant or seed exhibits a reduction of LW rating score of between 5% and 40%. In further aspects, a corn plant or seed exhibits a reduction of LW rating score of between 5% and 30%. In further aspects, a corn plant or seed exhibits a reduction of LW rating score of between 5% and 20%. In further aspects, a corn plant or seed exhibits a reduction of LW rating score of between 5% and 15%. In further aspects, a corn plant or seed exhibits a reduction of LW rating score of or between 5% and 10%.

In another aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the four or more LW resistance QTLs under a similar growth condition (e.g., a high LW stress condition). In further aspects, a corn plant or seed exhibits a reduction of LW rating score of between 5% and 90%. In further aspects, a corn plant or seed exhibits a reduction of LW rating score of 5% and 80%. In further aspects, a corn plant or seed exhibits a reduction of LW rating score of between 5% and 70%. In further aspects, a corn plant or seed exhibits a reduction of LW rating score of between 5% and 60%. In further aspects, a corn plant or seed exhibits a reduction of LW rating score of between 5% and 50%. In further aspects, a corn plant or seed exhibits a reduction of LW rating score of between 5% and 40%. In further aspects, a corn plant or seed exhibits a reduction of LW rating score of between 5% and 30%. In further aspects, a corn plant or seed exhibits a reduction of LW rating score of between 5% and 20%. In further aspects, a corn plant or seed exhibits a reduction of LW rating score of between 5% and 15%. In further aspects, a corn plant or seed exhibits a reduction of LW rating score of or between 5% and 10%.

In another aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the five or more LW resistance QTLs under a similar growth condition (e.g., a high LW stress condition). In further aspects, a corn plant or seed exhibits a reduction of LW rating score of between 5% and 90%. In further aspects, a corn plant or seed exhibits a reduction of LW rating score of 5% and 80%. In further aspects, a corn plant or seed exhibits a reduction of LW rating score of between 5% and 70%. In further aspects, a corn plant or seed exhibits a reduction of LW rating score of between 5% and 60%. In further aspects, a corn plant or seed exhibits a reduction of LW rating score of between 5% and 50%. In further aspects, a corn plant or seed exhibits a reduction of LW rating score of between 5% and 40%. In further aspects, a corn plant or seed exhibits a reduction of LW rating score of between 5% and 30%. In further aspects, a corn plant or seed exhibits a reduction of LW rating score of between 5% and 20%. In further aspects, a corn plant or seed exhibits a reduction of LW rating score of between 5% and 15%. In further aspects, a corn plant or seed exhibits a reduction of LW rating score of or between 5% and 10%.

In another aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a reduction of LW rating score compared to a corn plant or seed without the six or more LW resistance QTLs under a similar growth condition (e.g., a high LW stress condition). In further aspects, a corn plant or seed exhibits a reduction of LW rating score of between 5% and 90%. In further aspects, a corn plant or seed exhibits a reduction of LW rating score of 5% and 80%. In further aspects, a corn plant or seed exhibits a reduction of LW rating score of between 5% and 70%. In further aspects, a corn plant or seed exhibits a reduction of LW rating score of between 5% and 60%. In further aspects, a corn plant or seed exhibits a reduction of LW rating score of between 5% and 50%. In further aspects, a corn plant or seed exhibits a reduction of LW rating score of between 5% and 40%. In further aspects, a corn plant or seed exhibits a reduction of LW rating score of between 5% and 30%. In further aspects, a corn plant or seed exhibits a reduction of LW rating score of between 5% and 20%. In further aspects, a corn plant or seed exhibits a reduction of LW rating score of between 5% and 15%. In further aspects, a corn plant or seed exhibits a reduction of LW rating score of or between 5% and 10%.

In an aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the one or more LW resistance QTLs under a similar growth condition (e.g., a high LW stress condition). In a further aspect, a corn plant or seed disclosed herein exhibits a seed yield increase of about 1% or more. In a further aspect, a corn plant or seed disclosed herein exhibits a seed yield increase of about 2% or more. In a further aspect, a corn plant or seed disclosed herein exhibits a seed yield increase of about 3% or more. In a further aspect, a corn plant or seed disclosed herein exhibits a seed yield increase of about 4% or more. In a further aspect, a corn plant or seed disclosed herein exhibits a seed yield increase of about 5% or more. In a further aspect, a corn plant or seed disclosed herein exhibits a seed yield increase of about 10% or more. In a further aspect, a corn plant or seed disclosed herein exhibits a seed yield increase of about 15% or more. In a further aspect, a corn plant or seed disclosed herein exhibits a seed yield increase of about 20% or more. In a further aspect, a corn plant or seed disclosed herein exhibits a seed yield increase of about 25% or more. In a further aspect, a corn plant or seed disclosed herein exhibits a seed yield increase of about 30% or more. In a further aspect, a corn plant or seed disclosed herein exhibits a seed yield increase of about 40% or more. In a further aspect, a corn plant or seed disclosed herein exhibits a seed yield increase of about 50% or more. In a further aspect, a corn plant or seed disclosed herein exhibits a seed yield increase of about 60% or more. In a further aspect, a corn plant or seed disclosed herein exhibits a seed yield increase of about 70% or more. In a further aspect, a corn plant or seed disclosed herein exhibits a seed yield increase of about 80% or more. In a further aspect, a corn plant or seed disclosed herein exhibits a seed yield increase of about 90% or more. In a further aspect, a corn plant or seed disclosed herein exhibits a seed yield increase of about 100% or more.

In an aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the two or more LW resistance QTLs under a similar growth condition (e.g., a high LW stress condition). In a further aspect, a corn plant or seed disclosed herein exhibits a seed yield increase of about 1% or more. In a further aspect, a corn plant or seed disclosed herein exhibits a seed yield increase of about 2% or more. In a further aspect, a corn plant or seed disclosed herein exhibits a seed yield increase of about 3% or more. In a further aspect, a corn plant or seed disclosed herein exhibits a seed yield increase of about 4% or more. In a further aspect, a corn plant or seed disclosed herein exhibits a seed yield increase of about 5% or more. In a further aspect, a corn plant or seed disclosed herein exhibits a seed yield increase of about 10% or more. In a further aspect, a corn plant or seed disclosed herein exhibits a seed yield increase of about 15% or more. In a further aspect, a corn plant or seed disclosed herein exhibits a seed yield increase of about 20% or more. In a further aspect, a corn plant or seed disclosed herein exhibits a seed yield increase of about 25% or more. In a further aspect, a corn plant or seed disclosed herein exhibits a seed yield increase of about 30% or more. In a further aspect, a corn plant or seed disclosed herein exhibits a seed yield increase of about 40% or more. In a further aspect, a corn plant or seed disclosed herein exhibits a seed yield increase of about 50% or more. In a further aspect, a corn plant or seed disclosed herein exhibits a seed yield increase of about 60% or more. In a further aspect, a corn plant or seed disclosed herein exhibits a seed yield increase of about 70% or more. In a further aspect, a corn plant or seed disclosed herein exhibits a seed yield increase of about 80% or more. In a further aspect, a corn plant or seed disclosed herein exhibits a seed yield increase of about 90% or more. In a further aspect, a corn plant or seed disclosed herein exhibits a seed yield increase of about 100% or more.

In an aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the three or more LW resistance QTLs under a similar growth condition (e.g., a high LW stress condition). In a further aspect, a corn plant or seed disclosed herein exhibits a seed yield increase of about 1% or more. In a further aspect, a corn plant or seed disclosed herein exhibits a seed yield increase of about 2% or more. In a further aspect, a corn plant or seed disclosed herein exhibits a seed yield increase of about 3% or more. In a further aspect, a corn plant or seed disclosed herein exhibits a seed yield increase of about 4% or more. In a further aspect, a corn plant or seed disclosed herein exhibits a seed yield increase of about 5% or more. In a further aspect, a corn plant or seed disclosed herein exhibits a seed yield increase of about 10% or more. In a further aspect, a corn plant or seed disclosed herein exhibits a seed yield increase of about 15% or more. In a further aspect, a corn plant or seed disclosed herein exhibits a seed yield increase of about 20% or more. In a further aspect, a corn plant or seed disclosed herein exhibits a seed yield increase of about 25% or more. In a further aspect, a corn plant or seed disclosed herein exhibits a seed yield increase of about 30% or more. In a further aspect, a corn plant or seed disclosed herein exhibits a seed yield increase of about 40% or more. In a further aspect, a corn plant or seed disclosed herein exhibits a seed yield increase of about 50% or more. In a further aspect, a corn plant or seed disclosed herein exhibits a seed yield increase of about 60% or more. In a further aspect, a corn plant or seed disclosed herein exhibits a seed yield increase of about 70% or more. In a further aspect, a corn plant or seed disclosed herein exhibits a seed yield increase of about 80% or more. In a further aspect, a corn plant or seed disclosed herein exhibits a seed yield increase of about 90% or more. In a further aspect, a corn plant or seed disclosed herein exhibits a seed yield increase of about 100% or more.

In an aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the four or more LW resistance QTLs under a similar growth condition (e.g., a high LW stress condition). In a further aspect, a corn plant or seed disclosed herein exhibits a seed yield increase of about 1% or more. In a further aspect, a corn plant or seed disclosed herein exhibits a seed yield increase of about 2% or more. In a further aspect, a corn plant or seed disclosed herein exhibits a seed yield increase of about 3% or more. In a further aspect, a corn plant or seed disclosed herein exhibits a seed yield increase of about 4% or more. In a further aspect, a corn plant or seed disclosed herein exhibits a seed yield increase of about 5% or more. In a further aspect, a corn plant or seed disclosed herein exhibits a seed yield increase of about 10% or more. In a further aspect, a corn plant or seed disclosed herein exhibits a seed yield increase of about 15% or more. In a further aspect, a corn plant or seed disclosed herein exhibits a seed yield increase of about 20% or more. In a further aspect, a corn plant or seed disclosed herein exhibits a seed yield increase of about 25% or more. In a further aspect, a corn plant or seed disclosed herein exhibits a seed yield increase of about 30% or more. In a further aspect, a corn plant or seed disclosed herein exhibits a seed yield increase of about 40% or more. In a further aspect, a corn plant or seed disclosed herein exhibits a seed yield increase of about 50% or more. In a further aspect, a corn plant or seed disclosed herein exhibits a seed yield increase of about 60% or more. In a further aspect, a corn plant or seed disclosed herein exhibits a seed yield increase of about 70% or more. In a further aspect, a corn plant or seed disclosed herein exhibits a seed yield increase of about 80% or more. In a further aspect, a corn plant or seed disclosed herein exhibits a seed yield increase of about 90% or more. In a further aspect, a corn plant or seed disclosed herein exhibits a seed yield increase of about 100% or more.

In an aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the five or more LW resistance QTLs under a similar growth condition (e.g., a high LW stress condition). In a further aspect, a corn plant or seed disclosed herein exhibits a seed yield increase of about 1% or more. In a further aspect, a corn plant or seed disclosed herein exhibits a seed yield increase of about 2% or more. In a further aspect, a corn plant or seed disclosed herein exhibits a seed yield increase of about 3% or more. In a further aspect, a corn plant or seed disclosed herein exhibits a seed yield increase of about 4% or more. In a further aspect, a corn plant or seed disclosed herein exhibits a seed yield increase of about 5% or more. In a further aspect, a corn plant or seed disclosed herein exhibits a seed yield increase of about 10% or more. In a further aspect, a corn plant or seed disclosed herein exhibits a seed yield increase of about 15% or more. In a further aspect, a corn plant or seed disclosed herein exhibits a seed yield increase of about 20% or more. In a further aspect, a corn plant or seed disclosed herein exhibits a seed yield increase of about 25% or more. In a further aspect, a corn plant or seed disclosed herein exhibits a seed yield increase of about 30% or more. In a further aspect, a corn plant or seed disclosed herein exhibits a seed yield increase of about 40% or more. In a further aspect, a corn plant or seed disclosed herein exhibits a seed yield increase of about 50% or more. In a further aspect, a corn plant or seed disclosed herein exhibits a seed yield increase of about 60% or more. In a further aspect, a corn plant or seed disclosed herein exhibits a seed yield increase of about 70% or more. In a further aspect, a corn plant or seed disclosed herein exhibits a seed yield increase of about 80% or more. In a further aspect, a corn plant or seed disclosed herein exhibits a seed yield increase of about 90% or more. In a further aspect, a corn plant or seed disclosed herein exhibits a seed yield increase of about 100% or more.

In an aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the six or more LW resistance QTLs under a similar growth condition (e.g., a high LW stress condition). In a further aspect, a corn plant or seed disclosed herein exhibits a seed yield increase of about 1% or more. In a further aspect, a corn plant or seed disclosed herein exhibits a seed yield increase of about 2% or more. In a further aspect, a corn plant or seed disclosed herein exhibits a seed yield increase of about 3% or more. In a further aspect, a corn plant or seed disclosed herein exhibits a seed yield increase of about 4% or more. In a further aspect, a corn plant or seed disclosed herein exhibits a seed yield increase of about 5% or more. In a further aspect, a corn plant or seed disclosed herein exhibits a seed yield increase of about 10% or more. In a further aspect, a corn plant or seed disclosed herein exhibits a seed yield increase of about 15% or more. In a further aspect, a corn plant or seed disclosed herein exhibits a seed yield increase of about 20% or more. In a further aspect, a corn plant or seed disclosed herein exhibits a seed yield increase of about 25% or more. In a further aspect, a corn plant or seed disclosed herein exhibits a seed yield increase of about 30% or more. In a further aspect, a corn plant or seed disclosed herein exhibits a seed yield increase of about 40% or more. In a further aspect, a corn plant or seed disclosed herein exhibits a seed yield increase of about 50% or more. In a further aspect, a corn plant or seed disclosed herein exhibits a seed yield increase of about 60% or more. In a further aspect, a corn plant or seed disclosed herein exhibits a seed yield increase of about 70% or more. In a further aspect, a corn plant or seed disclosed herein exhibits a seed yield increase of about 80% or more. In a further aspect, a corn plant or seed disclosed herein exhibits a seed yield increase of about 90% or more. In a further aspect, a corn plant or seed disclosed herein exhibits a seed yield increase of about 100% or more.

In an aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the one or more LW resistance QTLs under a similar growth condition (e.g., a high LW stress condition). In a further aspect, a corn plant or seed disclosed herein exhibits a seed yield increase of between 1% and 100%. In a further aspect, a corn plant or seed disclosed herein exhibits a seed yield increase of between 1% and 90%. In a further aspect, a corn plant or seed disclosed herein exhibits a seed yield increase of between 1% and 80%. In a further aspect, a corn plant or seed disclosed herein exhibits a seed yield increase of between 1% and 70%. In a further aspect, a corn plant or seed disclosed herein exhibits a seed yield increase of between 1% and 60%. In a further aspect, a corn plant or seed disclosed herein exhibits a seed yield increase of between 1% and 50%. In a further aspect, a corn plant or seed disclosed herein exhibits a seed yield increase of between 1% and 40%. In a further aspect, a corn plant or seed disclosed herein exhibits a seed yield increase of between 1% and 30%. In a further aspect, a corn plant or seed disclosed herein exhibits a seed yield increase of between 1% and 25%. In a further aspect, a corn plant or seed disclosed herein exhibits a seed yield increase of between 1% and 20%. In a further aspect, a corn plant or seed disclosed herein exhibits a seed yield increase of between 1% and 15%. In a further aspect, a corn plant or seed disclosed herein exhibits a seed yield increase of between 1% and 10%. In a further aspect, a corn plant or seed disclosed herein exhibits a seed yield increase of between 1% and 5%. In a further aspect, a corn plant or seed disclosed herein exhibits a seed yield increase of between 1% and 4%. In a further aspect, a corn plant or seed disclosed herein exhibits a seed yield increase of between 1% and 3%. In a further aspect, a corn plant or seed disclosed herein exhibits a seed yield increase of between 1% and 2%. In a further aspect, a corn plant or seed disclosed herein exhibits a seed yield increase of between 2% and 90%. In a further aspect, a corn plant or seed disclosed herein exhibits a seed yield increase of between 3% and 80%. In a further aspect, a corn plant or seed disclosed herein exhibits a seed yield increase of between 4% and 70%. In a further aspect, a corn plant or seed disclosed herein exhibits a seed yield increase of between 5% and 60%. In a further aspect, a corn plant or seed disclosed herein exhibits a seed yield increase of between 10% and 50%. In a further aspect, a corn plant or seed disclosed herein exhibits a seed yield increase of between 15% and 40%. In a further aspect, a corn plant or seed disclosed herein exhibits a seed yield increase of between 20% and 30%. In a further aspect, a corn plant or seed disclosed herein exhibits a seed yield increase of between 5% and 25%.

In an aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the two or more LW resistance QTLs under a similar growth condition (e.g., a high LW stress condition). In a further aspect, a corn plant or seed disclosed herein exhibits a seed yield increase of between 1% and 100%. In a further aspect, a corn plant or seed disclosed herein exhibits a seed yield increase of between 1% and 90%. In a further aspect, a corn plant or seed disclosed herein exhibits a seed yield increase of between 1% and 80%. In a further aspect, a corn plant or seed disclosed herein exhibits a seed yield increase of between 1% and 70%. In a further aspect, a corn plant or seed disclosed herein exhibits a seed yield increase of between 1% and 60%. In a further aspect, a corn plant or seed disclosed herein exhibits a seed yield increase of between 1% and 50%. In a further aspect, a corn plant or seed disclosed herein exhibits a seed yield increase of between 1% and 40%. In a further aspect, a corn plant or seed disclosed herein exhibits a seed yield increase of between 1% and 30%. In a further aspect, a corn plant or seed disclosed herein exhibits a seed yield increase of between 1% and 25%. In a further aspect, a corn plant or seed disclosed herein exhibits a seed yield increase of between 1% and 20%. In a further aspect, a corn plant or seed disclosed herein exhibits a seed yield increase of between 1% and 15%. In a further aspect, a corn plant or seed disclosed herein exhibits a seed yield increase of between 1% and 10%. In a further aspect, a corn plant or seed disclosed herein exhibits a seed yield increase of between 1% and 5%. In a further aspect, a corn plant or seed disclosed herein exhibits a seed yield increase of between 1% and 4%. In a further aspect, a corn plant or seed disclosed herein exhibits a seed yield increase of between 1% and 3%. In a further aspect, a corn plant or seed disclosed herein exhibits a seed yield increase of between 1% and 2%. In a further aspect, a corn plant or seed disclosed herein exhibits a seed yield increase of between 2% and 90%. In a further aspect, a corn plant or seed disclosed herein exhibits a seed yield increase of between 3% and 80%. In a further aspect, a corn plant or seed disclosed herein exhibits a seed yield increase of between 4% and 70%. In a further aspect, a corn plant or seed disclosed herein exhibits a seed yield increase of between 5% and 60%. In a further aspect, a corn plant or seed disclosed herein exhibits a seed yield increase of between 10% and 50%. In a further aspect, a corn plant or seed disclosed herein exhibits a seed yield increase of between 15% and 40%. In a further aspect, a corn plant or seed disclosed herein exhibits a seed yield increase of between 20% and 30%. In a further aspect, a corn plant or seed disclosed herein exhibits a seed yield increase of between 5% and 25%.

In an aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the three or more LW resistance QTLs under a similar growth condition (e.g., a high LW stress condition). In a further aspect, a corn plant or seed disclosed herein exhibits a seed yield increase of between 1% and 100%. In a further aspect, a corn plant or seed disclosed herein exhibits a seed yield increase of between 1% and 90%. In a further aspect, a corn plant or seed disclosed herein exhibits a seed yield increase of between 1% and 80%. In a further aspect, a corn plant or seed disclosed herein exhibits a seed yield increase of between 1% and 70%. In a further aspect, a corn plant or seed disclosed herein exhibits a seed yield increase of between 1% and 60%. In a further aspect, a corn plant or seed disclosed herein exhibits a seed yield increase of between 1% and 50%. In a further aspect, a corn plant or seed disclosed herein exhibits a seed yield increase of between 1% and 40%. In a further aspect, a corn plant or seed disclosed herein exhibits a seed yield increase of between 1% and 30%. In a further aspect, a corn plant or seed disclosed herein exhibits a seed yield increase of between 1% and 25%. In a further aspect, a corn plant or seed disclosed herein exhibits a seed yield increase of between 1% and 20%. In a further aspect, a corn plant or seed disclosed herein exhibits a seed yield increase of between 1% and 15%. In a further aspect, a corn plant or seed disclosed herein exhibits a seed yield increase of between 1% and 10%. In a further aspect, a corn plant or seed disclosed herein exhibits a seed yield increase of between 1% and 5%. In a further aspect, a corn plant or seed disclosed herein exhibits a seed yield increase of between 1% and 4%. In a further aspect, a corn plant or seed disclosed herein exhibits a seed yield increase of between 1% and 3%. In a further aspect, a corn plant or seed disclosed herein exhibits a seed yield increase of between 1% and 2%. In a further aspect, a corn plant or seed disclosed herein exhibits a seed yield increase of between 2% and 90%. In a further aspect, a corn plant or seed disclosed herein exhibits a seed yield increase of between 3% and 80%. In a further aspect, a corn plant or seed disclosed herein exhibits a seed yield increase of between 4% and 70%. In a further aspect, a corn plant or seed disclosed herein exhibits a seed yield increase of between 5% and 60%. In a further aspect, a corn plant or seed disclosed herein exhibits a seed yield increase of between 10% and 50%. In a further aspect, a corn plant or seed disclosed herein exhibits a seed yield increase of between 15% and 40%. In a further aspect, a corn plant or seed disclosed herein exhibits a seed yield increase of between 20% and 30%. In a further aspect, a corn plant or seed disclosed herein exhibits a seed yield increase of between 5% and 25%.

In an aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the four or more LW resistance QTLs under a similar growth condition (e.g., a high LW stress condition). In a further aspect, a corn plant or seed disclosed herein exhibits a seed yield increase of between 1% and 100%. In a further aspect, a corn plant or seed disclosed herein exhibits a seed yield increase of between 1% and 90%. In a further aspect, a corn plant or seed disclosed herein exhibits a seed yield increase of between 1% and 80%. In a further aspect, a corn plant or seed disclosed herein exhibits a seed yield increase of between 1% and 70%. In a further aspect, a corn plant or seed disclosed herein exhibits a seed yield increase of between 1% and 60%. In a further aspect, a corn plant or seed disclosed herein exhibits a seed yield increase of between 1% and 50%. In a further aspect, a corn plant or seed disclosed herein exhibits a seed yield increase of between 1% and 40%. In a further aspect, a corn plant or seed disclosed herein exhibits a seed yield increase of between 1% and 30%. In a further aspect, a corn plant or seed disclosed herein exhibits a seed yield increase of between 1% and 25%. In a further aspect, a corn plant or seed disclosed herein exhibits a seed yield increase of between 1% and 20%. In a further aspect, a corn plant or seed disclosed herein exhibits a seed yield increase of between 1% and 15%. In a further aspect, a corn plant or seed disclosed herein exhibits a seed yield increase of between 1% and 10%. In a further aspect, a corn plant or seed disclosed herein exhibits a seed yield increase of between 1% and 5%. In a further aspect, a corn plant or seed disclosed herein exhibits a seed yield increase of between 1% and 4%. In a further aspect, a corn plant or seed disclosed herein exhibits a seed yield increase of between 1% and 3%. In a further aspect, a corn plant or seed disclosed herein exhibits a seed yield increase of between 1% and 2%. In a further aspect, a corn plant or seed disclosed herein exhibits a seed yield increase of between 2% and 90%. In a further aspect, a corn plant or seed disclosed herein exhibits a seed yield increase of between 3% and 80%. In a further aspect, a corn plant or seed disclosed herein exhibits a seed yield increase of between 4% and 70%. In a further aspect, a corn plant or seed disclosed herein exhibits a seed yield increase of between 5% and 60%. In a further aspect, a corn plant or seed disclosed herein exhibits a seed yield increase of between 10% and 50%. In a further aspect, a corn plant or seed disclosed herein exhibits a seed yield increase of between 15% and 40%. In a further aspect, a corn plant or seed disclosed herein exhibits a seed yield increase of between 20% and 30%. In a further aspect, a corn plant or seed disclosed herein exhibits a seed yield increase of between 5% and 25%.

In an aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the five or more LW resistance QTLs under a similar growth condition (e.g., a high LW stress condition). In a further aspect, a corn plant or seed disclosed herein exhibits a seed yield increase of between 1% and 100%. In a further aspect, a corn plant or seed disclosed herein exhibits a seed yield increase of between 1% and 90%. In a further aspect, a corn plant or seed disclosed herein exhibits a seed yield increase of between 1% and 80%. In a further aspect, a corn plant or seed disclosed herein exhibits a seed yield increase of between 1% and 70%. In a further aspect, a corn plant or seed disclosed herein exhibits a seed yield increase of between 1% and 60%. In a further aspect, a corn plant or seed disclosed herein exhibits a seed yield increase of between 1% and 50%. In a further aspect, a corn plant or seed disclosed herein exhibits a seed yield increase of between 1% and 40%. In a further aspect, a corn plant or seed disclosed herein exhibits a seed yield increase of between 1% and 30%. In a further aspect, a corn plant or seed disclosed herein exhibits a seed yield increase of between 1% and 25%. In a further aspect, a corn plant or seed disclosed herein exhibits a seed yield increase of between 1% and 20%. In a further aspect, a corn plant or seed disclosed herein exhibits a seed yield increase of between 1% and 15%. In a further aspect, a corn plant or seed disclosed herein exhibits a seed yield increase of between 1% and 10%. In a further aspect, a corn plant or seed disclosed herein exhibits a seed yield increase of between 1% and 5%. In a further aspect, a corn plant or seed disclosed herein exhibits a seed yield increase of between 1% and 4%. In a further aspect, a corn plant or seed disclosed herein exhibits a seed yield increase of between 1% and 3%. In a further aspect, a corn plant or seed disclosed herein exhibits a seed yield increase of between 1% and 2%. In a further aspect, a corn plant or seed disclosed herein exhibits a seed yield increase of between 2% and 90%. In a further aspect, a corn plant or seed disclosed herein exhibits a seed yield increase of between 3% and 80%. In a further aspect, a corn plant or seed disclosed herein exhibits a seed yield increase of between 4% and 70%. In a further aspect, a corn plant or seed disclosed herein exhibits a seed yield increase of between 5% and 60%. In a further aspect, a corn plant or seed disclosed herein exhibits a seed yield increase of between 10% and 50%. In a further aspect, a corn plant or seed disclosed herein exhibits a seed yield increase of between 15% and 40%. In a further aspect, a corn plant or seed disclosed herein exhibits a seed yield increase of between 20% and 30%. In a further aspect, a corn plant or seed disclosed herein exhibits a seed yield increase of between 5% and 25%.

In an aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase as compared to the seed yield of a corn plant or seed without the six or more LW resistance QTLs under a similar growth condition (e.g., a high LW stress condition). In a further aspect, a corn plant or seed disclosed herein exhibits a seed yield increase of between 1% and 100%. In a further aspect, a corn plant or seed disclosed herein exhibits a seed yield increase of between 1% and 90%. In a further aspect, a corn plant or seed disclosed herein exhibits a seed yield increase of between 1% and 80%. In a further aspect, a corn plant or seed disclosed herein exhibits a seed yield increase of between 1% and 70%. In a further aspect, a corn plant or seed disclosed herein exhibits a seed yield increase of between 1% and 60%. In a further aspect, a corn plant or seed disclosed herein exhibits a seed yield increase of between 1% and 50%. In a further aspect, a corn plant or seed disclosed herein exhibits a seed yield increase of between 1% and 40%. In a further aspect, a corn plant or seed disclosed herein exhibits a seed yield increase of between 1% and 30%. In a further aspect, a corn plant or seed disclosed herein exhibits a seed yield increase of between 1% and 25%. In a further aspect, a corn plant or seed disclosed herein exhibits a seed yield increase of between 1% and 20%. In a further aspect, a corn plant or seed disclosed herein exhibits a seed yield increase of between 1% and 15%. In a further aspect, a corn plant or seed disclosed herein exhibits a seed yield increase of between 1% and 10%. In a further aspect, a corn plant or seed disclosed herein exhibits a seed yield increase of between 1% and 5%. In a further aspect, a corn plant or seed disclosed herein exhibits a seed yield increase of between 1% and 4%. In a further aspect, a corn plant or seed disclosed herein exhibits a seed yield increase of between 1% and 3%. In a further aspect, a corn plant or seed disclosed herein exhibits a seed yield increase of between 1% and 2%. In a further aspect, a corn plant or seed disclosed herein exhibits a seed yield increase of between 2% and 90%. In a further aspect, a corn plant or seed disclosed herein exhibits a seed yield increase of between 3% and 80%. In a further aspect, a corn plant or seed disclosed herein exhibits a seed yield increase of between 4% and 70%. In a further aspect, a corn plant or seed disclosed herein exhibits a seed yield increase of between 5% and 60%. In a further aspect, a corn plant or seed disclosed herein exhibits a seed yield increase of between 10% and 50%. In a further aspect, a corn plant or seed disclosed herein exhibits a seed yield increase of between 15% and 40%. In a further aspect, a corn plant or seed disclosed herein exhibits a seed yield increase of between 20% and 30%. In a further aspect, a corn plant or seed disclosed herein exhibits a seed yield increase of between 5% and 25%.

In an aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the one or more LW resistance QTLs under a similar growth condition (e.g., a high LW stress condition). In a further aspect, a corn plant or seed disclosed herein exhibits a seed yield increase of about 0.1 quintal/hectare or more (a quintal equals 100 kilograms). In a further aspect, a corn plant or seed disclosed herein exhibits a seed yield increase of about 0.25 quintal/hectare or more. In a further aspect, a corn plant or seed disclosed herein exhibits a seed yield increase of about 0.5 quintal/hectare or more. In a further aspect, a corn plant or seed disclosed herein exhibits a seed yield increase of about 0.75 quintal/hectare or more. In a further aspect, a corn plant or seed disclosed herein exhibits a seed yield increase of about 1 quintal/hectare or more. In a further aspect, a corn plant or seed disclosed herein exhibits a seed yield increase of about 1.5 quintal/hectare or more. In a further aspect, a corn plant or seed disclosed herein exhibits a seed yield increase of about 2 quintal/hectare or more. In a further aspect, a corn plant or seed disclosed herein exhibits a seed yield increase of about 2.5 quintal/hectare or more. In a further aspect, a corn plant or seed disclosed herein exhibits a seed yield increase of about 3 quintal/hectare or more. In a further aspect, a corn plant or seed disclosed herein exhibits a seed yield increase of about 3.5 quintal/hectare or more. In a further aspect, a corn plant or seed disclosed herein exhibits a seed yield increase of about 4 quintal/hectare or more. In a further aspect, a corn plant or seed disclosed herein exhibits a seed yield increase of about 4.5 quintal/hectare or more. In a further aspect, a corn plant or seed disclosed herein exhibits a seed yield increase of about 5 quintal/hectare or more. In a further aspect, a corn plant or seed disclosed herein exhibits a seed yield increase of about 6 quintal/hectare or more. In a further aspect, a corn plant or seed disclosed herein exhibits a seed yield increase of about 7 quintal/hectare or more. In a further aspect, a corn plant or seed disclosed herein exhibits a seed yield increase of about 8 quintal/hectare or more. In a further aspect, a corn plant or seed disclosed herein exhibits a seed yield increase of about 9 quintal/hectare or more. In a further aspect, a corn plant or seed disclosed herein exhibits a seed yield increase of about 10 quintal/hectare or more.

In an aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the two or more LW resistance QTLs under a similar growth condition (e.g., a high LW stress condition). In a further aspect, a corn plant or seed disclosed herein exhibits a seed yield increase of about 0.1 quintal/hectare or more. In a further aspect, a corn plant or seed disclosed herein exhibits a seed yield increase of about 0.25 quintal/hectare or more. In a further aspect, a corn plant or seed disclosed herein exhibits a seed yield increase of about 0.5 quintal/hectare or more. In a further aspect, a corn plant or seed disclosed herein exhibits a seed yield increase of about 0.75 quintal/hectare or more. In a further aspect, a corn plant or seed disclosed herein exhibits a seed yield increase of about 1 quintal/hectare or more. In a further aspect, a corn plant or seed disclosed herein exhibits a seed yield increase of about 1.5 quintal/hectare or more. In a further aspect, a corn plant or seed disclosed herein exhibits a seed yield increase of about 2 quintal/hectare or more. In a further aspect, a corn plant or seed disclosed herein exhibits a seed yield increase of about 2.5 quintal/hectare or more. In a further aspect, a corn plant or seed disclosed herein exhibits a seed yield increase of about 3 quintal/hectare or more. In a further aspect, a corn plant or seed disclosed herein exhibits a seed yield increase of about 3.5 quintal/hectare or more. In a further aspect, a corn plant or seed disclosed herein exhibits a seed yield increase of about 4 quintal/hectare or more. In a further aspect, a corn plant or seed disclosed herein exhibits a seed yield increase of about 4.5 quintal/hectare or more. In a further aspect, a corn plant or seed disclosed herein exhibits a seed yield increase of about 5 quintal/hectare or more. In a further aspect, a corn plant or seed disclosed herein exhibits a seed yield increase of about 6 quintal/hectare or more. In a further aspect, a corn plant or seed disclosed herein exhibits a seed yield increase of about 7 quintal/hectare or more. In a further aspect, a corn plant or seed disclosed herein exhibits a seed yield increase of about 8 quintal/hectare or more. In a further aspect, a corn plant or seed disclosed herein exhibits a seed yield increase of about 9 quintal/hectare or more. In a further aspect, a corn plant or seed disclosed herein exhibits a seed yield increase of about 10 quintal/hectare or more.

In an aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the three or more LW resistance QTLs under a similar growth condition (e.g., a high LW stress condition). In a further aspect, a corn plant or seed disclosed herein exhibits a seed yield increase of about 0.1 quintal/hectare or more. In a further aspect, a corn plant or seed disclosed herein exhibits a seed yield increase of about 0.25 quintal/hectare or more. In a further aspect, a corn plant or seed disclosed herein exhibits a seed yield increase of about 0.5 quintal/hectare or more. In a further aspect, a corn plant or seed disclosed herein exhibits a seed yield increase of about 0.75 quintal/hectare or more. In a further aspect, a corn plant or seed disclosed herein exhibits a seed yield increase of about 1 quintal/hectare or more. In a further aspect, a corn plant or seed disclosed herein exhibits a seed yield increase of about 1.5 quintal/hectare or more. In a further aspect, a corn plant or seed disclosed herein exhibits a seed yield increase of about 2 quintal/hectare or more. In a further aspect, a corn plant or seed disclosed herein exhibits a seed yield increase of about 2.5 quintal/hectare or more. In a further aspect, a corn plant or seed disclosed herein exhibits a seed yield increase of about 3 quintal/hectare or more. In a further aspect, a corn plant or seed disclosed herein exhibits a seed yield increase of about 3.5 quintal/hectare or more. In a further aspect, a corn plant or seed disclosed herein exhibits a seed yield increase of about 4 quintal/hectare or more. In a further aspect, a corn plant or seed disclosed herein exhibits a seed yield increase of about 4.5 quintal/hectare or more. In a further aspect, a corn plant or seed disclosed herein exhibits a seed yield increase of about 5 quintal/hectare or more. In a further aspect, a corn plant or seed disclosed herein exhibits a seed yield increase of about 6 quintal/hectare or more. In a further aspect, a corn plant or seed disclosed herein exhibits a seed yield increase of about 7 quintal/hectare or more. In a further aspect, a corn plant or seed disclosed herein exhibits a seed yield increase of about 8 quintal/hectare or more. In a further aspect, a corn plant or seed disclosed herein exhibits a seed yield increase of about 9 quintal/hectare or more. In a further aspect, a corn plant or seed disclosed herein exhibits a seed yield increase of about 10 quintal/hectare or more.

In an aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the four or more LW resistance QTLs under a similar growth condition (e.g., a high LW stress condition). In a further aspect, a corn plant or seed disclosed herein exhibits a seed yield increase of about 0.1 quintal/hectare or more. In a further aspect, a corn plant or seed disclosed herein exhibits a seed yield increase of about 0.25 quintal/hectare or more. In a further aspect, a corn plant or seed disclosed herein exhibits a seed yield increase of about 0.5 quintal/hectare or more. In a further aspect, a corn plant or seed disclosed herein exhibits a seed yield increase of about 0.75 quintal/hectare or more. In a further aspect, a corn plant or seed disclosed herein exhibits a seed yield increase of about 1 quintal/hectare or more. In a further aspect, a corn plant or seed disclosed herein exhibits a seed yield increase of about 1.5 quintal/hectare or more. In a further aspect, a corn plant or seed disclosed herein exhibits a seed yield increase of about 2 quintal/hectare or more. In a further aspect, a corn plant or seed disclosed herein exhibits a seed yield increase of about 2.5 quintal/hectare or more. In a further aspect, a corn plant or seed disclosed herein exhibits a seed yield increase of about 3 quintal/hectare or more. In a further aspect, a corn plant or seed disclosed herein exhibits a seed yield increase of about 3.5 quintal/hectare or more. In a further aspect, a corn plant or seed disclosed herein exhibits a seed yield increase of about 4 quintal/hectare or more. In a further aspect, a corn plant or seed disclosed herein exhibits a seed yield increase of about 4.5 quintal/hectare or more. In a further aspect, a corn plant or seed disclosed herein exhibits a seed yield increase of about 5 quintal/hectare or more. In a further aspect, a corn plant or seed disclosed herein exhibits a seed yield increase of about 6 quintal/hectare or more. In a further aspect, a corn plant or seed disclosed herein exhibits a seed yield increase of about 7 quintal/hectare or more. In a further aspect, a corn plant or seed disclosed herein exhibits a seed yield increase of about 8 quintal/hectare or more. In a further aspect, a corn plant or seed disclosed herein exhibits a seed yield increase of about 9 quintal/hectare or more. In a further aspect, a corn plant or seed disclosed herein exhibits a seed yield increase of about 10 quintal/hectare or more.

In an aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the five or more LW resistance QTLs under a similar growth condition (e.g., a high LW stress condition). In a further aspect, a corn plant or seed disclosed herein exhibits a seed yield increase of about 0.1 quintal/hectare or more. In a further aspect, a corn plant or seed disclosed herein exhibits a seed yield increase of about 0.25 quintal/hectare or more. In a further aspect, a corn plant or seed disclosed herein exhibits a seed yield increase of about 0.5 quintal/hectare or more. In a further aspect, a corn plant or seed disclosed herein exhibits a seed yield increase of about 0.75 quintal/hectare or more. In a further aspect, a corn plant or seed disclosed herein exhibits a seed yield increase of about 1 quintal/hectare or more. In a further aspect, a corn plant or seed disclosed herein exhibits a seed yield increase of about 1.5 quintal/hectare or more. In a further aspect, a corn plant or seed disclosed herein exhibits a seed yield increase of about 2 quintal/hectare or more. In a further aspect, a corn plant or seed disclosed herein exhibits a seed yield increase of about 2.5 quintal/hectare or more. In a further aspect, a corn plant or seed disclosed herein exhibits a seed yield increase of about 3 quintal/hectare or more. In a further aspect, a corn plant or seed disclosed herein exhibits a seed yield increase of about 3.5 quintal/hectare or more. In a further aspect, a corn plant or seed disclosed herein exhibits a seed yield increase of about 4 quintal/hectare or more. In a further aspect, a corn plant or seed disclosed herein exhibits a seed yield increase of about 4.5 quintal/hectare or more. In a further aspect, a corn plant or seed disclosed herein exhibits a seed yield increase of about 5 quintal/hectare or more. In a further aspect, a corn plant or seed disclosed herein exhibits a seed yield increase of about 6 quintal/hectare or more. In a further aspect, a corn plant or seed disclosed herein exhibits a seed yield increase of about 7 quintal/hectare or more. In a further aspect, a corn plant or seed disclosed herein exhibits a seed yield increase of about 8 quintal/hectare or more. In a further aspect, a corn plant or seed disclosed herein exhibits a seed yield increase of about 9 quintal/hectare or more. In a further aspect, a corn plant or seed disclosed herein exhibits a seed yield increase of about 10 quintal/hectare or more.

In an aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the six or more LW resistance QTLs under a similar growth condition (e.g., a high LW stress condition). In a further aspect, a corn plant or seed disclosed herein exhibits a seed yield increase of about 0.1 quintal/hectare or more. In a further aspect, a corn plant or seed disclosed herein exhibits a seed yield increase of about 0.25 quintal/hectare or more. In a further aspect, a corn plant or seed disclosed herein exhibits a seed yield increase of about 0.5 quintal/hectare or more. In a further aspect, a corn plant or seed disclosed herein exhibits a seed yield increase of about 0.75 quintal/hectare or more. In a further aspect, a corn plant or seed disclosed herein exhibits a seed yield increase of about 1 quintal/hectare or more. In a further aspect, a corn plant or seed disclosed herein exhibits a seed yield increase of about 1.5 quintal/hectare or more. In a further aspect, a corn plant or seed disclosed herein exhibits a seed yield increase of about 2 quintal/hectare or more. In a further aspect, a corn plant or seed disclosed herein exhibits a seed yield increase of about 2.5 quintal/hectare or more. In a further aspect, a corn plant or seed disclosed herein exhibits a seed yield increase of about 3 quintal/hectare or more. In a further aspect, a corn plant or seed disclosed herein exhibits a seed yield increase of about 3.5 quintal/hectare or more. In a further aspect, a corn plant or seed disclosed herein exhibits a seed yield increase of about 4 quintal/hectare or more. In a further aspect, a corn plant or seed disclosed herein exhibits a seed yield increase of about 4.5 quintal/hectare or more. In a further aspect, a corn plant or seed disclosed herein exhibits a seed yield increase of about 5 quintal/hectare or more. In a further aspect, a corn plant or seed disclosed herein exhibits a seed yield increase of about 6 quintal/hectare or more. In a further aspect, a corn plant or seed disclosed herein exhibits a seed yield increase of about 7 quintal/hectare or more. In a further aspect, a corn plant or seed disclosed herein exhibits a seed yield increase of about 8 quintal/hectare or more. In a further aspect, a corn plant or seed disclosed herein exhibits a seed yield increase of about 9 quintal/hectare or more. In a further aspect, a corn plant or seed disclosed herein exhibits a seed yield increase of about 10 quintal/hectare or more.

In an aspect, a corn plant or seed provided herein comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the one or more LW resistance QTLs under a similar growth condition (e.g., a high LW stress condition). In a further aspect, a corn plant or seed disclosed herein exhibits a seed yield increase of between 0.1 and 10 quintal/hectare. In a further aspect, a corn plant or seed disclosed herein exhibits a seed yield increase of between 0.1 and 9 quintal/hectare. In a further aspect, a corn plant or seed disclosed herein exhibits a seed yield increase of between 0.1 and 8 quintal/hectare. In a further aspect, a corn plant or seed disclosed herein exhibits a seed yield increase of between 0.1 and 7 quintal/hectare. In a further aspect, a corn plant or seed disclosed herein exhibits a seed yield increase of between 0.1 and 6 quintal/hectare. In a further aspect, a corn plant or seed disclosed herein exhibits a seed yield increase of between 0.1 and 5 quintal/hectare. In a further aspect, a corn plant or seed disclosed herein exhibits a seed yield increase of between 0.1 and 4.5 quintal/hectare. In a further aspect, a corn plant or seed disclosed herein exhibits a seed yield increase of between 0.1 and 4 quintal/hectare. In a further aspect, a corn plant or seed disclosed herein exhibits a seed yield increase of between 0.1 and 3.5 quintal/hectare. In a further aspect, a corn plant or seed disclosed herein exhibits a seed yield increase of between 0.1 and 3 quintal/hectare. In a further aspect, a corn plant or seed disclosed herein exhibits a seed yield increase of between 0.1 and 2.5 quintal/hectare. In a further aspect, a corn plant or seed disclosed herein exhibits a seed yield increase of between 0.1 and 2 quintal/hectare. In a further aspect, a corn plant or seed disclosed herein exhibits a seed yield increase of between 0.1 and 1.5 quintal/hectare. In a further aspect, a corn plant or seed disclosed herein exhibits a seed yield increase of between 0.1 and 1 quintal/hectare. In a further aspect, a corn plant or seed disclosed herein exhibits a seed yield increase of between 0.1 and 0.75 quintal/hectare. In a further aspect, a corn plant or seed disclosed herein exhibits a seed yield increase of between 0.1 and 0.5 quintal/hectare. In a further aspect, a corn plant or seed disclosed herein exhibits a seed yield increase of between 0.1 and 0.25 quintal/hectare. In a further aspect, a corn plant or seed disclosed herein exhibits a seed yield increase of between 0.25 and 9 quintal/hectare. In a further aspect, a corn plant or seed disclosed herein exhibits a seed yield increase of between 0.5 and 8 quintal/hectare. In a further aspect, a corn plant or seed disclosed herein exhibits a seed yield increase of between 0.75 and 7 quintal/hectare. In a further aspect, a corn plant or seed disclosed herein exhibits a seed yield increase of between 1 and 6 quintal/hectare. In a further aspect, a corn plant or seed disclosed herein exhibits a seed yield increase of between 1.5 and 5 quintal/hectare. In a further aspect, a corn plant or seed disclosed herein exhibits a seed yield increase of between 2 and 4.5 quintal/hectare. In a further aspect, a corn plant or seed disclosed herein exhibits a seed yield increase of between 2.5 and 4 quintal/hectare. In a further aspect, a corn plant or seed disclosed herein exhibits a seed yield increase of between 3 and 3.5 quintal/hectare higher.

In an aspect, a corn plant or seed provided herein comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the two or more LW resistance QTLs under a similar growth condition (e.g., a high LW stress condition). In a further aspect, a corn plant or seed disclosed herein exhibits a seed yield increase of between 0.1 and 10 quintal/hectare. In a further aspect, a corn plant or seed disclosed herein exhibits a seed yield increase of between 0.1 and 9 quintal/hectare. In a further aspect, a corn plant or seed disclosed herein exhibits a seed yield increase of between 0.1 and 8 quintal/hectare. In a further aspect, a corn plant or seed disclosed herein exhibits a seed yield increase of between 0.1 and 7 quintal/hectare. In a further aspect, a corn plant or seed disclosed herein exhibits a seed yield increase of between 0.1 and 6 quintal/hectare. In a further aspect, a corn plant or seed disclosed herein exhibits a seed yield increase of between 0.1 and 5 quintal/hectare. In a further aspect, a corn plant or seed disclosed herein exhibits a seed yield increase of between 0.1 and 4.5 quintal/hectare. In a further aspect, a corn plant or seed disclosed herein exhibits a seed yield increase of between 0.1 and 4 quintal/hectare. In a further aspect, a corn plant or seed disclosed herein exhibits a seed yield increase of between 0.1 and 3.5 quintal/hectare. In a further aspect, a corn plant or seed disclosed herein exhibits a seed yield increase of between 0.1 and 3 quintal/hectare. In a further aspect, a corn plant or seed disclosed herein exhibits a seed yield increase of between 0.1 and 2.5 quintal/hectare. In a further aspect, a corn plant or seed disclosed herein exhibits a seed yield increase of between 0.1 and 2 quintal/hectare. In a further aspect, a corn plant or seed disclosed herein exhibits a seed yield increase of between 0.1 and 1.5 quintal/hectare. In a further aspect, a corn plant or seed disclosed herein exhibits a seed yield increase of between 0.1 and 1 quintal/hectare. In a further aspect, a corn plant or seed disclosed herein exhibits a seed yield increase of between 0.1 and 0.75 quintal/hectare. In a further aspect, a corn plant or seed disclosed herein exhibits a seed yield increase of between 0.1 and 0.5 quintal/hectare. In a further aspect, a corn plant or seed disclosed herein exhibits a seed yield increase of between 0.1 and 0.25 quintal/hectare. In a further aspect, a corn plant or seed disclosed herein exhibits a seed yield increase of between 0.25 and 9 quintal/hectare. In a further aspect, a corn plant or seed disclosed herein exhibits a seed yield increase of between 0.5 and 8 quintal/hectare. In a further aspect, a corn plant or seed disclosed herein exhibits a seed yield increase of between 0.75 and 7 quintal/hectare. In a further aspect, a corn plant or seed disclosed herein exhibits a seed yield increase of between 1 and 6 quintal/hectare. In a further aspect, a corn plant or seed disclosed herein exhibits a seed yield increase of between 1.5 and 5 quintal/hectare. In a further aspect, a corn plant or seed disclosed herein exhibits a seed yield increase of between 2 and 4.5 quintal/hectare. In a further aspect, a corn plant or seed disclosed herein exhibits a seed yield increase of between 2.5 and 4 quintal/hectare. In a further aspect, a corn plant or seed disclosed herein exhibits a seed yield increase of between 3 and 3.5 quintal/hectare higher.

In an aspect, a corn plant or seed provided herein comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the three or more LW resistance QTLs under a similar growth condition (e.g., a high LW stress condition). In a further aspect, a corn plant or seed disclosed herein exhibits a seed yield increase of between 0.1 and 10 quintal/hectare. In a further aspect, a corn plant or seed disclosed herein exhibits a seed yield increase of between 0.1 and 9 quintal/hectare. In a further aspect, a corn plant or seed disclosed herein exhibits a seed yield increase of between 0.1 and 8 quintal/hectare. In a further aspect, a corn plant or seed disclosed herein exhibits a seed yield increase of between 0.1 and 7 quintal/hectare. In a further aspect, a corn plant or seed disclosed herein exhibits a seed yield increase of between 0.1 and 6 quintal/hectare. In a further aspect, a corn plant or seed disclosed herein exhibits a seed yield increase of between 0.1 and 5 quintal/hectare. In a further aspect, a corn plant or seed disclosed herein exhibits a seed yield increase of between 0.1 and 4.5 quintal/hectare. In a further aspect, a corn plant or seed disclosed herein exhibits a seed yield increase of between 0.1 and 4 quintal/hectare. In a further aspect, a corn plant or seed disclosed herein exhibits a seed yield increase of between 0.1 and 3.5 quintal/hectare. In a further aspect, a corn plant or seed disclosed herein exhibits a seed yield increase of between 0.1 and 3 quintal/hectare. In a further aspect, a corn plant or seed disclosed herein exhibits a seed yield increase of between 0.1 and 2.5 quintal/hectare. In a further aspect, a corn plant or seed disclosed herein exhibits a seed yield increase of between 0.1 and 2 quintal/hectare. In a further aspect, a corn plant or seed disclosed herein exhibits a seed yield increase of between 0.1 and 1.5 quintal/hectare. In a further aspect, a corn plant or seed disclosed herein exhibits a seed yield increase of between 0.1 and 1 quintal/hectare. In a further aspect, a corn plant or seed disclosed herein exhibits a seed yield increase of between 0.1 and 0.75 quintal/hectare. In a further aspect, a corn plant or seed disclosed herein exhibits a seed yield increase of between 0.1 and 0.5 quintal/hectare. In a further aspect, a corn plant or seed disclosed herein exhibits a seed yield increase of between 0.1 and 0.25 quintal/hectare. In a further aspect, a corn plant or seed disclosed herein exhibits a seed yield increase of between 0.25 and 9 quintal/hectare. In a further aspect, a corn plant or seed disclosed herein exhibits a seed yield increase of between 0.5 and 8 quintal/hectare. In a further aspect, a corn plant or seed disclosed herein exhibits a seed yield increase of between 0.75 and 7 quintal/hectare. In a further aspect, a corn plant or seed disclosed herein exhibits a seed yield increase of between 1 and 6 quintal/hectare. In a further aspect, a corn plant or seed disclosed herein exhibits a seed yield increase of between 1.5 and 5 quintal/hectare. In a further aspect, a corn plant or seed disclosed herein exhibits a seed yield increase of between 2 and 4.5 quintal/hectare. In a further aspect, a corn plant or seed disclosed herein exhibits a seed yield increase of between 2.5 and 4 quintal/hectare. In a further aspect, a corn plant or seed disclosed herein exhibits a seed yield increase of between 3 and 3.5 quintal/hectare higher.

In an aspect, a corn plant or seed provided herein comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the four or more LW resistance QTLs under a similar growth condition (e.g., a high LW stress condition). In a further aspect, a corn plant or seed disclosed herein exhibits a seed yield increase of between 0.1 and 10 quintal/hectare. In a further aspect, a corn plant or seed disclosed herein exhibits a seed yield increase of between 0.1 and 9 quintal/hectare. In a further aspect, a corn plant or seed disclosed herein exhibits a seed yield increase of between 0.1 and 8 quintal/hectare. In a further aspect, a corn plant or seed disclosed herein exhibits a seed yield increase of between 0.1 and 7 quintal/hectare. In a further aspect, a corn plant or seed disclosed herein exhibits a seed yield increase of between 0.1 and 6 quintal/hectare. In a further aspect, a corn plant or seed disclosed herein exhibits a seed yield increase of between 0.1 and 5 quintal/hectare. In a further aspect, a corn plant or seed disclosed herein exhibits a seed yield increase of between 0.1 and 4.5 quintal/hectare. In a further aspect, a corn plant or seed disclosed herein exhibits a seed yield increase of between 0.1 and 4 quintal/hectare. In a further aspect, a corn plant or seed disclosed herein exhibits a seed yield increase of between 0.1 and 3.5 quintal/hectare. In a further aspect, a corn plant or seed disclosed herein exhibits a seed yield increase of between 0.1 and 3 quintal/hectare. In a further aspect, a corn plant or seed disclosed herein exhibits a seed yield increase of between 0.1 and 2.5 quintal/hectare. In a further aspect, a corn plant or seed disclosed herein exhibits a seed yield increase of between 0.1 and 2 quintal/hectare. In a further aspect, a corn plant or seed disclosed herein exhibits a seed yield increase of between 0.1 and 1.5 quintal/hectare. In a further aspect, a corn plant or seed disclosed herein exhibits a seed yield increase of between 0.1 and 1 quintal/hectare. In a further aspect, a corn plant or seed disclosed herein exhibits a seed yield increase of between 0.1 and 0.75 quintal/hectare. In a further aspect, a corn plant or seed disclosed herein exhibits a seed yield increase of between 0.1 and 0.5 quintal/hectare. In a further aspect, a corn plant or seed disclosed herein exhibits a seed yield increase of between 0.1 and 0.25 quintal/hectare. In a further aspect, a corn plant or seed disclosed herein exhibits a seed yield increase of between 0.25 and 9 quintal/hectare. In a further aspect, a corn plant or seed disclosed herein exhibits a seed yield increase of between 0.5 and 8 quintal/hectare. In a further aspect, a corn plant or seed disclosed herein exhibits a seed yield increase of between 0.75 and 7 quintal/hectare. In a further aspect, a corn plant or seed disclosed herein exhibits a seed yield increase of between 1 and 6 quintal/hectare. In a further aspect, a corn plant or seed disclosed herein exhibits a seed yield increase of between 1.5 and 5 quintal/hectare. In a further aspect, a corn plant or seed disclosed herein exhibits a seed yield increase of between 2 and 4.5 quintal/hectare. In a further aspect, a corn plant or seed disclosed herein exhibits a seed yield increase of between 2.5 and 4 quintal/hectare. In a further aspect, a corn plant or seed disclosed herein exhibits a seed yield increase of between 3 and 3.5 quintal/hectare higher.

In an aspect, a corn plant or seed provided herein comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the five or more LW resistance QTLs under a similar growth condition (e.g., a high LW stress condition). In a further aspect, a corn plant or seed disclosed herein exhibits a seed yield increase of between 0.1 and 10 quintal/hectare. In a further aspect, a corn plant or seed disclosed herein exhibits a seed yield increase of between 0.1 and 9 quintal/hectare. In a further aspect, a corn plant or seed disclosed herein exhibits a seed yield increase of between 0.1 and 8 quintal/hectare. In a further aspect, a corn plant or seed disclosed herein exhibits a seed yield increase of between 0.1 and 7 quintal/hectare. In a further aspect, a corn plant or seed disclosed herein exhibits a seed yield increase of between 0.1 and 6 quintal/hectare. In a further aspect, a corn plant or seed disclosed herein exhibits a seed yield increase of between 0.1 and 5 quintal/hectare. In a further aspect, a corn plant or seed disclosed herein exhibits a seed yield increase of between 0.1 and 4.5 quintal/hectare. In a further aspect, a corn plant or seed disclosed herein exhibits a seed yield increase of between 0.1 and 4 quintal/hectare. In a further aspect, a corn plant or seed disclosed herein exhibits a seed yield increase of between 0.1 and 3.5 quintal/hectare. In a further aspect, a corn plant or seed disclosed herein exhibits a seed yield increase of between 0.1 and 3 quintal/hectare. In a further aspect, a corn plant or seed disclosed herein exhibits a seed yield increase of between 0.1 and 2.5 quintal/hectare. In a further aspect, a corn plant or seed disclosed herein exhibits a seed yield increase of between 0.1 and 2 quintal/hectare. In a further aspect, a corn plant or seed disclosed herein exhibits a seed yield increase of between 0.1 and 1.5 quintal/hectare. In a further aspect, a corn plant or seed disclosed herein exhibits a seed yield increase of between 0.1 and 1 quintal/hectare. In a further aspect, a corn plant or seed disclosed herein exhibits a seed yield increase of between 0.1 and 0.75 quintal/hectare. In a further aspect, a corn plant or seed disclosed herein exhibits a seed yield increase of between 0.1 and 0.5 quintal/hectare. In a further aspect, a corn plant or seed disclosed herein exhibits a seed yield increase of between 0.1 and 0.25 quintal/hectare. In a further aspect, a corn plant or seed disclosed herein exhibits a seed yield increase of between 0.25 and 9 quintal/hectare. In a further aspect, a corn plant or seed disclosed herein exhibits a seed yield increase of between 0.5 and 8 quintal/hectare. In a further aspect, a corn plant or seed disclosed herein exhibits a seed yield increase of between 0.75 and 7 quintal/hectare. In a further aspect, a corn plant or seed disclosed herein exhibits a seed yield increase of between 1 and 6 quintal/hectare. In a further aspect, a corn plant or seed disclosed herein exhibits a seed yield increase of between 1.5 and 5 quintal/hectare. In a further aspect, a corn plant or seed disclosed herein exhibits a seed yield increase of between 2 and 4.5 quintal/hectare. In a further aspect, a corn plant or seed disclosed herein exhibits a seed yield increase of between 2.5 and 4 quintal/hectare. In a further aspect, a corn plant or seed disclosed herein exhibits a seed yield increase of between 3 and 3.5 quintal/hectare higher.

In an aspect, a corn plant or seed provided herein comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 exhibits a seed yield increase higher than the seed yield of a corn plant or seed without the six or more LW resistance QTLs under a similar growth condition (e.g., a high LW stress condition). In a further aspect, a corn plant or seed disclosed herein exhibits a seed yield increase of between 0.1 and 10 quintal/hectare. In a further aspect, a corn plant or seed disclosed herein exhibits a seed yield increase of between 0.1 and 9 quintal/hectare. In a further aspect, a corn plant or seed disclosed herein exhibits a seed yield increase of between 0.1 and 8 quintal/hectare. In a further aspect, a corn plant or seed disclosed herein exhibits a seed yield increase of between 0.1 and 7 quintal/hectare. In a further aspect, a corn plant or seed disclosed herein exhibits a seed yield increase of between 0.1 and 6 quintal/hectare. In a further aspect, a corn plant or seed disclosed herein exhibits a seed yield increase of between 0.1 and 5 quintal/hectare. In a further aspect, a corn plant or seed disclosed herein exhibits a seed yield increase of between 0.1 and 4.5 quintal/hectare. In a further aspect, a corn plant or seed disclosed herein exhibits a seed yield increase of between 0.1 and 4 quintal/hectare. In a further aspect, a corn plant or seed disclosed herein exhibits a seed yield increase of between 0.1 and 3.5 quintal/hectare. In a further aspect, a corn plant or seed disclosed herein exhibits a seed yield increase of between 0.1 and 3 quintal/hectare. In a further aspect, a corn plant or seed disclosed herein exhibits a seed yield increase of between 0.1 and 2.5 quintal/hectare. In a further aspect, a corn plant or seed disclosed herein exhibits a seed yield increase of between 0.1 and 2 quintal/hectare. In a further aspect, a corn plant or seed disclosed herein exhibits a seed yield increase of between 0.1 and 1.5 quintal/hectare. In a further aspect, a corn plant or seed disclosed herein exhibits a seed yield increase of between 0.1 and 1 quintal/hectare. In a further aspect, a corn plant or seed disclosed herein exhibits a seed yield increase of between 0.1 and 0.75 quintal/hectare. In a further aspect, a corn plant or seed disclosed herein exhibits a seed yield increase of between 0.1 and 0.5 quintal/hectare. In a further aspect, a corn plant or seed disclosed herein exhibits a seed yield increase of between 0.1 and 0.25 quintal/hectare. In a further aspect, a corn plant or seed disclosed herein exhibits a seed yield increase of between 0.25 and 9 quintal/hectare. In a further aspect, a corn plant or seed disclosed herein exhibits a seed yield increase of between 0.5 and 8 quintal/hectare. In a further aspect, a corn plant or seed disclosed herein exhibits a seed yield increase of between 0.75 and 7 quintal/hectare. In a further aspect, a corn plant or seed disclosed herein exhibits a seed yield increase of between 1 and 6 quintal/hectare. In a further aspect, a corn plant or seed disclosed herein exhibits a seed yield increase of between 1.5 and 5 quintal/hectare. In a further aspect, a corn plant or seed disclosed herein exhibits a seed yield increase of between 2 and 4.5 quintal/hectare. In a further aspect, a corn plant or seed disclosed herein exhibits a seed yield increase of between 2.5 and 4 quintal/hectare. In a further aspect, a corn plant or seed disclosed herein exhibits a seed yield increase of between 3 and 3.5 quintal/hectare higher.

In an aspect, this disclosure provides an LW resistant corn plant or seed comprising one or more, two or more, three or more, four or more, five or more, or six or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 obtainable, obtained, or introgressed from any one of corn lines CV131061, CV806292, CV137694, and CV138811.

In an aspect, this disclosure provides a method comprising providing a set of corn seeds comprising one or more, two or more, three or more, four or more, five or more, or six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting the set of corn seeds in a field plot. In an aspect, a method comprising growing corn plants a field plot that exhibits LW infection in any one of the previous one or more, two or more, three or more, four or more, five or more, six or more, seven or more, eight or more, nine or more, or ten or more planting seasons.

In an aspect, a method, a corn plant, or a corn seed provided herein is used in combination with one or more pesticides including, but not limited to, herbicides, fungicides (e.g., picoxystrobin, cyproconazole, tetraconazole, pyraclostrobin, metconazole, azoxystrobin, propiconazole, prothioconazole, trifloxystrobin), insecticides, microbiocides, nematicides, insect repellents, bactericides, and other substances used to control pests. In another aspect, a method, a corn plant, or a corn seed provided herein is used in combination with one or more triazoles, strobilurins, acylamino acids, pyrimidines, pyridines, arylphenyl ketones, amides, benzanilides, imidazoles, dinitrophenols, morpholines, phenylsulfamides and organophosphorus cpds, derivatives thereof and combinations thereof which can be applied as a seed treatment, a foliar treatment, a drench treatment, or a drip treatment.

In an aspect, corn seeds provided herein are untreated. In another aspect, corn seeds provided herein can be subjected to various and multiple treatments. For example, without being limiting, the seeds can be treated to improve germination by priming the seeds, by disinfection to protect against seed borne pathogens, or both priming and disinfection. In another example, seeds can be coated with any available coating to improve, for example, plantability, seed emergence, and protection against seed borne pathogens. Seed coating can be any form of seed coating including, but not limited to, pelleting, film coating, and encrustments.

In a further example, the disclosure provides methods to enhance LW resistance by combining two or more LW resistance QTLs provided herein. In an aspect, the combined LW resistance QTLs have additive effects in providing LW resistance. In another aspect, the combined LW resistance QTLs have synergistic effects in providing LW resistance. In a further aspect, the combination of two or more, three or more, four or more, five or more, or six or more LW resistance QTLs provided herein has no negative effects over corn physiology, resistance, yield, or performance in general.

In an aspect, this disclosure provides corn plant cells, tissues, and organs that are not reproductive material and do not mediate the natural reproduction of the plant. In another aspect, this disclosure also provides corn plant cells, tissues, and organs that are reproductive material and mediate the natural reproduction of the plant. In another aspect, this disclosure provides corn plant cells, tissues, and organs that cannot maintain themselves via photosynthesis. In another aspect, this disclosure provides somatic corn plant cells. Somatic cells, contrary to germline cells, do not mediate plant reproduction.

As an example, the provided cells, tissues and organs can be from seed, fruit, leaf, leaf blade, leaf sheath, auricle, ligule, cotyledon, hypocotyl, meristem, embryos, endosperm, root, shoot, stem, pod, flower, inflorescence, stalk, pedicel, style, stigma, receptacle, petal, sepal, pollen, anther, filament, ovary, ovule, pericarp, phloem, bud, or vascular tissue. In another example, this disclosure provides a corn plant chloroplast or mitochondria. In a further example, this disclosure provides epidermal cells, stomata cell, trichomes, root hairs, a storage root, or a tuber. In another example, this disclosure provides a corn protoplast.

Skilled artisans understand that corn plants naturally reproduce via seeds, not via asexual reproduction or vegetative propagation. In an example, this disclosure provides corn endosperm. In another example, this disclosure provides corn endosperm cells. In a further example, this disclosure provides a male or female sterile corn plant, which cannot reproduce without human intervention.

In a further aspect, this disclosure provides processed products made from a provided corn plant or seed. As an example, such products include, but are not limited to, meal, oil, plant extract, starch, fermentation products, or digestion products. In another example, this disclosure also provides a corn meal, which is substantially oil free and which is produced using the oilseed of any of the plants provided herein. In another example, this disclosure also provides a method of providing a corn meal by crushing oilseed of any of the plants provided herein.

A corn plant or seed provided herein can also be genetically engineered to express various phenotypes of agronomic interest. Exemplary genes implicated in this regard include, but are not limited to, genes that confer resistance to pests or disease, genes that confer resistance or tolerance to an herbicide, genes that control male sterility, genes that affect abiotic stress resistance, and other genes and transcription factors that affect plant growth and agronomic traits such as yield, flowering, plant growth, or plant architecture.

Corn Transformation

A corn plant or seed provided herein can be genetically transformed. Numerous methods for plant transformation have been developed including biological and physical plant transformation protocols. See, for example, Mild et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

One method for introducing an expression vector into plants is based on the natural transformation system of *Agrobacterium*. See, e.g., Horsch et al., A Simple and General Method for Transferring Genes into Plants. *Science*, 227:1229-1231 (1985). *A. tumefaciens* and *A. rhizogenes* are plant pathogenic soil bacteria which genetically transform plant cells. Descriptions of *Agrobacterium* vector systems and methods for *Agrobacterium*-mediated gene transfer are provided by, for example, U.S. Pat. No. 5,563,055, incorporated herein by reference in its entirety.

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes.

Another method for physical delivery of DNA to plants is sonication of target cells. Alternatively, liposome and spheroplast fusion have been used to introduce expression vectors into plants. Electroporation of protoplasts and whole cells and tissues can also be used.

Following transformation of corn target tissues, expression of the above-described selectable marker genes allows for preferential selection of transformed cells, tissues, and/or plants, using regeneration and selection methods well-known in the art.

The foregoing methods for transformation would typically be used for producing a transgenic variety. The transgenic variety could then be crossed with another (non-transformed or transformed) variety, in order to produce a new transgenic variety. Alternatively, a genetic trait which has been engineered into a particular corn line using the foregoing transformation techniques could be moved into another line using traditional backcrossing techniques that are well-known in the plant breeding arts. For example, a backcrossing approach could be used to move an engineered trait from a public, non-elite variety into an elite variety, or from a variety containing a foreign gene in its genome into a variety or varieties which do not contain that gene.

A corn plant or seed provided herein can also be produced by one or more genome engineering techniques or subject to further genomic editing. For example, one or more LW resistance alleles can be introduced into an LW susceptible background. Exemplary genome engineering techniques include meganucleases, zinc-finger nucleases, TALENs, and CRISPR/Cas9 systems. See, e.g., Gaj et al., ZFN, TALEN, and CRISPR/Cas-based methods for genome engineering. *Trends in Biotechnology*, 31:397-405 (2013). Additional genome engineering techniques known to those of ordinary skill in the art are also envisioned.

Additional Breeding

A corn plant or seed provided herein can also be subject to additional breeding using one or more known methods in the art, e.g., pedigree breeding, recurrent selection, mass selection, and mutation breeding. Pedigree breeding starts with the crossing of two genotypes, such as a corn variety comprising an LW resistance QTL or LW resistance allele provided herein and another corn variety lacking such a locus. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-fertilization and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. The developed variety can comprise homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a corn variety can be crossed with another variety to produce a first generation progeny plant. The first generation progeny plant can then be backcrossed to one of its parent varieties to create a $BC_1$ or $BC_2$. Progenies are selfed and selected so that the newly developed variety has many of the attributes of the recurrent parent and yet several of the desired attributes of the non-recurrent parent. This approach leverages the value and strengths of the recurrent parent for use in new corn varieties.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic line. A synthetic line is the resultant progeny formed by the intercrossing of several selected varieties.

Mass selection is another useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self-pollination, directed pollination could be used as part of the breeding program.

Mutation breeding can also be used to introduce new traits into a corn plant or seed provided herein. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, gamma rays (e.g., cobalt-60 or cesium-137), neutrons (product of nuclear fission by uranium-235 in an atomic reactor), beta radiation (emitted from radioisotopes such as phosphorus-32 or carbon-14), or ultraviolet radiation (from 2500 to 2900 nm)), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines). Transposon- or T-DNA-based mutagenesis is also encompassed by the present disclosure. Once a desired trait is observed through mutagenesis the trait can then be incorporated into existing germplasm by traditional breeding techniques.

In an aspect, the disclosure provides a doubled haploid corn plant and seed that comprise an LW resistance QTL or LW resistance marker alleles provided herein. The doubled haploid approach achieves isogenic plants in a shorter time frame, and is particularly useful for generating inbred lines and quantitative genetics studies. Doubled haploid plants can be produced according to methods known in the art. For example, the initial step involves the haploidization of the plant which results in the production of a population comprising haploid seed. Non-homozygous lines are crossed with an inducer parent, resulting in the production of haploid seeds. Seeds that have haploid embryos, but normal triploid endosperm, advance to the second stage. After selecting haploid seeds from the population, the selected seeds undergo chromosome doubling to produce doubled haploid seeds. A spontaneous chromosome doubling in a cell lineage will lead to normal gamete production or the production of unreduced gametes from haploid cell lineages. Application of a chemical compound, such as colchicine, can be used to increase the rate of diploidization. Colchicine binds to tubulin and prevents its polymerization into microtubules, thus arresting mitosis at metaphase, can be used to increase the rate of diploidization, i.e. doubling of the chromosome number. These chimeric plants are self-pollinated to produce diploid (doubled haploid) seed. This doubled haploid seed is cultivated and subsequently evaluated and used in hybrid testcross production.

In an aspect, this disclosure also provides methods for making a substantially homozygous corn plant by producing or obtaining a seed from a cross of a corn plant comprising an LW resistance allele and another corn plant and applying doubled haploid methods to the $F_1$ seed or $F_1$ plant or to any successive filial generation.

Hybrid Production

In an aspect, this disclosure provides a hybrid corn plant or seed, and their production. The development of a corn hybrid in a corn plant breeding program generally involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in corn, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line, is a factor in the selection of improved corn lines that can be used as inbreds. Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. A pollination control system and effective transfer of pollen from one parent to the other offers improved plant breeding and an effective method for producing hybrid corn seed and plants. For example, a male sterility system can be used to produce corn hybrids.

Male sterility genes can increase the efficiency with which hybrids are made, in that they eliminate the need to physically emasculate the plant used as a female in a given cross. Where one desires to employ male-sterility systems, it can be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

Marker Detection

In an aspect, the present disclosure provides markers that are in linkage disequilibrium with at least one LW resistance QTL or LW resistance allele and can be used to select for LW resistance. Exemplary markers comprise SEQ ID NOs:1 to 51 and 256 to 264 with their LW resistance alleles shown in Table 4. Markers within approximately 20 cM or less of these exemplary markers can also be identified from the known art. Markers within approximately 15 cM or less of these exemplary markers can also be identified from the known art. Markers within approximately 10 cM or less of these exemplary markers can also be identified from the known art. Markers within approximately 5 cM or less of these exemplary markers can also be identified from the known art. Markers within approximately 4 cM or less of these exemplary markers can also be identified from the known art. Markers within approximately 3 cM or less of these exemplary markers can also be identified from the known art. Markers within approximately 2 cM or less of these exemplary markers can also be identified from the known art. Markers within approximately 1 cM or less of these exemplary markers can also be identified from the known art. Markers within approximately 0.5 cM or less of these exemplary markers can also be identified from the known art.

Genetic markers are distinguishable from each other (as well as from the plurality of alleles of any one particular marker) on the basis of polynucleotide length and/or sequence. In general, any differentially inherited polymorphic trait (including a nucleic acid polymorphism) that segregates among progeny is a potential genetic marker.

As a set, polymorphic markers serve as a useful tool for fingerprinting plants to inform the degree of identity of lines or varieties. These markers can form a basis for determining associations with phenotype and can be used to drive genetic gain. The implementation of marker-assisted selection is dependent on the ability to detect and analyze underlying genetic differences between individuals.

As an example, nucleic acid analysis methods include, but are not limited to, PCR-based detection methods, microarray methods, mass spectrometry-based methods, and/or nucleic acid sequencing methods. In an aspect, the detection of polymorphic sites in a sample of DNA, RNA, or cDNA can be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) using primer pairs that are capable of hybridizing to the proximal sequences that define a polymorphism in its double-stranded form. Methods for typing DNA based on mass spectrometry have been provided in U.S. Pat. Nos. 6,613,509 and 6,503,710, and references found therein.

Polymorphisms in DNA sequences can be detected or typed by a variety of effective methods well known in the art including, but not limited to, those provided in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981; and 7,250,252 all of which are incorporated herein by reference in their entireties. However, the compositions and methods of the present disclosure can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as provided in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe all of which are incorporated herein by reference in their entireties.

Target nucleic acid sequence can also be detected by probe ligation methods as provided in U.S. Pat. No. 5,800,944, which is incorporated herein by reference in its entirety, where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Large-scale identification of single-feature polymorphisms in complex genomes. *Genome Research*, 13:513-523 (2003); Cui et al., Detecting single-feature polymorphisms using oligonucleotide array and robustified projection pursuit. *Bioinformatics*, 21:3852-3858 (2005)). On any one microarray, it is expected there will be a plurality of target sequences, which can represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is provided in U.S. Pat. Nos. 6,799,122; 6,913,879; and 6,996,476.

Target nucleic acid sequence can also be detected by probe linking methods as provided in U.S. Pat. No. 5,616,464, which is incorporated herein by reference in its entirety, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other exemplary methods for detecting SNPs and Indels include single base extension (SBE) methods. Examples of SBE methods include, but are not limited to, those provided in U.S. Pat. Nos. 6,004,744; 6,013,431; 5,595,890; 5,762, 876; and 5,945,283. SBE methods are based on extension of a nucleotide primer that is adjacent to a polymorphism to incorporate a detectable nucleotide residue upon extension of the primer. In an aspect, the SBE method uses four synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third and fourth oligonucleotides (called extension primers) which are designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another exemplary method for detecting polymorphisms, SNPs and indels can be detected by methods provided in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g., by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

As an example, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), Pac-Bio (Menlo Park, Calif.) and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by Service, Gene sequencing: the race for the $1000 genome. *Science,* 311:1544-46 (2006).

In an example, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as BLAST®, or even simple word processors.

In an aspect, any of the aforementioned marker types can be employed in the context of this disclosure to identify chromosome intervals encompassing a genetic element that contributes to superior agronomic performance (e.g., corn LW resistance).

The markers to be used in the methods of the present disclosure should preferably be diagnostic of origin in order for inferences to be made about subsequent populations. Experience to date suggests that SNP markers can be ideal for mapping because the likelihood that a particular SNP allele is derived from independent origins in the extant populations of a particular species is very low. As such, SNP markers appear to be useful for tracking and assisting introgression of QTL, particularly in the case of genotypes.

Association Mapping

In an aspect, the present disclosure also provides chromosome intervals, marker loci, germplasm for conducting genome-wide association mapping for LW resistance. Exemplary chromosome intervals and marker loci are provided in Tables 4 and 6. Genome-wide association mapping is conducted to find signals of association for various complex traits by surveying genetic variation in the whole genome.

Association mapping relies on chromosomal recombination opportunities over a large number of generations, in the history of a species, which allows the removal of association between a QTL and any marker not tightly linked to it, thus improving the rate of discovery of true association (Jannink and Walsh, *Quantitative Genetics, Genomics and Plant Breeding*, Kang, Ed. CAB International, pp. 59-68 (2002)).

An approach used to link phenotypic variation with genetic loci is marker-trait association (MTA) mapping, also known as linkage disequilibrium (LD) mapping. LD mapping emerged as an important gene mapping tool in the early 1990's with the advent of high-throughput genotyping technology, and has been widely used in human genetics to identify genes affecting human diseases. This approach was introduced and began to be adopted in plant gene mapping studies in early 2000's (Flint-Garcia et al., Structure of linkage disequilibrium in plants. *Annual Review of Plant Biology,* 54:357-374 (2003)).

LD mapping assumes that the main cause for LD is linkage that binds loci on the same chromosome together in transmission to next generation. However, due to recombination events accumulated over many generations in a natural population, each chromosome has been shuffled deeply, so that the chromosome has been broken into many tiny regions where loci remain transmitted together, but loci from different regions tend to transmit independently as if they were from different chromosomes. Chromosomal regions where loci are bound together in transmission are commonly known as LD blocks (Reich et al., Linkage disequilibrium in the human genome. *Nature,* 411:199-204 (2001)). LD mapping identifies genes of interest through genetic markers on the LD blocks where the genes are located. This is done by detecting significant associations between the markers and the traits that the genes affect with a sample of unrelated individuals or a sample of unrelated pedigrees that are genotyped on a selected set of markers covering candidate gene regions or the whole genome, and phenotyped on a set of traits of interest.

Compared with traditional linkage mapping methods that are typically based on artificial biparental segregating populations (e.g., $F_2$, BC, doubled haploid, recombinant inbred line, etc.), LD mapping generally produces better mapping resolution, because of the smaller sizes of LD blocks. In addition, LD mapping is useful in identifying more than two functional alleles at associated markers in a germplasm. Further, LD mapping is efficient for evaluating natural populations.

Identification of QTLs

As an example, markers, alleles, and haplotypes provided herein can be used for identifying QTLs associated with LW resistance. The statistical principles of QTL identification include penalized regression analysis, ridge regression, single marker analysis, complex pedigree analysis, Bayesian MCMC, identity-by-descent analysis, interval mapping, composite interval mapping (CIM), joint linkage mapping, and Haseman-Elston regression.

A QTL can act through a single gene mechanism or by a polygenic mechanism. In an aspect, the present disclosure provides an LW resistance QTL interval, where an LW resistance QTL (or multiple LW resistance QTLs) that segregates with an LW resistance trait is contained in the chromosomal interval. As used herein, when a QTL (or multiple QTLs) segregates with the LW resistance trait, it is referred to herein as an "LW resistance locus" (or "LW resistance loci").

In an aspect of this disclosure, the boundaries of an LW resistance QTL interval are drawn to encompass markers that will be closely linked to or associated with one or more LW resistance QTLs. In other words, an LW resistance QTL interval is drawn such that any marker that lies within that interval (including the terminal markers that define the boundaries of the interval) is genetically linked to or associated with the LW resistance QTL. Each interval comprises at least one LW resistance QTL, and furthermore, can indeed comprise more than one LW resistance QTL. Close proximity of multiple QTLs in the same interval can obfuscate the correlation of a particular marker with a particular QTL, as one marker can demonstrate linkage to more than one QTL. Conversely, e.g., if two markers in close proximity show co-segregation with the desired phenotypic trait, it is sometimes unclear if each of those markers identifying the same QTL or two different QTLs. Regardless, knowledge of how many QTLs are in a particular interval is not necessary to make or practice the claimed subject matter.

As an example, the present disclosure also provides the mapping of additional SNP markers associated with or closely linked to one or more LW resistance QTLs provided herein. SNP markers are ideal for mapping because the likelihood that a particular SNP allele is derived from independent origins in the extant populations of a particular species is very low. As such, SNP markers are useful for tracking and assisting introgression of LW resistance QTLs, particularly in the case of haplotypes. In an aspect, a SNP marker is selected for mapping an LW resistance QTL based on the marker's genetic map position. In another aspect, a SNP marker is selected for mapping an LW resistance QTL based on the marker's physical map position.

The genetic linkage of additional marker molecules can be established by a gene mapping model such as, without limitation, the flanking marker model reported by Lander and Botstein, (Lander and Botstein, Mapping Mendelian Factors Underlying Quantitative Traits Using RFLP Linkage Maps. *Genetics,* 121:185-199 (1989)), and the interval mapping, based on maximum likelihood methods described by Lander and Botstein (supra), and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety).

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, (Lander and Botstein, Mapping Mendelian Factors Underlying Quantitative Traits Using RFLP Linkage Maps. *Genetics,* 121:185-199 (1989), and further described by Arús and Moreno-González, *Plant Breeding,* Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak and Lander, A Nonparametric Approach for Mapping Quantitative Trait Loci. *Genetics,* 139:1421-1428 (1995), the entirety of which is herein incorporated by reference). Multiple regression methods or models can be also be used, in which the trait is regressed on a large number of markers (Jansen, *Biometrics in Plant Breed,* van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding,* Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, High Resolution of Quantitative Traits Into Multiple Loci via Interval Mapping. *Genetics,* 136:1447-1455 (1994) and Zeng, Precision Mapping of Quantitative Trait Loci. *Genetics,* 136:1457-1468 (1994). Generally, the use of cofactors reduces the bias and sampling error of the estimated QTL positions (Utz and Melchinger, *Biometrics in Plant Breeding,* van Oijen, Jansen (eds.) Proceedings of the Ninth Meeting of the Eucarpia Section Biometrics in Plant Breeding, The Netherlands, pp.195-204 (1994)), thereby improving the precision and efficiency of QTL mapping (Zeng, Precision Mapping of Quantitative Trait Loci. *Genetics,* 136:1457-1468 (1994)). These models can be extended to multi-environment experiments to analyze genotype-environment interactions (Jansen et al., Genotype-by-environment interaction in genetic mapping of multiple quantitative trait loci. *Theoretical and Applied Genetics,* 91:33-37 (1995)).

In an aspect, this disclosure provides chromosomal intervals comprising QTL associated with LW resistance. In an aspect, the chromosome intervals of this disclosure are characterized by genomic regions including and flanked by: any two of the marker loci selected from the group consisting of SEQ ID NOs: 1 to 3, cl15737_2, and TIDP7101; any two of the marker loci selected from the group consisting of SEQ ID NOs: 47 and 48, gpm748b, and mmp66; any two of the marker loci selected from the group consisting of SEQ ID NOs: 41 and 42, umc1514, and umc1917; any two of the marker loci selected from the group consisting of SEQ ID NO: 43, isu92b, and bnlg100; any two of the marker loci selected from the group consisting of SEQ ID NOs: 8 to 17, 21 to 23, 26 to 38, TIDP5226, and IDP682; marker loci IDP6785 and gpm358; any two of the marker loci selected from the group consisting of SEQ ID NO: 44, TIDP6314, and IDP73; any two of the marker loci selected from the group consisting of SEQ ID NOs: 45 and 46, TIDP4628, and agrr43b; any two of the marker loci selected from the group consisting of SEQ ID NOs: 24 and 25, TIDP6171 and umc49d; any two of the marker loci selected from the group consisting of SEQ ID NOs: 4 to 7, 18 to 20, c142326_1, and IDP498; marker loci phm5359 and npi75a; any two of the marker loci selected from the group consisting of SEQ ID NOs: 49 and 50, ole3, and umc43; marker loci pg11 and gpm674c; any two of the marker loci selected from the group consisting of SEQ ID NO: 39, prp4, and IDP4953; any two of the marker loci selected from the group consisting of SEQ ID NO: 40, gst15; any two of the marker loci selected from the group consisting of SEQ ID NO: 51, umc1380, and bcd386b; marker loci SEQ ID NOs: 257 and 257; and any two of marker loci selected from the group consisting of SEQ ID NOs: 44, and 258 to 264.

This disclosure also provides multiple markers linked to or associated with an LW resistance QTL, for example, the markers having the sequence selected from SEQ ID NOs:1 to 51 and 256 to 264. This disclosure therefore provides plants comprising a nucleic acid molecule selected from the group consisting of SEQ ID NOs:1 to 51 and 256 to 264, fragments thereof, or complements thereof. The present disclosure further provides a plant comprising alleles of the chromosome interval linked to or associated with LW resistance or fragments and complements thereof as well as any plant comprising any combination of two or more LW resistance alleles of marker loci selected from the group consisting of SEQ ID NOs:1 to 51 and 256 to 264. Plants provided by this disclosure can be homozygous or heterozygous for such alleles.

The compositions and methods of the present disclosure can be utilized to guide MAS or breeding corn varieties with a desired complement (set) of allelic forms of chromosome intervals associated with superior agronomic performance (e.g., LW resistance). Any of the provided marker alleles can be introduced into a corn line via introgression, by traditional breeding (or introduced via transformation, or both) to yield a corn plant with superior agronomic performance. The number of alleles associated with LW resistance that can be introduced or be present in a corn plant of the present disclosure ranges from 1 to the number of alleles provided herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this disclosure.

These marker loci can be introgressed into any desired genomic background, germplasm, plant, line, variety, etc., as part of an overall MAS breeding program designed to enhance LW resistance. This disclosure also provides QTL intervals that can be used in MAS to select plants that demonstrate LW resistance. Similarly, QTL intervals can also be used to counter-select plants that are lacking LW resistance. By identifying plants lacking a desired marker locus, plants lacking LW resistance can be identified and selected or eliminated from subsequent crosses.

The present disclosure also extends to a method of making a progeny corn plant and the resulting progeny corn plants. In an aspect, the method comprises crossing a first parent corn plant with a second corn plant and growing the corn plant parent under plant growth conditions to yield corn plant progeny. Methods of crossing and growing a corn plant are well within the ability of those of ordinary skill in the art. Such corn plant progeny can be assayed for alleles associated with LW resistance as provided herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants can be a corn plant of the present disclosure in that it comprises at least one of the allelic forms of the markers of the present disclosure, such that the progeny are capable of inheriting the allele.

By providing the positions in the corn genome of QTL intervals and the associated markers within those intervals, this disclosure also allows one skilled in the art to identify and use other markers within the intervals provided herein or linked to or associated with the intervals provided herein. Having identified such markers, these intervals can be readily identified from public linkage maps.

Closely linked markers flanking the locus of interest that have alleles in linkage disequilibrium (LD) with an LW resistance allele at that locus can be effectively used to select for progeny plants with LW resistance. Thus, the markers described herein, such as those listed in Table 4, as well as other markers genetically linked to or associated with the same chromosome interval, can be used to select for a corn plant or seed with LW resistance. Often, a set of these markers will be used, (e.g., 2 or more, 3 or more, 4 or more, 5 or more) in the flanking regions of the locus. Optionally, as described above, a marker flanking or within the actual locus can also be used. The parents and their progeny can be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice this disclosure is not limited and can be any marker that is genetically linked to or associated with the QTL intervals as described in Table 6, including markers within approximately 20 cM or less of the intervals provided herein. In a further aspect, the present disclosure provides for any marker that is genetically linked to or associated with the QTL intervals as described in Table 6, including markers within approximately 15 cM or less of the intervals provided herein. In a further aspect, the present disclosure provides for any marker that is genetically linked to or associated with the QTL intervals as described in Table 6, including markers within approximately 10 cM or less of the intervals provided herein. In a further aspect, the present disclosure provides for any marker that is genetically linked to or associated with the QTL intervals as described in Table 6, including markers within approximately 5 cM or less of the intervals provided herein. In a further aspect, the present disclosure provides for any marker that is genetically linked to or associated with the QTL intervals as described in Table 6, including markers within approximately 4 cM or less of the intervals provided herein. In a further aspect, the present disclosure provides for any marker that is genetically linked to or associated with the QTL intervals as described in Table 6, including markers within approximately 3 cM or less of the intervals provided herein. In a further aspect, the present disclosure provides for any marker that is genetically linked to or associated with the QTL intervals as described in Table 6, including markers within approximately 2 cM or less of the intervals provided herein. In a further aspect, the present disclosure provides for any marker that is genetically linked to or associated with the QTL intervals as described in Table 6, including markers within approximately 1 cM or less of the intervals provided herein. In a further aspect, the present disclosure provides for any marker that is genetically linked to or associated with the QTL intervals as described in Table 6, including markers within approximately 0.5 cM or less of the intervals provided herein. Examples include, but are not limited to, any marker selected from SEQ ID NOs:1 to 51 and 256 to 264. In an aspect, a marker locus selected from SEQ ID NOs:1 to 51 and 256 to 264 can be amplified using an appropriate pair of primers as indicated in Table 4. Furthermore, since there are many different types of marker detection assays known in the art, it is not intended that the type of marker detection assay used to practice this disclosure be limited in any way.

Marker Assisted Selection (MAS) Breeding

Marker loci and their LW resistance alleles provided herein can be used in MAS breeding of LW resistance. The more tightly linked a marker is with a DNA locus influencing a phenotype (e.g., LW resistance), the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype. However, markers do not need to contain or correspond to causal mutations in order to be effective in MAS. In fact, most MAS breeding only uses markers linked to or associated with a causal mutation.

Developing molecular markers in crop species can increase efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present disclosure provides the means to identify plants that exhibit LW resistance by identifying chromosomal intervals and genetic markers associated with LW resistance.

In general, MAS uses polymorphic markers that have been identified as having a significant likelihood of co-segregation with a desired trait. Such markers are presumed to map near a gene or genes that give the plant its desired phenotype, and are considered indicators for the desired trait.

Identification of plants or germplasm that include a marker locus or marker loci linked to a desired trait or traits provides a basis for performing MAS. Plants that comprise favorable markers or favorable alleles are selected for, while plants that comprise markers or alleles that are negatively correlated with the desired trait can be selected against. Desired markers and/or alleles can be introgressed into plants having a desired (e.g., elite or exotic) genetic background to produce an introgressed plant or germplasm having the desired trait. In an aspect, it is contemplated that a plurality of markers for desired traits are sequentially or simultaneous selected and/or introgressed. The combinations of markers that are selected for in a single plant is not limited, and can include any combination of markers provided herein or any marker linked to the markers provided herein, or any markers located within the QTL intervals defined herein.

In an aspect, a first corn plant or germplasm exhibiting a desired trait (the donor, e.g., an LW resistant corn plant) can be crossed with a second corn plant or germplasm (the recipient; e.g., an elite or exotic corn, depending on characteristics that are desired in the progeny) to create an introgressed corn plant or germplasm as part of a breeding program. In an aspect, the recipient plant can also contain one or more loci associated with one or more desired traits, which can be qualitative or quantitative trait loci. In another aspect, the recipient plant can contain a transgene.

In an aspect, the recipient corn plant or germplasm will typically lack desired traits as compared to the first corn plant or germplasm, while the introgressed corn plant or germplasm will display improved traits as compared to the second plant or germplasm. An introgressed corn plant or germplasm produced by these methods are also a feature of this disclosure.

MAS is a powerful shortcut to select for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than cultivating and observing plants for visible traits.

Genomic Selection

Genomic selection (GS), also known as genome wide selection (GWS), is a form of MAS that estimates all locus, haplotype, and/or marker effects across the entire genome to calculate genomic estimated breeding values (GEBVs). See Nakaya and Isobe, Will genomic selection be a practical method for plant breeding? *Annals of Botany* 110: 1303-1316 (2012); Van Vleck et al., Estimated breeding values for meat characteristics of cross-bred cattle with an animal model. *Journal of Animal Science* 70: 363-371 (1992); and Heffner et al., Genomic selection for crop improvement. *Crop Science* 49: 1-12 (2009). GS utilizes a training phase and a breeding phase. In the training phase, genotypes and phenotypes are analyzed in a subset of a population to generate a GS prediction model that incorporates significant relationships between phenotypes and genotypes. A GS training population must be representative of selection candidates in the breeding program to which GS will be applied. In the breeding phase, genotype data are obtained in a breeding population, then favorable individuals are selected based on GEBVs obtained using the GS prediction model generated during the training phase without the need for phenotypic data.

Larger training populations typically increase the accuracy of GEBV predictions. Increasing the training population to breeding population ratio is helpful for obtaining accurate GEBVs when working with populations having high genetic diversity, small breeding populations, low heritability of traits, or large numbers of QTLs. The number of markers required for GS modeling is determined based on the rate of LD decay across the genome, which must be calculated for each specific population to which GS will be applied. In general, more markers will be necessary with faster raters of LD decay. Ideally, GS comprises at least one marker in LD with each QTL, but in practical terms one of ordinary skill in the art would recognized that this is not necessary.

With genotyping data, favorable individuals from a population can be selected based only on GEBVs. GEBVs are the sum of the estimate of genetic deviation and the weighted sum of estimates of breed effects, which are predicted using phenotypic data. Without being limiting, commonly used statistical models for prediction of GEBVs include best linear unbiased prediction (Henderson, Best linear unbiased estimation and prediction under a selection model. *Biometrics* 31: 423 (1975)) and a Bayesian framework (Gianola and Fernando, Bayesian methods in animal breeding theory. *Journal of Animal Science* 63: 217-244 (1986)).

The compositions and methods of the present disclosure can be utilized for GS or breeding corn varieties with a desired complement (set) of allelic forms of chromosome intervals associated with superior agronomic performance (e.g., LW resistance). In an aspect, a corn plant or seed provided herein can be selected using genomic selection. In another aspect, SEQ ID NOs: 1 to 51 and 256 to 264 can be used in a method comprising genomic selection. In another aspect, a genomic selection method provided herein comprises phenotyping a population of corn plants for LW resistance using the LW rating scale provided in Table 1. In another aspect, a genomic selection method provided herein comprises genotyping a population of corn plants or seeds with at least one of marker loci SEQ ID NOs: 1 to 51 and 256 to 264.

Introgression of LW Resistance QTLs Using MAS

The disclosure provides methods and markers for introgressing one or more LW resistance QTLs provided herein into a new corn variety using MAS.

Multiple methods are available to achieve the introgression. For example, introgression of a desired allele at a specified locus can be transmitted to at least one progeny via a cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

The introgression of one or more desired loci from a donor line into another line is achieved via repeated backcrossing to a recurrent parent accompanied by selection to retain one or more loci from the donor parent. Markers associated with LW resistance are assayed in progeny and those progeny with one or more desired markers are selected for advancement. In another aspect, one or more markers can be assayed in the progeny to select for plants with the genotype of the agronomically elite parent.

It is generally anticipated that trait introgression activities will require more than one generation, wherein progeny are crossed to the recurrent (agronomically elite) parent or selfed. Selections are made based on the presence of one or more markers linked to LW resistance and can also be made based on the recurrent parent genotype, wherein screening is performed on a genetic marker and/or phenotype basis. In another aspect, markers of this disclosure can be used in conjunction with other markers, ideally at least one on each chromosome of the corn genome, to track the introgression of LW resistance into elite germplasm. In another aspect, QTL intervals associated with LW resistance will be useful in conjunction with SNP molecular markers of the present disclosure to combine quantitative and qualitative LW resistance in the same plant. It is within the scope of this disclosure to utilize the methods and compositions for trait integration of LW resistance. It is contemplated by the inventors that the present disclosure will be useful for developing commercial varieties with LW resistance and other agronomically elite phenotypes.

The following are exemplary embodiments of the present disclosure.

Embodiment 1. A method of creating a population of corn plants or seeds, said method comprising:
  a. genotyping a first population of corn plants or seeds at one or more marker loci associated with and within about 20 cM of one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01;
  b. selecting from said first population one or more corn plants or seeds comprising one or more LW resistance alleles of said one or more marker loci; and
  c. producing from said selected one or more corn plants or seeds a second population of corn plants or seeds comprising said one or more LW QTLs.

Embodiment 2. The method of embodiment 1, wherein said one or more marker loci are within about 15 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 3. The method of embodiment 2 or 3, wherein said one or more marker loci are within about 10 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 4. The method of embodiment 1 to 3, wherein said one or more marker loci are within about 5 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 5. The method of embodiment 1 to 4, wherein said one or more marker loci are within about 4 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 6. The method of embodiment 1 to 5, wherein said one or more marker loci are within about 3 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 7. The method of embodiment 1 to 6, wherein said one or more marker loci are within about 2 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 8. The method of embodiment 1 to 7, wherein said one or more marker loci are within about 1 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 9. The method of embodiment 1 to 8, wherein said one or more marker loci are within about 0.5 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 10. The method of embodiment 1 to 9, wherein said one or more marker loci are located in a chromosomal interval flanked by any two of marker loci SEQ ID NOs: 1 to 3.

Embodiment 11. The method of embodiment 1 to 10, wherein said one or more marker loci are located in a chromosomal interval flanked by marker loci SEQ ID NOs: 47 and 48.

Embodiment 12. The method of embodiment 1 to 11, wherein said one or more marker loci are located in a chromosomal interval flanked by marker loci SEQ ID NOs: 41 and 42.

Embodiment 13. The method of embodiment 1 to 12, wherein said one or more marker loci are located in a chromosomal interval flanked by any two of marker loci SEQ ID NOs: 8 to 17, 21 to 23, and 26 to 38.

Embodiment 14. The method of embodiment 1 to 13, wherein said one or more marker loci are located in a chromosomal interval flanked by marker loci SEQ ID NOs: 45 and 46.

Embodiment 15. The method of embodiment 1 to 14, wherein said one or more marker loci are located in a chromosomal interval flanked by marker loci SEQ ID NOs: 24 and 25.

Embodiment 16. The method of embodiment 1 to 15, wherein said one or more marker loci are located in a chromosomal interval flanked by any two of marker loci SEQ ID NOs: 4 to 7 and 18 to 20.

Embodiment 17. The method of embodiment 1 to 16, wherein said one or more marker loci are located in a chromosomal interval flanked by marker loci SEQ ID NOs: 49 and 50.

Embodiment 18. The method of embodiment 1 to 17, wherein said one or more marker loci are located in a chromosomal interval flanked by marker loci SEQ ID NOs: 257 and 257.

Embodiment 19. The method of embodiment 1 to 18, wherein said one or more marker loci are located in a chromosomal interval flanked by any two of marker loci SEQ ID NOs: 44, and 258 to 264.

Embodiment 20. The method of embodiment 1 to 19, wherein said one or more marker loci are within about 20 cM of any one of marker loci selected from the group consisting of SEQ ID NOs:1 to 51 and 256 to 264.

Embodiment 21. The method of embodiment 1 to 20, wherein said one or more marker loci are within about 15 cM of any one of marker loci selected from the group consisting of SEQ ID NOs:1 to 51 and 256 to 264.

Embodiment 22. The method of embodiment 1 to 21, wherein said one or more marker loci are within about 10 cM of any one of marker loci selected from the group consisting of SEQ ID NOs:1 to 51 and 256 to 264.

Embodiment 23. The method of embodiment 1 to 22, wherein said one or more marker loci are within about 5 cM of any one of marker loci selected from the group consisting of SEQ ID NOs:1 to 51 and 256 to 264.

Embodiment 24. The method of embodiment 1 to 23, wherein said one or more marker loci are within about 4 cM of any one of marker loci selected from the group consisting of SEQ ID NOs:1 to 51 and 256 to 264.

Embodiment 25. The method of embodiment 1 to 24, wherein said one or more marker loci are within about 3 cM of any one of marker loci selected from the group consisting of SEQ ID NOs:1 to 51 and 256 to 264.

Embodiment 26. The method of embodiment 1 to 25, wherein said one or more marker loci are within about 2 cM of any one of marker loci selected from the group consisting of SEQ ID NOs:1 to 51 and 256 to 264.

Embodiment 27. The method of embodiment 1 to 26, wherein said one or more marker loci are within about 1 cM of any one of marker loci selected from the group consisting of SEQ ID NOs:1 to 51 and 256 to 264.

Embodiment 28. The method of embodiment 1 to 27, wherein said one or more marker loci are within about 0.5 cM of any one of marker loci selected from the group consisting of SEQ ID NOs:1 to 51 and 256 to 264.

Embodiment 29. The method of embodiment 1 to 28, further comprising: crossing a first corn plant comprising said one or more LW resistance QTLs with a second corn plant of a different genotype to produce said first population of corn plants or seeds.

Embodiment 30. The method of embodiment 1 to 29, wherein said one or more LW resistance QTLs provide mild resistance or resistance to infection by *Harpophora maydis*.

Embodiment 31. The method of embodiment 1 to 30, wherein said second population of corn plants or seeds exhibit reduced dark yellow to brownish macerated pith, brownish-black vascular bundle, or both compared to corn plants or seeds lacking said LW resistance QTL under a similar growth condition.

Embodiment 32. The method of embodiment 1 to 31, wherein said step (a) comprises assaying a single nucleotide polymorphism marker.

Embodiment 33. The method of embodiment 1, wherein said step (a) comprises the use of an oligonucleotide probe.

Embodiment 34. The method of embodiment 1 or 33, wherein said oligonucleotide probe is adjacent to a polymorphic nucleotide position in said marker locus.

Embodiment 35. The method of embodiment 1, wherein said step (a) comprises detecting a haplotype.

Embodiment 36. A method of creating a population of corn plants or seeds, said method comprising:

a. genotyping a first population of corn plants or seeds at one or more marker loci within about 20 cM of any one of marker loci selected from the group consisting of SEQ ID NOs:1 to 51 and 256 to 264 and associated with one or more LW resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01;
b. selecting from said first population one or more corn plants or seeds comprising one or more LW resistance alleles of said one or more marker loci; and
c. producing from said selected one or more corn plants or seeds a second population of corn plants or seeds comprising said one or more LW QTLs.

Embodiment 37. The method of embodiment 36, wherein said one or more marker loci are within about 15 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 38. The method of embodiment 36 or 37, wherein said one or more marker loci are within about 10 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 39. The method of embodiment 36 to 38, wherein said one or more marker loci are within about 5 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 40. The method of embodiment 36 to 39, wherein said one or more marker loci are within about 4 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 41. The method of embodiment 36 to 40, wherein said one or more marker loci are within about 3 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 42. The method of embodiment 36 to 41, wherein said one or more marker loci are within about 2 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 43. The method of embodiment 36 to 42, wherein said one or more marker loci are within about 1 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 44. The method of embodiment 36 to 43, wherein said one or more marker loci are within about 0.5 cM and associated with one or more Late Wilt (LW) resistance quantitative trait loci (QTLs) selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 45. The method of embodiment 36 to 44, further comprising: crossing a first corn plant comprising said one or more LW resistance QTLs with a second corn plant of a different genotype to produce said first population of corn plants or seeds.

Embodiment 46. The method of embodiment 36 to 45, further comprising: crossing a first corn plant comprising said two or more LW resistance QTLs with a second corn plant of a different genotype to produce said first population of corn plants or seeds.

Embodiment 47. The method of embodiment 36 to 46, further comprising: crossing a first corn plant comprising said three or more LW resistance QTLs with a second corn plant of a different genotype to produce said first population of corn plants or seeds.

Embodiment 48. The method of embodiment 36 to 47, further comprising: crossing a first corn plant comprising said four or more LW resistance QTLs with a second corn plant of a different genotype to produce said first population of corn plants or seeds.

Embodiment 49. The method of embodiment 36 to 48, further comprising: crossing a first corn plant comprising said five or more LW resistance QTLs with a second corn plant of a different genotype to produce said first population of corn plants or seeds.

Embodiment 50. The method of embodiment 36 to 49, further comprising: crossing a first corn plant comprising said six or more LW resistance QTLs with a second corn plant of a different genotype to produce said first population of corn plants or seeds.

Embodiment 51. The method of embodiment 36 to 50, wherein said polymorphic locus is in a chromosomal segment flanked by any two of marker loci SEQ ID NOs: 1 to 3.

Embodiment 52. The method of embodiment 36 to 51, wherein said polymorphic locus is in a chromosomal segment flanked by marker loci SEQ ID NOs: 47 and 48.

Embodiment 53. The method of embodiment 36 to 52, wherein said polymorphic locus is in a chromosomal segment flanked by marker loci SEQ ID NOs: 41 and 42.

Embodiment 54. The method of embodiment 36 to 53, wherein said polymorphic locus is in a chromosomal segment flanked by any two of marker loci SEQ ID NOs: 8 to 17, 21 to 23, and 26 to 38.

Embodiment 55. The method of embodiment 36 to 54, wherein said polymorphic locus is in a chromosomal segment flanked by marker loci SEQ ID NOs: 45 and 46.

Embodiment 56. The method of embodiment 36 to 55, wherein said polymorphic locus is in a chromosomal segment flanked by marker loci SEQ ID NOs: 24 and 25.

Embodiment 57. The method of embodiment 36 to 56, wherein said polymorphic locus is in a chromosomal segment flanked by any two of marker loci SEQ ID NOs: 4 to 7 and 18 to 20.

Embodiment 58. The method of embodiment 36 to 57, wherein said polymorphic locus is in a chromosomal segment flanked by marker loci SEQ ID NOs: 49 and 50.

Embodiment 59. The method of embodiment 36 to 58, wherein said polymorphic locus is in a chromosomal segment flanked by marker loci SEQ ID NOs: 257 and 257.

Embodiment 60. The method of embodiment 36 to 59, wherein said polymorphic locus is in a chromosomal segment flanked by any two of marker loci SEQ ID NOs: 44, and 258 to 264.

Embodiment 61. The method of embodiment 36 to 60, further comprising:
  a. crossing said progeny plant with itself or said second plant to produce one or more further progeny plants or seeds; and
  b. selecting a further progeny plant or seed comprising said LW resistance allele.

Embodiment 62. An LW resistant corn plant or seed comprising a combination of two or more introgressed, non-natural LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 63. An LW resistant corn plant or seed comprising a combination of three or more introgressed, non-natural LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 64. An LW resistant corn plant or seed comprising a combination of four or more introgressed, non-natural LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 65. An LW resistant corn plant or seed comprising a combination of five or more introgressed, non-natural LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 66. An LW resistant corn plant or seed comprising a combination of six or more introgressed, non-natural LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 67. The corn plant or seed of embodiments to 62 to 66, wherein seed yield of said corn plant is about 1% or more higher than seed yield of a corn plant without said combination of introgressed LW resistance QTLs under a similar growth condition.

Embodiment 68. The corn plant or seed of embodiments to 62 to 67, wherein said corn plant or seed is in an agronomically elite background.

Embodiment 69. The corn plant or seed of embodiments to 62 to 68, wherein said corn plant or seed is a transgenic hybrid plant or seed.

Embodiment 70. A method for selecting a corn plant or seed with LW resistance, said method comprising:
  a. isolating nucleic acids from a corn plant or seed;
  b. analyzing said nucleic acids to detect a polymorphic marker within 20 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01; and
  c. selecting a corn plant or seed comprising said LW resistance QTL.

Embodiment 71. The method of embodiment 70, wherein said analyzing comprises analyzing said nucleic acids to detect a polymorphic marker within 15 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 72. The method of embodiment 70 or 71, wherein said analyzing comprises analyzing said nucleic acids to detect a polymorphic marker within 10 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 73. The method of embodiment 70 to 72, wherein said analyzing comprises analyzing said nucleic acids to detect a polymorphic marker within 5 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 74. The method of embodiment 70 to 73, wherein said analyzing comprises analyzing said nucleic acids to detect a polymorphic marker within 4 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 75. The method of embodiment 70 to 74, wherein said analyzing comprises analyzing said nucleic acids to detect a polymorphic marker within 3 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 76. The method of embodiment 70 to 75, wherein said analyzing comprises analyzing said nucleic acids to detect a polymorphic marker within 2 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 77. The method of embodiment 70 to 76, wherein said analyzing comprises analyzing said nucleic acids to detect a polymorphic marker within 1 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 78. The method of embodiment 70 to 77, wherein said analyzing comprises analyzing said nucleic acids to detect a polymorphic marker within 0.5 cM of any one of marker loci selected from the group consisting of SEQ ID NOs:1 to 51 and 256 to 264 and associated with an LW resistance QTL selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01.

Embodiment 79. A method comprising providing a set of corn seeds comprising one or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

Embodiment 80. A method comprising providing a set of corn seeds comprising two or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

Embodiment 81. A method comprising providing a set of corn seeds comprising three or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

Embodiment 82. A method comprising providing a set of corn seeds comprising four or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

Embodiment 83. A method comprising providing a set of corn seeds comprising five or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

Embodiment 84. A method comprising providing a set of corn seeds comprising six or more LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01, to a person desirous of planting said set of corn seeds in a field plot.

Embodiment 85. A method of growing a population of corn plants in a field plot, said method comprising planting a population of corn seeds comprising one or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

Embodiment 86. A method of growing a population of corn plants in a field plot, said method comprising planting a population of corn seeds comprising two or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

Embodiment 87. A method of growing a population of corn plants in a field plot, said method comprising planting a population of corn seeds comprising three or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

Embodiment 88. A method of growing a population of corn plants in a field plot, said method comprising planting a population of corn seeds comprising four or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

Embodiment 89. A method of growing a population of corn plants in a field plot, said method comprising planting a population of corn seeds comprising five or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

Embodiment 90. A method of growing a population of corn plants in a field plot, said method comprising planting a population of corn seeds comprising six or more introgressed LW resistance QTLs selected from the group consisting of LW resistance QTLs LW_1.01, LW_1.02, LW_1.03, LW_1.04, LW_2.01, LW_3.01, LW_3.02, LW_3.03, LW_4.01, LW_4.02, LW_5.01, LW_5.02, LW_6.01, LW_7.01, LW_8.01, and LW_10.01 in said field plot.

EXAMPLES

Example 1

Phenotyping Late Wilt Disease Symptoms

In a first study design, a standardized inoculation assay is developed to assess late wilt (LW) resistance in corn. In summary, stem pieces of maize plants infected with late wilt are surface-sterilized with 4% sodium hydrochloride solution followed by thorough washing with distilled water. Surface-sterilized infected stem fiber tissues are then placed on 39% Potato Dextrose Agar (PDA) medium. The plates are incubated for five days in a Biochemical Oxygen Demad (BOD) incubator for the development of pathogen (*Harpophora maydis*) colonies. The colonization of *H. maydis* is confirmed based on morphological and fruiting body characteristics (Samra et al., 1963). The pathogen mycelia is subsequently transferred to 24% Potato Dextrose Broth (PDB) aseptically and incubated for 15 days in PDB for the growth of the pathogen. PDB containing a mycelia mat of pathogen is grounded and the spore suspension is used for inoculating the healthy maize inbred lines at the second internode from the base. For phenotyping, the stalks of the inbred lines are split open at maturity for disease phenotyping. Disease severity and intensity is measured using a 1-9 rating scale based on internode discoloration and its movement to adjacent internodes (Table 1).

TABLE 1

Rating Scale of LW infection phenotypes.

| Scale | Description |
|---|---|
| 1 | Indicates <25% of inoculated internode discolored |
| 2 | 26-50% of inoculated internode discolored |
| 3 | 51-75% of inoculated internode discolored or 26-50% discoloration with high disintegration of the stalk |
| 4 | 76-100% of inoculated internode discolored or 51-75% discoloration with high disintegration of the stalk |
| 5 | Discoloration of less than 50% of adjacent internodes or 76-100% discoloration of inoculated internode with high disintegration of the stalk |
| 6 | Discoloration of more than 50% of adjacent internodes or complete discoloration of the inoculated internode with high disintegration and moderate fibrousness |
| 7 | Discoloration of more than two internodes or <2 internodes with high disintegration and fibrousness of the stalk |
| 8 | Discoloration of more than three internodes or <3 internodes with high disintegration and complete fibrousness of the stalk |
| 9 | Discoloration of more than 3 internodes with complete fibrousness of the stalk and plants killed immaturely |

In a second study design, maize plants are planted under natural disease pressure without artificial inoculation. Under natural disease pressure, infected plants die after wilting while un-infected plants remain green. For disease rating, the percentage of dead plants among the total number of plants per plot was calculated at 50%-80% of milk line.

Example 2

Genome-Wide Association Study (GWAS) of LW Resistance

A genome-wide association (GWAS) study is conducted to identify haplotype windows associated with LW resistance. In this study, 398 lines are measured for LW resistance following the phenotyping assay and disease scale from Example 1. Genotype data are also collected for these lines. The least absolute shrinkage and selection operator (LASSO) (Li, 2012) and bootstrapping (Visscher, 1996) methods are used in the GWAS study. Table 2 lists the top haplotype windows associated with LW resistance identified by GWAS. Each row provides haplotype window ID, chromosome location of the haplotype window, start and end position of the haplotype window (stPos and endPos, respectively), phenotypic variance ($R^2$) explained by the haplotype window, estimated effect of the haplotype window on LW resistance, standard error, F-statistic, p-value corresponding to the F-statistic. Haplotype windows h083h0003-h077h0002 that cover the interval of 114.8-142.4 cM on chromosome 8 was identified to be associated with LW resistance and contribute to 23% of phenotypic variation. Haplotype window c080h0006 that covers the interval of 140.3-142.3 cM and haplotype windows c100h0002-c100h0017 that cover the interval of 172.6-173.9 cM on chromosome 3 were also identified to be associated with LW resistance.

TABLE 2

Selected haplotype windows identified by GWAS to be associated with LW resistance. Effects are shown by estimates based on the first study design.

| HapID | Chr | stPos | endPos | $R^2$ | Effect | StdErr | FValue | ProbF |
|---|---|---|---|---|---|---|---|---|
| h083h0003 | 8 | 140.1 | 142.4 | 0.072 | −0.35 | 0.09 | 30.50 | 0.0000 |
| h079h0002 | 8 | 131.7 | 133.4 | 0.033 | 0.56 | 0.21 | 15.71 | 0.0001 |
| h079h0006 | 8 | 131.7 | 133.4 | 0.035 | −0.55 | 0.17 | 15.63 | 0.0001 |
| h079h0014 | 8 | 131.7 | 133.4 | 0.031 | 0.84 | 0.38 | 13.95 | 0.0002 |
| h083h0006 | 8 | 140.1 | 142.4 | 0.021 | −0.66 | 0.22 | 10.28 | 0.0015 |
| h072h0010 | 8 | 114.8 | 120 | 0.017 | −0.49 | 0.16 | 8.39 | 0.0040 |
| h077h0009 | 8 | 129.3 | 130.5 | 0.011 | −0.33 | 0.16 | 5.37 | 0.0210 |

TABLE 2-continued Selected haplotype windows identified by GWAS to be associated with LW resistance. Effects are shown by estimates based on the first study design.

| HapID | Chr | stPos | endPos | $R^2$ | Effect | StdErr | FValue | ProbF |
|---|---|---|---|---|---|---|---|---|
| h077h0002 | 8 | 129.3 | 130.5 | 0.008 | 0.43 | 0.21 | 3.95 | 0.0475 |
|  |  |  |  |  | 0.230 |  |  |  |
| c080h0006 | 3 | 140.3 | 142.3 | 0.038 | −0.42 | 0.15 | 15.63 | 0.0001 |
| c100h0002 | 3 | 172.6 | 173.9 | 0.021 | 0.73 | 0.28 | 8.75 | 0.0033 |
| c100h0068 | 3 | 172.6 | 173.9 | 0.019 | 0.53 | 0.37 | 3.46 | 0.0636 |
| c100h0017 | 3 | 172.6 | 173.9 | 0.007 | −0.57 | 0.22 | 3.13 | 0.0774 |
|  |  |  |  |  | 0.085 |  |  |  |

Example 3

Construction of Biparental Mapping Populations for Identifying LW Resistance QTLs Four LW resistance source lines are used to produce biparental mapping populations to investigate the genetic basis of LW resistance in corn. Ten mapping populations (A to G, Table 3A and Table 3B) are constructed. Plant phenotyping is performed according to Example 1. Plants from all mapping populations are genotyped using SNP markers that collectively span each chromosome in the maize genome. Marker-trait association studies are performed to identify LW disease resistance QTLs and their associated markers using composite interval mapping (CIM) and single marker analysis (SMA).

TABLE 3A

Bi-parental mapping populations A to E and H to J.

| Mapping Population | Cross | Resistant Line | Susceptible Line | Population Type | Population size |
|---|---|---|---|---|---|
| A | CV134767/CV131061 | CV131061 | CV134767 | F3 | 342 |
| B | CV131061/CV124239 | CV131061 | CV124239 | F3 | 357 |
| C | CV136745/CV131061 | CV131061 | CV136745 | F3 | 253 |
| D | CV137520/CV806292 | CV806292 | CV137520 | DH | 113 |
| E | CV137520/CV137694 | CV137694 | CV137520 | DH | 149 |
| H | CV566265/CV137520 | CV566265 | CV137520 | DH | 170 |
| I | CV137520/CV569224 | CV569224 | CV137520 | DH | 166 |
| J | CV126318/CV137520 | CV126318 | CV137520 | DH | 146 |

TABLE 3B

Bi-parental mapping populations F and G.

| Mapping Population | Cross | Resistant Line | Susceptible Line | Population Type | Population size |
|---|---|---|---|---|---|
| F | CV138811/CV143587 | CV138811 | CV143587 | F3 | 211 |
| G | CV138811/CV136745 | CV138811 | CV136745 | F3 | 199 |

Example 4

Identification of Molecular Markers Associated with LW Disease Resistance Via Single-Marker Analysis (SMA)

Single-marker analysis (SMA) is performed to identify markers associated with LW resistance using the genotypic data from Example 3. For each marker, the thresholds (p-value) for SMA are based on 10,000 random permutation tests (Churchill and Doerg, *Genetics*, 138(3):963-71 (1994)).

In total, 60 SNP markers are identified to be linked to LW disease resistance (Table 4). The primer sequences for amplifying exemplary SNP marker loci linked to LW disease resistance and the probes used to genotype the corresponding SNP sequences are provided in Table 4. In an illustrative example, SNP marker SEQ ID NO: 1 can be amplified using the primers described in Table 4 as SEQ ID NO: 52 (forward primer) and SEQ ID NO: 103 (reverse primer), and detected with probes indicated as SEQ ID NO: 154 (Probe 1) and SEQ ID NO: 205 (Probe 2). One of skill in the art will recognize that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, the disclosure is not limited to the primers, probes, or marker sequences specifically recited herein.

TABLE 4

Exemplary primers and probes used for genotyping representative SNP markers associated with LW resistance

| SEQ ID NO. | SNP Position | SEQ ID NO. | | | |
|---|---|---|---|---|---|
|  |  | Fwd Primer | Rev Primer | Probe 1 | Probe 2 |
| 1 | 287 | 52 | 103 | 154 | 205 |
| 2 | 163 | 53 | 104 | 155 | 206 |
| 3 | 137 | 54 | 105 | 156 | 207 |
| 4 | 394 | 55 | 106 | 157 | 208 |
| 5 | 101 | 56 | 107 | 158 | 209 |
| 6 | 115 | 57 | 108 | 159 | 210 |
| 7 | 2239 | 58 | 109 | 160 | 211 |
| 8 | 244 | 59 | 110 | 161 | 212 |
| 9 | 270 | 60 | 111 | 162 | 213 |
| 10 | 430 | 61 | 112 | 163 | 214 |
| 11 | 269 | 62 | 113 | 164 | 215 |
| 12 | 61 | 63 | 114 | 165 | 216 |
| 13 | 61 | 64 | 115 | 166 | 217 |
| 14 | 61 | 65 | 116 | 167 | 218 |
| 15 | 138 | 66 | 117 | 168 | 219 |
| 16 | 61 | 67 | 118 | 169 | 220 |
| 17 | 101 | 68 | 119 | 170 | 221 |
| 18 | 409 | 69 | 120 | 171 | 222 |
| 19 | 215 | 70 | 121 | 172 | 223 |
| 20 | 101 | 71 | 122 | 173 | 224 |
| 21 | 148 | 72 | 123 | 174 | 225 |
| 22 | 101 | 73 | 124 | 175 | 226 |
| 23 | 101 | 74 | 125 | 176 | 227 |

TABLE 4-continued

Exemplary primers and probes used for genotyping representative SNP markers associated with LW resistance

| SEQ ID NO. | SNP Position | SEQ ID NO. | | | |
|---|---|---|---|---|---|
| | | Fwd Primer | Rev Primer | Probe 1 | Probe 2 |
| 24 | 283 | 75 | 126 | 177 | 228 |
| 25 | 189 | 76 | 127 | 178 | 229 |
| 26 | 674 | 77 | 128 | 179 | 230 |
| 27 | 298 | 78 | 129 | 180 | 231 |
| 28 | 483 | 79 | 130 | 181 | 232 |
| 29 | 44 | 80 | 131 | 182 | 233 |
| 30 | 101 | 81 | 132 | 183 | 234 |
| 31 | 90 | 82 | 133 | 184 | 235 |
| 32 | 871 | 83 | 134 | 185 | 236 |
| 33 | 460 | 84 | 135 | 186 | 237 |
| 34 | 252 | 85 | 136 | 187 | 238 |
| 35 | 225 | 86 | 137 | 188 | 239 |
| 36 | 232 | 87 | 138 | 189 | 240 |
| 37 | 321 | 88 | 139 | 190 | 241 |
| 38 | 101 | 89 | 140 | 191 | 242 |
| 39 | 101 | 90 | 141 | 192 | 243 |
| 40 | 574 | 91 | 142 | 193 | 244 |
| 41 | 230 | 92 | 143 | 194 | 245 |
| 42 | 73 | 93 | 144 | 195 | 246 |
| 43 | 357 | 94 | 145 | 196 | 247 |
| 44 | 46 | 95 | 146 | 197 | 248 |
| 45 | 270 | 96 | 147 | 198 | 249 |
| 46 | 1440 | 97 | 148 | 199 | 250 |
| 47 | 339 | 98 | 149 | 200 | 251 |
| 48 | 358 | 99 | 150 | 201 | 252 |
| 49 | 70 | 100 | 151 | 202 | 253 |
| 50 | 349 | 101 | 152 | 203 | 254 |
| 51 | 309 | 102 | 153 | 204 | 255 |
| 256 | 350 | 265 | 274 | 283 | 292 |
| 257 | 456 | 266 | 275 | 284 | 293 |
| 258 | 101 | 267 | 276 | 285 | 294 |
| 259 | 73 | 268 | 277 | 286 | 295 |
| 260 | 999 | 269 | 278 | 287 | 296 |
| 261 | 106 | 270 | 279 | 288 | 297 |
| 262 | 101 | 271 | 280 | 289 | 298 |
| 263 | 1946 | 272 | 281 | 290 | 299 |
| 264 | 101 | 273 | 282 | 291 | 300 |

The effect on LW rating score for each marker linked to LW disease resistance is also estimated and shown in Table 5A and Table 5B. Further provided are the SEQ ID NO of the marker, chromosome position, marker position on Monsanto's internal consensus genetic map, corresponding marker position on the Neighbors 2008 maize genetic map (publicly available at the MaizeGDB website, maizegdb.org/data_center/map), genetic source of favorable allele, exemplary resistant allele, exemplary susceptible allele, the estimated effect that the marker polymorphism has on the LW rating score, and p-value based on 10,000 random permutation tests. For example, SEQ ID NO: 11 was associated with 20.9% less dead plants under natural disease pressure by one copy of the resistant allele. SEQ ID NO: 34 was associated with a reduction of 0.678 in 1-9 LW rating scale under inoculation by one copy of the resistant allele. However, one of skill in the art recognizes that a "resistant" allele at one locus can be a "susceptible" allele in a different genetic background. Thus, this disclosure is not limited to the "resistant" and "susceptible" alleles exemplified herein.

In Table 5A and Table 5B, "IcM" refers to the map units of the IBM2 2008 Neighbors Genetic Map, which was generated with an intermated recombinant inbred population (syn 4) that resulted in approximately a four-fold increase in the number of meioses as compared to the typical recombination experiment that is used to generate cM distances (Lee et al., 2002, *Plant Mol Biol* 48:453 and the Maize Genetics and Genomics Database). "cM" refers to the classical definition of a centimorgan wherein one cM is equal to a 1% chance that a trait at one genetic locus will be separated from a trait at another locus due to crossing over in a single generation (meaning the traits co-segregate 99% of the time during meiosis), and this definition is used herein to delineate map locations pertaining to this invention.

TABLE 5A

Estimate effects of markers linked to LW disease resistance from mapping populations A to E, and H to J by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability | Mapping Population |
|---|---|---|---|---|---|---|---|---|---|
| 1 | 1 | 36.8 | 109.9 | CV806292 | T | C | 0.1* | 0.001 | D |
| 2 | 1 | 42.6 | 124.2 | CV806292 | T | C | 0.092* | 0.001 | D |
| 3 | 1 | 47.5 | 139.8 | CV806292 | C | T | 0.084* | 0.001 | D |
| 4 | 4 | 155.0 | 531.5 | CV806292 | C | A | 0.071* | 0.001 | D |
| 5 | 4 | 162.0 | 571.6 | CV806292 | A | C | 0.08* | 0.001 | D |
| 6 | 4 | 165.8 | 579.6 | CV806292 | T | A | 0.076* | 0.001 | D |
| 7 | 4 | 171.9 | 594.0 | CV806292 | T | G | 0.036* | 0.001 | D |
| 8 | 2 | 34.2 | 90.3 | CV137694 | T | C | 0.208* | 0.001 | E |
| 9 | 2 | 34.5 | 90.7 | CV137694 | G | A | 0.208* | 0.001 | E |
| 10 | 2 | 35.2 | 91.7 | CV137694 | A | C | 0.208* | 0.001 | E |
| 11 | 2 | 35.7 | 92.4 | CV137694 | C | T | 0.209* | 0.001 | E |
| 12 | 2 | 36.2 | 93.2 | CV137694 | G | A | 0.207* | 0.001 | E |
| 13 | 2 | 36.3 | 93.3 | CV137694 | A | G | 0.207* | 0.001 | E |
| 14 | 2 | 38.9 | 105.0 | CV137694 | T | C | 0.202* | 0.001 | E |
| 15 | 2 | 46.3 | 136.2 | CV137694 | T | A | 0.213* | 0.001 | E |
| 16 | 2 | 47.1 | 139.7 | CV137694 | C | G | 0.213* | 0.001 | E |
| 17 | 2 | 50.7 | 149.2 | CV137694 | A | G | 0.206* | 0.001 | E |
| 18 | 4 | 149.9 | 514.4 | CV131061 | A | T | 0.47 | 0.001 | A |
| 4 | 4 | 155.0 | 531.5 | CV131061 | C | A | 0.495 | 0.001 | A |
| 19 | 4 | 162.8 | 573.4 | CV131061 | G | A | 0.532 | 0.001 | A |
| 20 | 4 | 168.4 | 586.4 | CV131061 | A | G | 0.509 | 0.001 | A |
| 21 | 2 | 34.5 | 90.7 | CV131061 | C | T | 0.232 | 0.001 | B |

TABLE 5A-continued

Estimate effects of markers linked to LW disease resistance from mapping populations A to E, and H to J by SMA.

| SEQ ID NO. | Chromosome | MON Map (cM) | IBM2008 Map (IcM) | Genetic Source of Favorable Allele | Exemplary Resistant Allele | Exemplary Susceptible Allele | Single Allele Effect | Permutation Testing Probability | Mapping Population |
|---|---|---|---|---|---|---|---|---|---|
| 22 | 2 | 43.8 | 125.5 | CV131061 | C | G | 0.317 | 0.001 | B |
| 23 | 2 | 54.2 | 161.8 | CV131061 | C | T | 0.25 | 0.001 | B |
| 24 | 4 | 65.5 | 156.0 | CV131061 | T | A | 0.338 | 0.001 | B |
| 25 | 4 | 77.4 | 217.1 | CV131061 | G | C | 0.332 | 0.001 | B |
| 26 | 2 | 32.2 | 82.8 | CV131061 | A | G | 0.529 | 0.001 | C |
| 27 | 2 | 40.2 | 110.0 | CV131061 | G | A | 0.586 | 0.001 | C |
| 28 | 2 | 54.6 | 162.9 | CV131061 | G | A | 0.573 | 0.001 | C |
| 29 | 2 | 33.6 | 88.0 | CV131061 | A | G | 0.502 | 0.001 | B + C |
| 21 | 2 | 34.5 | 90.7 | CV131061 | C | T | 0.628 | 0.001 | B + C |
| 9 | 2 | 34.5 | 90.7 | CV131061 | G | A | 0.497 | 0.001 | B + C |
| 30 | 2 | 34.5 | 90.7 | CV131061 | C | T | 0.532 | 0.001 | B + C |
| 10 | 2 | 35.2 | 91.7 | CV131061 | A | C | 0.397 | 0.001 | B + C |
| 31 | 2 | 35.4 | 92.0 | CV131061 | T | C | 0.494 | 0.001 | B + C |
| 32 | 2 | 35.4 | 92.0 | CV131061 | G | T | 0.484 | 0.001 | B + C |
| 11 | 2 | 35.7 | 92.4 | CV131061 | C | T | 0.632 | 0.001 | B + C |
| 33 | 2 | 36.5 | 94.2 | CV131061 | G | T | 0.505 | 0.001 | B + C |
| 34 | 2 | 37.4 | 98.0 | CV131061 | A | G | 0.678 | 0.001 | B + C |
| 35 | 2 | 39.4 | 106.6 | CV131061 | A | C | 0.407 | 0.001 | B + C |
| 27 | 2 | 40.2 | 110.0 | CV131061 | G | A | 0.718 | 0.001 | B + C |
| 22 | 2 | 43.8 | 125.5 | CV131061 | C | G | 0.746 | 0.001 | B + C |
| 36 | 2 | 47.8 | 142.7 | CV131061 | T | C | 0.57 | 0.001 | B + C |
| 17 | 2 | 50.7 | 149.2 | CV131061 | A | G | 0.547 | 0.001 | B + C |
| 37 | 2 | 52.3 | 156.9 | CV131061 | A | C | 0.404 | 0.001 | B + C |
| 23 | 2 | 54.2 | 161.8 | CV131061 | C | T | 0.409 | 0.001 | B + C |
| 28 | 2 | 54.6 | 162.9 | CV131061 | G | A | 0.52 | 0.001 | B + C |
| 38 | 2 | 54.9 | 163.7 | CV131061 | A | G | 0.407 | 0.001 | B + C |
| 39 | 7 | 45.3 | 95.5 | CV131061 | A | C | 0.445 | 0.001 | C |
| 40 | 8 | 112.1 | 394.3 | CV124239 | A | G | 0.315 | 0.001 | B |
| 256 | 3 | 87.9 | 292.7 | CV566265__CV569224__CV126318 | G | A | 0.173* | 0.001 | H + I + J |
| 257 | 3 | 89.9 | 305.6 | CV566265__CV569224__CV126318 | A | G | 0.181* | 0.001 | H + I + J |
| 44 | 3 | 110.9 | 382.6 | CV566265__CV569224__CV126318 | A | G | 0.289* | 0.001 | H + I + J |
| 258 | 3 | 111.8 | 388.9 | CV566265__CV569224__CV126318 | C | G | 0.283* | 0.001 | H + I + J |
| 259 | 3 | 114.9 | 398.4 | CV566265__CV569224__CV126318 | C | T | 0.229* | 0.001 | H + I + J |
| 260 | 3 | 115.9 | 401.2 | CV566265__CV569224__CV126318 | T | C | 0.220* | 0.001 | H + I + J |
| 261 | 3 | 116.5 |  | CV566265__CV569224__CV126318 | C | T | 0.165* | 0.001 | H + I + J |
| 262 | 3 | 117.5 | 406.2 | CV566265__CV569224__CV126318 | T | C | 0.211* | 0.001 | H + I + J |
| 263 | 3 | 119.4 | 412.9 | CV566265__CV569224__CV126318 | G | A | 0.198* | 0.001 | H + I + J |
| 264 | 3 | 119.9 | 414.1 | CV566265__CV569224__CV126318 | C | 1 | 0.149* | 0.001 | H + I + J | cM = centimorgans,
IcM = map units of the IBM2 2008 Neighbors Genetic Map (Asterisks indicate single allele effects shown by percentage changes under natural disease pressure based on the second study design, e.g., 0.1 means 10%. The other single allele effects are shown on Table 1's 1-9 scale with inoculation based on the first study design, e.g., 0.47 means a reduction of 0.47 out of 1-9 scale.).

TABLE 5B

Estimate effects of markers linked to LW disease resistance from mapping populations F and G by SMA.

| SEQ ID NO. | Chromosome | MON Map (cM) | IBM2008 Map (IcM) | Genetic Source of Favorable Allele | Exemplary Resistant Allele | Exemplary Susceptible Allele | Additive Effect | Dominant Effect | P-value | Mapping Population |
|---|---|---|---|---|---|---|---|---|---|---|
| 41 | 1 | 103.3 | 362.2 | CV138811 | T | A | 0.5393 | 0.0828 | 0.0000754 | F |
| 42 | 1 | 92.7 | 285.8 | CV138811 | A | T | 0.4007 | −0.1874 | 0.005199 | F |
| 43 | 1 | 219.8 | 870.9 | CV138811 | G | A | 0.4284 | 0.1135 | 0.002641 | F |
| 44 | 3 | 110.9 | 382.6 | CV138811 | G | A | −0.4231 | 0.1437 | 0.003938 | F |
| 45 | 3 | 204.5 | 777.7 | CV138811 | A | C | 0.4648 | −0.2388 | 0.000432 | F |
| 46 | 3 | 212.4 | 806.7 | CV138811 | C | G | 0.5833 | −0.3607 | 0.0000241 | F |
| 47 | 1 | 72.4 | 204.3 | CV138811 | T | G | 0.388 | 0.1848 | 0.001373 | G |
| 48 | 1 | 79.9 | 224.4 | CV138811 | A | G | 0.4216 | 0.1568 | 0.000339 | G |
| 49 | 5 | 51.6 | 190.2 | CV138811 | C | T | 0.4895 | 0.0441 | 0.000232 | G |
| 50 | 5 | 76 | 266.3 | CV138811 | C | T | 0.5617 | −0.003 | 0.0000148 | G |
| 51 | 10 | 75.3 | 362.3 | CV138811 | C | G | 0.2022 | −0.4568 | 0.003102 | G | cM = centimorgans,
IcM = map units of the IBM2 2008 Neighbors Genetic Map. Effects are estimated based on the first study design.

Example 5

Identification of LW Disease Resistance QTLs Via Composite Interval Mapping

A composite interval mapping (CIM) approach is taken to identify LW resistance QTL intervals based on the phenotyping and genotyping data collected in Example 3. For each marker, the thresholds of likelihood ratio between full and null models for CIM are based on 1000 random permutation tests (Churchill and Doerg, Genetics, 138(3):963-71 (1994)). The composite interval mapping (CIM) analysis reveals several strong QTLs associated with LW resistance. The QTLs are confirmed in multiple genetic backgrounds and summarized in Table 6A and Table 6B.

In Table 6A and Table 6B, genetic positions are represented in cM with position zero being the first (most distal) marker known at the beginning of the chromosome on Monsanto's internal consensus genetic map. Each row of Table 6A provides mapping population ID, number of SNP markers genotyped, resistant parent, chromosome position, the peak of the likelihood ratio corresponding to LW resistance, left and right flanking positions, p-value, additive effect, and the phenotypic variance ($R^2$) of individual QTL. Each row of Table 6B provides mapping population ID, number of SNP markers genotyped, resistant parent, chromosome position, the peak of the Likelihood ratio corresponding to LW resistance, left and right flanking positions of QTL intervals, LOD score, additive effect, dominant effect and the percentage of total variance explained (PVE %). The cut-off of LOD score is 2.5.

In summary, the following QTLs are identified and designated as LW_1.01; LW_1.02; LW_1.03; LW_1.04; LW_2.01; LW_3.01; LW_3.02; LW_3.03; LW_4.01; LW_4.02; LW_5.01; LW_5.02; LW_6.01; LW_7.01; LW_8.01; LW_10.01 (Table 7).

In Table 7, "IcM" refers to the map units of the IBM2 2008 Neighbors Genetic Map, which was generated with an intermated recombinant inbred population (syn 4) that resulted in approximately a four-fold increase in the number of meiosies as compared to the typical recombination experiment that is used to generate centiMorgan (cM) distances (Lee et al., 2002, Plant Mol Biol 48:453 and the Maize Genetics and Genomics Database). "cM" refers to the classical definition of a centimorgan wherein one cM is equal to a 1% chance that a trait at one genetic locus will be separated from a trait at another locus due to crossing over in a single generation (meaning the traits cosegregate 99% of the time during meiosis), and this definition is used herein to delineate map locations pertaining to this invention.

TABLE 6A

CIM results from all mapping populations.

| Mapping population | Number of Markers Genotyped | Resistant Parent | Chr | Peak | Left Flank | Right Flank | p-value* | Additive Effect | Individual QTL $R^2$ |
|---|---|---|---|---|---|---|---|---|---|
| A | 161 | CV131061 | 4 | 161 | 155.2 | 168.9 | 0.01 | 0.53 | 0.13 |
| B | 153 | CV131061 | 2 | 43.8 | 37.5 | 51.8 | 0.01 | 0.28 | 0.06 |
|   |   |   | 4 | 71.5 | 60.5 | 76.5 | 0.01 | 0.38 | 0.12 |
|   |   |   | 8 | 115.11 | 100.5 | 118.1 | 0.01 | −0.37 | 0.09 |
| C | 159 | CV131061 | 2 | 46.2 | 33.2 | 54.2 | 0.01 | 0.66 | 0.16 |
|   |   |   | 3 | 95.8 | 85.4 | 105.2 | 0.01 | 0.4 | 0.08 |
|   |   |   | 7 | 35.2 | 25.9 | 45.3 | 0.01 | 0.66 | 0.19 |
| D | 156 | CV806292 | 1 | 40.81 | 34.8 | 47.5 | 0.01 | 0.0815 | 0.12 |
|   |   |   | 4 | 161.01 | 152.5 | 166.8 | 0.01 | 0.0844 | 0.13 |
| E | 171 | CV137694 | 2 | 45.9 | 35.6 | 46.3 | 0.01 | 0.185 | 0.29 |
| H | 144 | CV566265 | 3 | 105.1 | 89.6 | 119.8 | 0.01 | −0.356 | 0.79 |
| I | 144 | CV569224 | 3 | 108.9 | 90 | 119.3 | 0.01 | −0.212 | 0.43 |
| J | 142 | CV126318 | 3 | 102.8 | 86.8 | 117.8 | 0.01 | −0.362 | 0.78 |

*p-value is based on 1,000 permutation tests;
†Based on Monsanto's internal consensus genetic map. For populations A to C, additive effects are shown by estimates based on the first study design (scale of 1-9). Additive effects in populations D and E, and H to J are estimated based on the second study design.

TABLE 6B

CIM results from all mapping populations.

| Mapping population | Number of Markers Genotyped | Resistant Parent | Chr | Peak | Left Flank | Right Flank | LOD | Additive Effects | Dominant | PVE (%) |
|---|---|---|---|---|---|---|---|---|---|---|
| F | 126 | CV138811 | 1 | 103.20 | 92.7 | 103.3 | 4.81 | 0.5074 | 0.1266 | 7.26 |
|   |   |   | 1 | 220.00 | 219.8 | 226.8 | 4.01 | 0.4269 | 0.1720 | 6.06 |
|   |   |   | 3 | 113.80 | 110.9 | 118.3 | 3.86 | −0.4803 | 0.1995 | 6.65 |
|   |   |   | 3 | 210.80 | 204.5 | 212.4 | 8.60 | 0.6679 | −0.5374 | 14.62 |
|   |   |   | 5 | 10.30 | 10.3 | 23.2 | 3.20 | −0.0774 | 0.5374 | 4.73 |
| G | 107 | CV138811 | 1 | 79.10 | 72.4 | 79.9 | 3.78 | 0.4225 | 0.1993 | 7.60 |
|   |   |   | 5 | 68.60 | 51.6 | 76 | 5.44 | 0.5873 | 0.0347 | 12.54 |
|   |   |   | 6 | 39.70 | 34.5 | 43.4 | 2.74 | 0.4163 | 0.1068 | 6.02 |
|   |   |   | 10 | 37.20 | 5.2 | 75.3 | 7.49 | 0.7505 | −1.2005 | 49.08 |

†Based on Monsanto's internal consensus genetic map. Additive effects are shown by estimates based on the first study design.

TABLE 7

Summary of LW QTLs.

| Chromosome | QTL interval (cM) | IBM2008 Map (IcM) | Flanking public markers Left | Right | QTL Designation | Associated SNP Marker(s) (SEQ ID NO) |
|---|---|---|---|---|---|---|
| 1 | 34.8-47.5 | 104.2-139.8 | cl15737__-2 | TIDP7101 | LW__1.01 | 1 to 3 |
| 1 | 72.4-79.9 | 204.4-224.4 | gpm748b | mmp66 | LW__1.02 | 47, 48 |
| 1 | 92.7-103.3 | 285.8-374.8 | umc1514 | umc1917 | LW__1.03 | 41, 42 |
| 1 | 219.8-226.8 | 871.3-908.1 | isu92b | bnlg100 | LW__1.04 | 43 |
| 2 | 33.2-54.2 | 86.2-161.8 | TIDP5226 | IDP682 | LW__2.01 | 8 to 17, 21 to 23, 26 to 38 |
| 3 | 85.4-105.2 | 260.3-361.1 | IDP6785 | gpm358 | LW__3.01 | 256, 257 |
| 3 | 110.9-119.9 | 381.8-409.8 | TIDP6314 | IDP73 | LW__3.02 | 44, 258 to 264 |
| 3 | 204.5-212.4 | 777.5-806.7 | TIDP4628 | agrr43b | LW__3.03 | 45, 46 |
| 4 | 60.5-76.5 | 147.8-214 | TIDP6171 | umc49d | LW__4.01 | 24, 25 |
| 4 | 152.5-168.9 | 525.1-587.4 | cl42326__1 | IDP498 | LW__4.02 | 4 to 7, 18 to 20 |
| 5 | 10.3-23.2 | 53.3-99 | phm5359 | npi75a | LW__5.01 | |
| 5 | 51.6-76 | 190-266.3 | ole3 | umc43 | LW__5.02 | 49, 50 |
| 6 | 34.5-43.4 | 189.9-214.3 | pg11 | gpm674c | LW__6.01 | |
| 7 | 25.9-45.3 | 53-95.5 | prp4 | IDP4953 | LW__7.01 | 39 |
| 8 | 100.5-118.1 | 352-409.2 | gst15 | gpm84 | LW__8.01 | 40 |
| 10 | 5.2-75.3 | 16.6-262.3 | umc1380 | bcd386b | LW__10.01 | 51 | cM = centimorgans;
IcM = map units of the IBM2 2008 Neighbors Genetic Map.

Example 6

Fine-Mapping by Joint Linkage Mapping (JLM)

Mapping populations B and are merged for joint linkage mapping using the least absolute shrinkage and selection operator (LASSO) model. Mapping populations H, I and J are merged for joint linkage mapping using the least absolute shrinkage and selection operator (LASSO) model. 304 SNP markers are genotyped. 95% best markers based on bootstrapping probability are identified within 40.2-47.8 cM on chromosome 2 and 33.7-51.3 cM on chromosome 7, and 103.5-109.2 cM on Chromosome 3 of Monsanto's internal consensus genetic map (Table 8). Table 8 provides chromosome position, QTL peak position, QTL interval where left and right flanking positions are shown, p-value, additive effect, and phenotypic variance ($R^2$) of individual QTL.

TABLE 8

Fine-mapping of LW QTLs by JLM. Additive effects are shown by estimates. (Asterisks indicate additive effects shown by percentage changes under natural disease pressure based on the second study design, e.g., 0.1 means 10%. The other additive effects are shown on Table 1's 1-9 scale with inoculation based on the first study design, e.g., 0.47 means a reduction of 0.47 out of 1-9 scale.)

| Chr | QTL Positions (cM) QTL peak | Left | Right | p-value | Additive Effects | QTL $R^2$ |
|---|---|---|---|---|---|---|
| 2 | 45.8 | 40.2 | 47.8 | 0.01 | 0.65 | 0.17 |
| 3 | 105.1 | 103.5 | 109.2 | 0.01 | 0.321* | 0.6 |
| 7 | 39.7 | 33.7 | 51.3 | 0.01 | 0.42 | 0.09 |

Example 7

Introgression of LW Resistance QTLs into Additional Maize Lines

A maize plant comprising one or more, two or more, or three or more LW resistance QTLs is crossed with an elite maize line comprising a desirable trait (e.g., improved yield under water, temperature, or pest stress conditions), but susceptible to LW. $F_1$ progeny plants from this cross are assayed for one or more SNP markers exemplified in Tables 4 and 5 or molecular markers linked to those SNP markers to select for LW resistance QTLs. A selected $F_1$ progeny plant is then backcrossed with the parent elite maize line comprising the desirable trait (recurrent parent). Plants from the $BC_1$ generation are also genotyped using SNP markers exemplified in Table 4, or a linked marker, to select for LW resistance QTLs. After multiple rounds of backcrossing (e.g., 5-7 generations) with the recurrent parent line, a new elite maize line is obtained comprising both LW resistance and the desirable trait in the recurrent parent line. Using the above introgression and marker-assisted selection strategy, the pyramiding or stacking of multiple LW resistance QTLs can be achieved.

As various modifications could be made in the constructions and methods herein described and illustrated without departing from the scope of this disclosure, it is intended that the foregoing description shall be interpreted as illustrative rather than limiting. The breadth and scope of the present disclosure should not be limited by any of the above-described exemplary embodiments, but should be defined only in accordance with the following claims appended hereto and their equivalents. All patent and non-patent documents cited in this specification are incorporated herein by reference in their entireties.

Example 8

Validation of LW_2.01

CV131061 has an LW rating score of 3.7 and carries favorable alleles at the LW_2.01 marker loci SEQ ID NO: 17, SEQ ID NO:33, and SEQ ID NO: 36 which are in the LW_2.01 interval. CV145619 has an LW score of 7 and carries unfavorable alleles at LW_2.01 marker loci SEQ ID NO:17, SEQ ID NO:33, and SEQ ID NO:36. $F_2$ plants derived from CV145619/CV131061 are developed and three SNP markers within the LW_2.01 interval: SEQ ID NO:17, SEQ ID NO:33, and SEQ ID NO:36, are used for genotyping using the methods described in Example 1. 24 $F_2$ plants carrying homozygous favorable alleles at LW_2.01 and 24 $F_2$ Plants carrying homozygous unfavorable alleles at LW_2.01 are selfed to produce $F_3$ Progeny. 48 $F_3$ progeny plants along with CV131061 and CV145619 are grown with two replications and are artificially inoculated to trigger infection. $F_3$ progeny plants carrying the favorable alleles at LW_2.01 show a reduction of 1.4 LW rating score (6.64−5.24=1.4) when compared to $F_3$ progeny plants carrying the unfavorable alleles (Table 9). The "favorable" and "unfavorable" alleles in this case are directed to the resistant parental line CV131061 and the susceptible parental line CV145619. However, one of skill in the art will recognize that a "favorable" allele at one locus may be an "unfavorable" allele in a different genetic background. Thus, the invention is not limited to the "favorable" and "unfavorable" alleles exemplified herein.

TABLE 9

Validation of LW_2.01 for $F_3$ progeny plants.

| | $F_3$ Progeny with favorable alleles | $F_3$ Progeny with unfavorable alleles |
|---|---|---|
| Mean LW score | 5.24 | 6.64 |
| Variance | 1.00 | 1.54 |
| *p-value | | 1.3E−08 |

*Student t-test was used to calculate p-value.

48 $F_3$ progenies derived from bi-parental populations (CV145619/CV131061) are crossed with six testers to generate the $F_1$ hybrid plants for efficacy of LW_2.01 under artificial disease pressure (Table 10).

TABLE 10

Populations for further validation

| Donor Parent | Recurrent Parent | Recurrent Parent |
|---|---|---|
| CV131061 | CV145619 | CV136745 |
| | | CV156670 |
| | | CV319586 |
| | | CV143587 |

TABLE 10-continued

Populations for further validation

| Donor Parent | Recurrent Parent | Recurrent Parent |
|---|---|---|
| | | CV825464 |
| | | CV668519 |

$F_1$ hybrid plants carrying the favorable alleles at these loci show a reduction of 0.81 in LW rating score (5.82−5.01=0.81) when compared to hybrid plants carrying the unfavorable alleles (Table 11).

Further validation of LW_2.01 is conducted in a $F_3$ inbred bi-parental population generated from a cross between CV577261 and CV836449 where CV836449 is the resistant line. Disease rating is determined as the percentage of plants with Late Wilt within a row. SEQ ID NO:11, SEQ ID NO:15, and SEQ ID NO:27, are used for genotyping using the methods described in Example 1. $F_3$ inbred plants carrying the favorable alleles at these loci show a reduction of 45.25 in LW rating score (47.60−2.35=45.25) when compared to inbred plants carrying the unfavorable alleles (Table 12).

TABLE 11

Efficacy of LW_2.01 in $F_1$ progeny plants.

| | $F_1$ Hybrid plants with favorable alleles | $F_1$ hybrid with unfavorable alleles |
|---|---|---|
| Mean LW score | 5.01 | 5.82 |
| Variance | 0.92 | 1.54 |
| *p-value | | 3.41E−18 |

*Student t-test was used to calculate p-value.

TABLE 12

Efficacy of LW_2.01 in $F_3$ progeny plants.

| | $F_3$ Progeny with favorable alleles | $F_3$ Progeny with unfavorable alleles |
|---|---|---|
| n | 20 | 25 |
| Mean LW score | 2.35% | 47.60% |
| Variance | 4.68% | 20.83% |
| *p-value | | 5.00E−02 |

*Student t-test was used to calculate p-value.

What is claimed is:

1. A method of creating a population of Late Wilt (LW) resistant corn plants or corn seeds, said method comprising:
   a) obtaining a first progeny population of plants seeds;
   b) genotyping said first progeny population of corn seeds or plants grown therefrom at one or more marker loci linked to, and within 10 centimorgans (cM) of LW resistance quantitative trait locus (QTL) LW_2.01;

c) selecting from said first progeny population one or more corn plants or corn seeds comprising said one or more of said marker loci linked to said LW resistant QTL LW_2.01 linked to an LW resistance allele selected from the group consisting of:

SEQ ID NO: 8, comprising a T at position 244;
SEQ ID NO: 9, comprising a G at position 277;
SEQ ID NO: 10, comprising an A at position 430;
SEQ ID NO: 11, comprising a C at position 269;
SEQ ID NO: 12, comprising a G at position 61;
SEQ ID NO: 13, comprising an A at position 61;
SEQ ID NO: 14, comprising a T at position 61;
SEQ ID NO: 15, comprising a T at position 138;
SEQ ID NO: 16, comprising a C at position 61;
SEQ ID NO: 17, comprising an A at position 101;
SEQ ID NO: 21, comprising a C at position 148;
SEQ ID NO: 22, comprising a C at position 101;
SEQ ID NO: 23, comprising a C at position 101;
SEQ ID NO: 26, comprising an A at position 674;
SEQ ID NO: 27, comprising a G at position 298;
SEQ ID NO: 28, comprising a G at position 483;
SEQ ID NO: 29, comprising an A at position 44;
SEQ ID NO: 30, comprising a C at position 101;
SEQ ID NO: 31, comprising a T at position 90;
SEQ ID NO: 32, comprising a G at position 871;
SEQ ID NO: 33, comprising a G at position 460;
SEQ ID NO: 34, comprising an A at position 252
SEQ ID NO: 35, comprising an A at position 225;
SEQ ID NO: 36, comprising a T at position 232;
SEQ ID NO: 37, comprising an A at position 321; and
SEQ ID NO: 38, comprising a G at position 101; and d) crossing said selected one or more corn plants or corn plants grown from said seeds with a second corn plant to produce a second progeny corn seed or plant grown therefrom comprising said one or more of said marker loci linked to said LW resistance allele at said LW resistant QTL LW_2.01.

2. The method of claim 1, further comprising: crossing a first LW resistant corn plant comprising said LW resistance QTL LW_2.01 with a second corn plant of a different genotype to produce said first progeny population of corn plants or corn seeds.

3. The method of claim 1, wherein said LW resistance QTL LW_2.01 provides mild resistance or resistance to infection by Harpophora maydis.

4. The method of claim 1, wherein said second progeny corn plants exhibits reduced dark yellow to brownish macerated pith, brownish-black vascular bundle, or both compared to corn plants or corn seeds lacking said LW resistance QTL LW_2.01 under a similar growth condition.

5. The method of claim 1, wherein said step b) comprises assaying a single nucleotide polymorphism (SNP) marker.

6. The method of claim 1, wherein said step b) comprises the use of an oligonucleotide probe.

7. The method of claim 6, wherein said oligonucleotide probe is adjacent to a polymorphic nucleotide position in said marker locus.

8. The method of claim 1, wherein said step b) comprises detecting a haplotype.

9. A method of creating a population of Late Wilt (LW) resistant corn plants or corn seeds, said method comprising:

a) genotyping a first population of corn plants or corn seeds at one or more marker loci linked to, and within 10 centimorgans (cM) of any one of marker loci linked to an LW resistant allele selected from the group consisting of:
SEQ ID NO: 8, comprising a T at position 244;
SEQ ID NO: 9, comprising a G at position 277;
SEQ ID NO: 10, comprising an A at position 430;
SEQ ID NO: 11, comprising a C at position 269;
SEQ ID NO: 12, comprising a G at position 61;
SEQ ID NO: 13, comprising an A at position 61;
SEQ ID NO: 14, comprising a T at position 61;
SEQ ID NO: 15, comprising a T at position 138;
SEQ ID NO: 16, comprising a C at position 61;
SEQ ID NO: 17, comprising an A at position 101;
SEQ ID NO: 21, comprising a C at position 148;
SEQ ID NO: 22, comprising a C at position 101;
SEQ ID NO: 23, comprising a C at position 101;
SEQ ID NO: 26, comprising an A at position 674;
SEQ ID NO: 27, comprising a G at position 298;
SEQ ID NO: 28, comprising a G at position 483;
SEQ ID NO: 29, comprising an A at position 44;
SEQ ID NO: 30, comprising a C at position 101;
SEQ ID NO: 31, comprising a T at position 90;
SEQ ID NO: 32, comprising a G at position 871;
SEQ ID NO: 33, comprising a G at position 460;
SEQ ID NO: 34, comprising an A at position 252
SEQ ID NO: 35, comprising an A at position 225;
SEQ ID NO: 36, comprising a T at position 232;
SEQ ID NO: 37, comprising an A at position 321; and
SEQ ID NO: 38, comprising a G at position 101,
wherein said marker loci is associated with an LW resistance quantitative trait locus (QTL) LW_2.01;

b) selecting from said first population one or more progeny corn plants or corn seeds comprising said one or more of said marker loci linked to said LW resistance allele; and c) producing from said selected one or more progeny corn plants or corn seeds via crossing a second progeny population of corn plants grown therefrom or corn seeds comprising said one or more of said marker loci linked to said LW resistance allele.

10. The method of claim 9, further comprising: crossing a first LW resistant corn plant comprising said LW resistance QTL LW_2.01 with a second corn plant of a different genotype to produce said first population of corn plants or corn seeds.

11. The method of claim 9, further comprising:

a) crossing said first progeny corn plant with itself or a plant from said second progeny population of corn plants to produce one or more further progeny plants grown therefrom or corn seeds; and b) selecting a further progeny corn plant or corn seed comprising said one or more of said marker loci linked to said LW resistance allele.

12. The method of claim 1, wherein said one or more of said marker loci is selected from the group consisting of:
SEQ ID NO: 8, comprising a T at position 244;
SEQ ID NO: 9, comprising a G at position 277;
SEQ ID NO: 10, comprising an A at position 430;
SEQ ID NO: 11, comprising a C at position 269;
SEQ ID NO: 12, comprising a G at position 61;
SEQ ID NO: 13, comprising an A at position 61;
SEQ ID NO: 14, comprising a T at position 61;
SEQ ID NO: 15, comprising a T at position 138;
SEQ ID NO: 16, comprising a C at position 61;
SEQ ID NO: 17, comprising an A at position 101;
SEQ ID NO: 21, comprising a C at position 148;
SEQ ID NO: 22, comprising a C at position 101;
SEQ ID NO: 23, comprising a C at position 101;
SEQ ID NO: 26, comprising an A at position 674;
SEQ ID NO: 27, comprising a G at position 298;
SEQ ID NO: 28, comprising a G at position 483;
SEQ ID NO: 29, comprising an A at position 44;
SEQ ID NO: 30, comprising a C at position 101;
SEQ ID NO: 31, comprising a T at position 90;
SEQ ID NO: 32, comprising a G at position 871;
SEQ ID NO: 33, comprising a G at position 460;
SEQ ID NO: 34, comprising an A at position 252;
SEQ ID NO: 35, comprising an A at position 225;
SEQ ID NO: 36, comprising a T at position 232;
SEQ ID NO: 37, comprising an A at position 321; and
SEQ ID NO: 38, comprising a G at position 101.

13. The method of claim 1, wherein said second progeny corn plant or corn seeds further comprises a second LW resistance allele linked to an LW resistance QTL selected from LW_1.01, LW_1.02, LW_1.03, LW_1.04, LW_3.01, LW_3.02, LW_3.03, LW_4.01, LW_4.02, LW_5.01, LW_5.02, LW_6.01, LW_7.01, LW_8.01, or LW_10.01.

14. The method of claim 13, wherein said second LW resistance allele is located in a chromosomal interval flanked by:
any two of marker loci SEQ ID NOs: 1 to 3;
marker loci SEQ ID NOs: 47 and 48;
marker loci SEQ ID NOs: 41 and 42;
marker loci SEQ ID NOs: 45 and 46;
marker loci SEQ ID NOs: 24 and 25;
any two of marker loci SEQ ID NOs: 4 to 7 and 18 to 20;
marker loci SEQ ID NOs: 49 and 50;
marker loci SEQ ID NOs: 256 and 257; or
any two of marker loci SEQ ID NOs: 44, and 258 to 264.

15. The method of claim 9, wherein said second progeny corn plant or corn seeds further comprises a second LW resistance allele at an LW resistance QTL selected from LW_1.01, LW_1.02, LW_1.03, LW_1.04, LW_3.01, LW_3.02, LW_3.03, LW_4.01, LW_4.02, LW_5.01, LW_5.02, LW_6.01, LW_7.01, LW_8.01, or LW_10.01.

16. The method of claim 15, wherein said second LW resistance allele is located in a chromosomal interval flanked by:

any two of marker loci SEQ ID NOs: 1 to 3;
marker loci SEQ ID NOs: 47 and 48;
marker loci SEQ ID NOs: 41 and 42;
marker loci SEQ ID NOs: 45 and 46;
marker loci SEQ ID NOs: 24 and 25;
any two of marker loci SEQ ID NOs: 4 to 7 and 18 to 20;
marker loci SEQ ID NOs: 49 and 50;
marker loci SEQ ID NOs: 256 and 257; or
any two of marker loci SEQ ID NOs: 44, and 258 to 264.

17. The method of claim 1, wherein said second progeny plant or corn seed of step d) is homozygous for said one or more of said marker loci linked to said LW resistance allele.

* * * * *